US008198430B2

(12) United States Patent
Prior et al.

(10) Patent No.: US 8,198,430 B2
(45) Date of Patent: Jun. 12, 2012

(54) IMMUNOGENIC SEQUENCES

(75) Inventors: Joann Lisa Prior, Salisbury (GB); Richard Geoffrey Prior, Salisbury (GB); Paul Gareth Hitchen, Wiltshire (GB); Anne Dell, London (GB); Richard William Titball, Salisbury (GB)

(73) Assignee: The Secretary of State for Defence (GB)

( * ) Notice: Subject to any disclaimer, the term of this patent is extended or adjusted under 35 U.S.C. 154(b) by 366 days.

(21) Appl. No.: 12/277,077

(22) Filed: Nov. 24, 2008

(65) Prior Publication Data
US 2010/0080828 A1    Apr. 1, 2010

Related U.S. Application Data

(63) Continuation of application No. 10/516,215, filed as application No. PCT/GB03/02338 on May 30, 2003, now abandoned.

(30) Foreign Application Priority Data

May 31, 2002 (GB) .................................. 0212666.2

(51) Int. Cl.
*A61K 39/02* (2006.01)
*C07H 21/00* (2006.01)

(52) U.S. Cl. ................... 536/123.1; 536/23.2; 536/23.1; 536/24.33; 435/320.1; 435/41; 435/6.12; 435/6.1

(58) Field of Classification Search ........................ None
See application file for complete search history.

(56) References Cited

U.S. PATENT DOCUMENTS

| 3,148,120 | A | 9/1964 | Otto |
| 5,066,596 | A | 11/1991 | Manning et al. |
| 5,951,987 | A * | 9/1999 | Cherwonogrodzky et al. .................... 424/252.1 |
| 6,261,568 | B1 | 7/2001 | Gicquel et al. |
| 6,268,171 | B1 | 7/2001 | Meyer et al. |
| 6,350,454 | B1 | 2/2002 | Thune |
| 6,406,705 | B1 | 6/2002 | Davis et al. |
| 644,804 | A1 | 9/2002 | Lam et al. |
| 6,444,210 | B1 | 9/2002 | Kournikakis et al. |
| 6,444,445 | B2 | 9/2002 | Nikolich et al. |
| 6,444,804 | B1 | 9/2002 | Lam et al. |
| 6,552,006 | B2 | 4/2003 | Raz et al. |
| 7,399,756 | B2 | 7/2008 | Jomaa et al. |

(Continued)

FOREIGN PATENT DOCUMENTS
EP         0250614 A1        1/1988
(Continued)

OTHER PUBLICATIONS

Belanger, M et al, Microbiology, 1999, vol. 145, pp. 3505-3521, Functional analysis of genes responsible for the synthesis of the B-band O antigen of *Pseudomonas aeruginosa* serotype 06 lipopolysaccharide.*

(Continued)

*Primary Examiner* — Albert Navarro
*Assistant Examiner* — Ginny Portner
(74) *Attorney, Agent, or Firm* — Kilpatrick Townsend & Stockton LLP

(57) ABSTRACT

The application relates to nucleic acids which encode enzymes responsible for the production of the O-antigen of *Francisella tularensis*, and their use as or in the production of vaccines and in diagnosis.

14 Claims, 19 Drawing Sheets

U.S. PATENT DOCUMENTS

Figure 1:
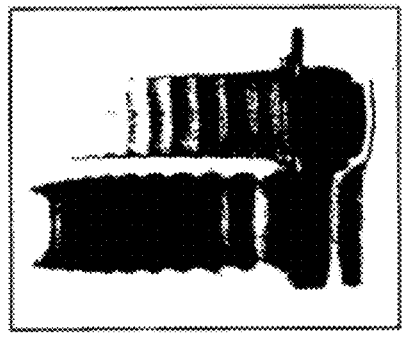

| | | | |
|---|---|---|---|
| 7,588,744 | B1 | 9/2009 | Sylvester |
| 7,592,326 | B2 | 9/2009 | Karaolis |
| 2001/0024653 | A1 | 9/2001 | Gicquel et al. |
| 2003/0022226 | A1 | 1/2003 | Hooper et al. |
| 2004/0087555 | A1 | 5/2004 | Belmant et al. |
| 2006/0280759 | A1 | 12/2006 | Titball et al. |
| 2007/0066801 | A1 | 3/2007 | Engler et al. |
| 2007/0128225 | A1 | 6/2007 | Prior et al. |
| 2007/0218086 | A1 | 9/2007 | Tiollier |
| 2007/0264233 | A1 | 11/2007 | Michell et al. |
| 2007/0292386 | A9 | 12/2007 | Campbell et al. |
| 2008/0207568 | A1 | 8/2008 | Belmant |
| 2009/0087456 | A1 | 4/2009 | Eyles et al. |
| 2009/0196887 | A1 | 8/2009 | Morita et al. |
| 2010/0021501 | A1 | 1/2010 | Michell et al. |
| 2010/0047283 | A1 | 2/2010 | Michell et al. |
| 2010/0119524 | A1 | 5/2010 | Ulaeto et al. |
| 2010/0204184 | A1 | 8/2010 | Montero et al. |

FOREIGN PATENT DOCUMENTS

| | | |
|---|---|---|
| EP | 2123285 | 11/2009 |
| GB | 2321103 A | 7/1998 |
| GB | 212666.2 | 7/2002 |
| GB | 0511722.1 | 6/2005 |
| GB | 0625587.1 | 12/2007 |
| GB | 2445028 A | 6/2008 |
| RU | 2240822 C2 | 4/2004 |
| WO | WO-88/08430 | 11/1988 |
| WO | WO-92/13871 | 1/1992 |
| WO | WO-93/11791 | 6/1993 |
| WO | WO-9741234 | 11/1997 |
| WO | WO-01/26683 | 4/2001 |
| WO | WO-01/58485 | 8/2001 |
| WO | WO-02/18600 | 3/2002 |
| WO | WO-02/60935 | 8/2002 |
| WO | WO-03/068151 | 8/2003 |
| WO | WO-03/102191 | 12/2003 |
| WO | WO-2004/004654 | 1/2004 |
| WO | WO-2004/084935 | 10/2004 |
| WO | WO-2004/098491 | 11/2004 |
| WO | WO-2005/013918 | 2/2005 |
| WO | WO-2005/021708 | 3/2005 |
| WO | WO-2005/054258 | 6/2005 |
| WO | WO-2005/063802 | 7/2005 |
| WO | WO-2006/067635 | 6/2006 |
| WO | WO-2006/103568 | 10/2006 |
| WO | WO-2006/111019 | 10/2006 |
| WO | WO-2006/131752 | 12/2006 |
| WO | WO-2007/028985 | 3/2007 |
| WO | WO-2007/034166 | 3/2007 |
| WO | WO-2007/097789 | 8/2007 |
| WO | WO-2008/012538 | 1/2008 |
| WO | WO-2008/075075 | 6/2008 |
| WO | WO-2010/086617 | 8/2010 |
| WO | WO-2010/119245 | 10/2010 |

OTHER PUBLICATIONS

Waag, DM et al, Clinical and Diagnostic Laboratory Immunology, Mar. 1995, vol. 2(2), pp. 143-148, Cell-mediated and humoral immune responses after vaccination of human volunteers with the Live Vaccine strain of *Francisella tularensis*.*

Waag, DM e tal FEMS Immunology and Medical Microbiology, vol. 13, pp. 205-209, 1996, Immunogenicity of a new lot of *Francisella tularensis* live vaccine strain in human volunteers.*

"*Francisella tularensis*", Poster presented at ASM Meeting, Baltimore, MD Mar. 20-23, 2005, 11 pgs.

Agarwal, et al., "Antisense therapeutics: is it as simple as complementary base recognition? Abstract Only", Molecular Medicine Today 2000, 6: 72-81.

Agarwal, et al., "Medicinal chemistry and therapeutic potential of CpG DNA", Trends in Mol. Med. 2002, 8:114-121.

Alkhuder, et al., "Glutathione Provides a Source of Cysteine Essential for Intracellular Multiplication of *Francisella tularensis*", PLoS Pathogens 2009, 5:1-11.

Ascher, et al., "Modulation of Delayed-Type Hypersensitivity and Cellular Immunity to Microbial Vaccines; Effects of Cyclophosphamide on the Immune Response to Tularemia Vaccine,", Infection and Immunity 1977, 18(2): 318-323.

Atkins, et al., "Chacterisation of an acapsular mutant of *Burkholderia pseudomallei* identified by signature tagged mutagenesis", Journal of Medical Microbiol. 2002, 51(7):539-547.

Bowie, et al., "Deciphering the Message in Protein Sequences: Tolerance to Amino Acid Substitutions", Science 1990, 247:1306-1310.

Broekhuijsen, et al., "Genome-Wide DNA Microarray Analysis of *Francisella tularensis* Strains Demonstrates Extensive Genetic Conservation within the Species but Identifies Regions that are Unique to the Highly Virulent *F. tularensis* subsp. tularensis", Journal of Clinical Microbiology 2003, 41(7): 2924-2931.

Buchele, et al., "Studies on pathogenesis and immunity in tularemia II. Immune Response of the white rat to bacterium tularense", Journal of Immunology 1949, 63(2): 135-145.

Burke, "Immunization Against Tularemia Analysis of the Effectiveness of Live *Francisella tularensis* Vaccine in Prevention of Laboratory Acquired Tularemia", Journal of Infectious Diseases 1977, 135(1): 55-60.

Candela, et al., "Poly-gamma-glutamate in bacteria", Molecular Microbiology 2006, 60(5): 1091-1098.

Casetti, et al., "Drug-Induced Expansion and Differentation of Vy9Vo2 T Cells in Vivo: The role of exogenous IL-2", Journal of Immunology 2005, 1593-1599.

Chamberlain, "Evaluation of Live Tularemia Vaccine Prepared in a Chemically Defined Medium", Applied Microbiology 1965, 13(2):232-235.

Champion, et al., "Comparative genomic characterisation of *Francisella tularensis* starains", pLoS Pathogens 2009, 5:e1000459.

Chen, et al., "Tularemia in BALB/c and C57BU6 mice vaccinated with *Francisella tularensis* LVS and challenged intradermally, or by aerosol with virulent isolates of pathogen: protection varies depending on pathogen virulence, route of exposure, host genetic background", Vaccine 2003, 21: 3690-3700.

Clemens, et al., "Virulent and Avirulent Strains of *Francisella tularensis* Prevent Acidifcation and Maturation of Their Phagosomes and Escape Into the Cytoplasm in Human Macrophages", Infection and Immunity 2004, 72(6):3204-3217.

Conlan, et al., "Different host defences are required to protect mice from primary systemis vs pulmonary infection with the faculative intracellular bacterial pathogen, *Francisella tularensis* LVS", Microb. Pathog. 2602, 32:127-134.

Conlan, "Vaccines against *Francisella tularensis*—past, present and future", Expert Rev. Vaccines 2004, 9(3): 307-314.

Database Kegg [Online]. "Glutamale metabolism—*Francisella tularensis* subsp. tularensis SCHU S4", XP002468730. Retrieved from KEGG/Pathway/FTU/FTU00251.HTML Feb. 19, 2007.

Genbank Accession No. AASP0100000.1, *Francisella tularensis* subsp. holarcitica FSC200, whole genome shotgun sequence, Jan. 17, 2007.

Davis, et al., "Pathology of Experimental Pneumonic Plague Produced by Fraction-1 Positive and Fraction-1 Negative Tersinia pestis in Agrican Green Monkeys (*Cercopithecus aethiops*)". Arch. Pathol. Lab. Med 1996, 120(2):156-163.

Drabick, et al., "Analysis of Active Live Immunization Versus Passive Humoral Immunotherapy Against Attenuated and Virulent Strains of *Francisella tularensis*", Vaccine Research 1997, 6(2): 67-74.

Dunstan, et al., "Comparison of the Abilities of Different Attenuated *Salmonella typhimurim* Strains to Elicit Humoral Immune Responses against a Heterologous Antigen", Infection and Immunity 1998, 66(2): 732-740.

Eigelsbach, et al., "Prophylactic effectiveness of live and killed tularemia vaccines. I. Produuction of vaccine and evaluation in the white mouse and guinea pig", Journal of Immunology 1961, 87: 415-425.

Ellis, et al., "Tularemia", Clinical Microbiology Reviews 2002, 15(4):631-646.

EMBL-Bank Sequence Database, "Accession No. AF140738", Jan. 19, 2000.

Eyles, et al., "Protection afforded against aerosol challenge by systemic immunisation with inactivated *Francisella tularensis* live vaccine strain (LVS)", Microbial Pathogenesis 2008, 44: 164-168.

Forest, et al., "Type IV pili structure, assembly adn immunodominance applcations to vaccine design", Vaccines 1997, 97: 167-173.

Forslund, et al., "Direct repeat-mediated deletion of a type IV pilin gene results in major virulence attenuation of *Francisella tularensis*", Molecular Microbiology 2006, 59(6):1818-1830.

Forslund, et al. "Type IV pili is required for Virulence of *Francisella tularensis*" Abstract, American Society for Microbiology Biodefense Research meeting, Mar. 20-23, 2005.

Gil, et al., "Presence of Pill on the Surface of *Francisella tularensis*", infection and immunity 2004, 3042-3047.

Golovliov, et al., "A method for allelic replacements in *Francisella tularensis*", FEMS Microbiology Letters 2003, 222: 273-280.

Golovliov, et al., "Adjuvanticity of ISCOMs incorporating a T cell-reactive lipoprotein of the facultative intracellular pathogen *Francisella tularensis*", Vaccine 1995, 13(3): 261-267.

Gossman, et al., "Quantitative Structure-Activity Relations of yo T Cell Activation by Phosphoantigens", Journal of Med. Chem. 2002, 45:4868-4874.

Gray, et al., "The identification of five genetic loci of *Francisella novicida* associated with intracellular growth", FEMS Microbiology Letters 2002, 215: 53-56.

Green, et al., "Efficacy of the live attenuated *Francisella tularensis* vaccine (LVS) in a murine model of disease", Vaccine 2005, 23: 2680-2686.

Greenspan, et al., "Defining Epitopes: It's not as easy as it seems", Nature Biotechnology 1999, 7:936-937.

Hahn, et al., "The type-4 pilus is the major virulence-associated adhesin of *Pseudomonas aeruginosa*—a review", Gene 1997, 99-108.

Hartmann, et al., "Delineation of a CpG Phosphorothioate Oligodeoxynucleotide for Activating Primate Immune Responses in Vitro and in Vivo", Immunology 2000, 164: 1617-1624.

Hertle, et al., "Dual-function vaccine for *Pseudomonas aeruginosa*: characterization of a chimeric exotoxin A-pilin protein", Infection and Immunity 2001, 69(11):6962-6969.

Hooper, et al., "DNA vaccination with Vaccinia Virus L1R and A33R Genes Protects Mice against a Lethal Poxvirus Challenge", Virology 2000, 266: 329-339.

Hubalek, et al., "Comparative proteome analysis of cellular proteins extracted from highly virulent *Francisella tularensis* ssp. tularensis and less virulent *F. tularensis* ssp. holarctica and *F. tularensis* ssp. mediaasiatica", Proteomics 2004, 4:3048-3060.

Isherwood, et al., "Vaccination strategies for *Francisella tularensis*", Advanced Drug Delivery Reviews 2005, 57(9): 1403-1414.

Kadzhaev, et al., "Identification of genes contributing to the virulence of *Francisella tularensis* SCHU S4 in a Mouse Intradermal Infection Model", PLoS One 2009, 4.

Kawula, et al., "Use of Transposon-Transposase Complexes to Create Stable Insertion Mutant Strains of *Francisella tularensis* LVS", Applied Environmental Microbiology 2004, 70:6901-6904.

Kieffer, et al., "Francisella novicida LPS has greater immunobiological activity in mice than *F. tularensis* LPS, and contributes to *F. novicida* murine pathogenesis", Microbes and Infection 2003, 5:397-403.

Kiss, et al., "Characterization of fig operon mutants of *Francisella novicida* U112", FEMS Micriobiol Letters 2008, 270-277.

Koskela, et al., "Cell-mediated immunity against *Francisella tularensis* after natural infection", Scandinavian Journal of Infectious Diseases 1980, 12(4): 281-287.

Krieg, "The CpG motif: Implications for clinical immunology, Abstract Only", BioDrugs 1998, 10(5): 341-346.

Kuolee, et al., "Vaccines and therapeutic agents for tularemia", Informa Healthcare 2007, 267-275.

Kus, et al., "Signifcant differences in type IV pilin allele distribution among *Pseudomonas aeruginosa* isolates from cystic fibrosis (CF) versus non-CF patients", Microbiology 2004, 150:1315-1326.

Lai, et al., "Expression of IgIC is necessary for intracellular growth and induction of apoptosis in murine macrophages by *Francisella tularensis*", Microbial Pathogenesis 2004, 37:225-230.

Larsson, et al., "Molecular evolutionary consequences of niche restriction in *Francisella tularensis*", PLoS Pathoges 2009, 5:e1000472.

Larsson, et al., "The complete genome sequence of *Francisella tularensis*, the causative agent of tularemia", Nature Genetics 2005, 37(2): 153-159.

Lascola, et al., "Rapid comparative genomic analysis for clinical microbiology", Genome Res 2008, 18:742-750.

Lauriano, et al., "MgIA regulates transcription of virulence factors necessary for *Francisella tularensis* intraamoebae and intramacrophage survival", Proc. Natl. Acad. Sci. USA 2004, 101:4246-4249.

Lavine, et al., "Immunization with heat-killed *Francisella tularensis* LVS elicits protective antibody-mediated immunity", Eur. J. Immunology 2007, 37: 3007-3020.

Law, et al., "Antibody Neutralization of the Extracellular Enveloped Form of Vaccinia Virus", Virology 2001, 280: 132-142.

Maier, et al., "In Vivo Himarll-Based Transposon Mutagenesis of *Francisella tularensis*", Applied Environmental Microbiology 2006, 72(3):1878-1885.

Mann, et al., "Rationally designed tularemia vaccines", Expert Rev Vaccines 2009, 8(7): 877-885.

McLendon, et al., "*Francisella tularensis*: Taxonomy, Genetics, and Immunopathogenesis of a Potential Agent of Biowarfare", Annual Rev. Microbiology 2006, 60:167-185.

Michell, et al., "A capB mutant of *Francisella tularensis*", URL:http://www.sgm.ac.uk/meetings/pdfabstracts/keele2005abs.pdf (2008) Sep. 12, 2005.

Michell, et al., Unpublished U.S. Appl. No. 10/550,773, filed Jul. 20, 2006.

Mitchell, et al., "Development of real-time PCR assays for the specific detection of *Francisella tularensis* ssp. Tularensis, holartica and mediaasiaatica", Molecular and Cellular Probes 2010, 24:72-76.

Nano, et al., "A *Francisella tularensis* Pathogenicity Island Required for Intramacrophage Growtn", Journal of Bacteriology 2004, 186(19):6430-6436.

Nielsen, et al., "Peptide nucleic acids (PNAs): Potential anti-sense and anti-gene agents", Anti-Cancer Drug Des. 1993, 8:53-63.

O'Hagan, "Recent developments in vaccine delivery systems", Current Drug Targets, Infectious Disorders, Bentham Science Publishers, Hilversum, NL 2001, 1(3): 273-286.

Overholt, et al., "An analysis of forty-two cases of laboratory-acquired tularemia. Treatment with broad spectrum antibiotics", The American Journal of Medicine 1961, 30: 785-806.

Oyston, et al., "Tularemia vaccine: past, present and future", Antonie van Leeuwenhoek 2005, 87:217-281.

Pavlov, et al., "Cryptic plasmid pFNL10 from *Francisella novicida*-like F6168: the base of plasmid vectors for *Francisella tularensis*", FEMS Immunol. Med. Microbiol. 1996, 13:253-256.

Pechous, et al., "A *Francisella tularensis* Schu S4 Purine Auxotroph is Highly Attenuated in Mice but Offers Limited Protection Against Homologous Intranasal Challenge", PLoS One 2008, 3(6):1-10.

Pechous, et al., "Construction and Characterization of an Attenuated Purine Auxotroph in a *Francisella tularensis* Live Vaccine Strain", Infection and Immunity 2006, 74(8):4452-4461.

Petrovsky, et al., "Freeing vaccine adjuvants from dangerous immunological dogma", Expert Rev. Vaccines 2008, 7(1):7-10.

Petrovsky, et al., "New-Age Vaccine Adjuvants: Friend or Foe?", BioPharmIntemational.com. Aug. 2, 2007, 12 pgs.

Poquet, et al., "Expansion of Vy9Vo2 T Cells Is Triggererd by *Francisella tularensis*-Derived Phosphoantigens in Tularemia but Not after Tularemia Vaccination", Infection and Immunity 1998, 2107-2114.

Qin, et al., "Identification of an essential *Francisella tularensis* subsp. tularensis Virulence Factor", Infection and Immunity 2009, 152-161.

Qin, et al., "Identification of transposon insertion mutants of *Francisella tularensis* tularensis strain Schu S4 deficient in intracellular replication in the hepatic cell line HepG2", BMC Microbiology 2006, 6:69.

Quarry, et al., "A *Francisella tularensis* subspecies novicida purF mutant, but not a purA mutant, induces protective immunity to tularemia in mice", Vaccine 2007, 25:2011-2018.

Reed, et al., "A simple Method of Estimating Fifty Per Cent Endpoints", Am. J. Hygiene 1938, 27(3):493-497.

Richards, et al., "Identification of Francisella genes up-regulated in the macrophage", Poster at the International Conference on tularemia Nov. 2006.

Robertson, et al., "Detection of the Osmoregulator Betaine in Methanogens", Applied and Environmental Microbiology 1990, 56:1504-1508.

Robertson, et al., "β-Aminoglutaric acid is a major soluble component of *Methanococcus thermolithotrophicus*", Biochimica et Biophysica Acta 1989, 992:320-326.

Rohmer, et al., "Comparison of *Francisella tularensis* genomes reveals evolutionary events", Genome Biol 2007, 8:R102.

Rohmer, et al., "Potential source of *Francisella tularensis* live vaccine strain attenuation determined by genome comparison", Infectious Immunology 2006, 74:6895-6906.

Roper, et al., "Extracellular Vaccine Virus Envelope Glycoprotein Encoded by the A33R Gene", Journal of Virology 1996, 70(6):3753-3762.

Salomonsson, et al., "A Role for a Type IV Pilus in Virulence of *Francisella tularensis*", Abstract, American Society for Microbiology Meeting, Jun. 5-9, 2005.

Salomonsson, et al., "A Role for a Type IV Pilus in Virulence of *Francisella tularensis*", Abstract, Society for General Microbiology 155th Meeting, Sep. 6-9, 2004, Trinity College Dublin, Ireland.

Samrakandi, et al., "Genome diversity among regional populations of *Francisella tularensis* subspecies", FEMS Microbiology Letters 2004, 237:9-17.

Sandstrom, et al., "A Capsule-Deficient Mutant of *Francisella tularensis* LVS Exhibits Enhanced Sensitivity to Killing by Serum but Dimished Sensitivity to Killing by Polymorphonuclear Leukocytes", Infection and Immunity 1988, 56(5):1194-1202.

Sandstrom, et al., "Antigen from *Francisella tularensis*: Nonidentity Between Determinants Participating in Cell-Mediated and Humoral Reactions", Infect. Immun. 1984, 12(1):101-106.

Sandstrom, "The Tularaemia Vaccine", J. Chem. Tech. Biotechnology 1994, 59:315-320.

Shen, et al., "Mice sublethally infected with *Francisella novicida* U112 develop only marginal protective immunity against systemic or aerosol challenge with virulent type A or B strains of *F. tularensis*", Microbial Pathogenesis 2004, 37:107-110.

Sorokin, et al., "*Francisella tularensis* resistance to bactericidal action of normal human serum", FEMS Immunology and Medical Microbiology 1996, 13:249-252.

Su, et al., "Genome-Wide Identification of *Francisella tularensis* Virulence Determinants", Infection and Immunity 2007, 3089-3101.

Sullivan, et al., "Characterization of the Siderophore of *Francisella tularensis* and Role of fslA in Siderophore production", Journal of Bacteriology 2006, 188:3785-3795.

Svensson, et al., "Evolution of Subspecies of *Francisella tularensis*", Journal of Bacteriology 2005, 187(11):3903-3908.

Tarnvik, et al., "Nature of Protective Immunity to *Francisella tularensis*", Review of Infectious Diseases 1989, 11(3):440-451.

Tarnvik, et al., "Orchestration of the protective immune response to intracellular bacteria: *Francisella*", FEMS Immunology and Medical Microbiology 1996, 13(3):221-225.

Tarnvik, et al., "Stimulation of Human Lymphocytes by a Vaccine Strain of *Francisella tularensis*", Infection and Immunity 1975, 12(5):951-957.

Tarnvik, et al., "Stimulation of Subpopulations of Human Lymphocytes by a Vaccine Strain of *Francisella*", Infection and Immunity 1978, 20(3):698-704.

Tempel, et al., "Attenuated *Francisella novicida* Transposon Mutants Protect Mice against Wild-Type Challenge", Infection and Immunity 2006, 74(9):5095-5105.

Titball, et al., "Will the enigma of *Francisella tularensis* virulence soon be resolved?", Trends in Microbiology 2003, 11(3):118-123.

Tonjum, et al., "The pilus colonization factor of pathogenic neisserial species: organelle biogenesis and structure/function relationships—a review", Gene 1997, 155-163.

Twine, et al., "A Mutant of *Francisella tularensis* Strain SCHU S4 Lacking the Ability to Express a 58-Kilodalton Protein Is Attenuated for Virulence and Is an Effective Live Vaccine", Infection and Immunity 2005, 73(12):8345-8352.

Vogel, et al., "Acetylornithinaase of *Escherichia coli*: Partial Purification and some Properties", J. Biol. Chem. 1955, 218:97-106.

Weiner, "The immunobiology and clinical potential of immunostimulatory CpG oligodeoxynucleotides", Journal of Leukocyte Biology 2000, 68:456-463.

Yamamoto, et al., "Ability of oligonucleotides with certain palindromes to induce interferon production and augment natural killer cell activity is associated with their base length, Abstract Only", Antisense Research and Development 1994, 4:119-122.

Zhao, et al., "Effect of different chemically modified oligodeoxynucleotides on immune stimulation, Abstract Only", Biochemical Pharmacology 1996, 51:173-182.

Altschul et al., "Gapped BLAST and PSI-BLAST: a new generation of protein database search programs," *Nucleic Acids Research*, 25(17):3 3 89-3 4 02 (1997).

Altschul et al., "Basic Local Alignment Search Tool," *J. Mol. Biol.*, 215:403-410 (1990).

Barker et al., "Basis for the Failure of *Francisella tularensis* Lipopolysaccharide to prime human Polymorphonuclear leukocyte", *Infection and Immunity*, 74(6):3277-3284 (2006).

Belanger et al., "Functional analysis of genes responsible for the synthesis of the B-band O-antigen of *Pseudomonas aeruginosa* serotype 06 lipopolysaccharide," *Microbiology*, 145:3505-3521 (1999).

Bosio et al. "Active suppression of the pulmonary immune response by *Francisella tularensis* Schu4," *J. Immunol.*, 178(7):4538-47 (2007).

Burrows et al., "Molecular characterization of the *Pseudomonas aeruginosa* serotype O5 (PAO1) B-band lipopolysaccharide gene cluster," *Molecular Microbiology*, 22:481-495 (1996).

Carlsson et al., "Enzyme-Linked Immunosorbend Assay for Immunological Diagnosis of Human Tularemia," *Eur. J. Biochem.*, 269:6112-6118 (2002).

Chart, H., "Lipopolysaccharide: Isolation and Characterization," In: Raton B, Arbor A (eds.) *Methods in Practical Laboratory Bacteriology*, CRC Press, London, Tokyo, pp. 11-20 (1994).

Cowley et al., "Isolation and characterization of *Francisella novicida* mutants defective in lipopolysaccharide biosynthesis," *FEMS Microbiol. Lett.*, 182:63-67 (2000).

Deng et al. "Identification of *Francisella tularensis* genes affected by iron limitation," *Infect. Immun.* 74:4224-36 (2006).

Drabick et al., "Passive Protection of Mice against Lethal *Francisella tularensis* (Live Tularemia Vaccine Strain) Infection by the sera of human recipients of the Live Tularemia Vaccine", *The American Journal of the Medical Sciences*, 308:83-87 (1994).

Dreisbach et al., "Purified Lipopolysaccharide from *Francisella tularensis* Live Vaccine Strain (LVS) Induces Protective Immunity against LVS Infection That Requires B Cells and Gamma Interferon," *Infect. Immun* 68:1988-1996 (2000).

Eigelsbach et al. "Murine Model for Study of Cell-Mediated Immunity: Protection Against Death from Fully Virulent *Francisella tularensis* Infection," *Infection and Immunity*, 12:999-1005 (1975).

Florence et al., Chapter 25.2 "Formulation" in vol. 5 of *Comprehensive Medicinal Chemistry* (Corwin Hansch; Chairman of Editorial Board), pp. 567-591, Pergamon Press (1990).

Fulop et al., "Role of lipopolysaccharide and a major outer membrane protein from *Francisella tularensis* in the induction of immunity against tularaemia," *Vaccine*, 13(13):1220-1225 (1995).

Fulop et al., "Role of antibody to lipopolysaccharide in protection against low- and high-virulence strains of *Francisella tularensis*," *Vaccine*, 19:4465-4472 (2001).

Fulop et al., "Production and Characterization of Monoclonal Antibodies Directed against the Lipopolysaccharide of *Francisella tularensis*," *Journal of Clinical Microbiology*, 29:1407-1412 (1991).

Fulop et al. "Role of two outer membrane antigens in the induction of protective immunity against *Francisella tularensis* strains of different virulence," *FEMS Immunol. Med. Microbiol.*, 13:245-7 (1996).

Groisman, "How bacteria resist killing by host-defense peptides," *Trends.Microbiol.*, 2: 444-449 (1994).

Hatch et al., "Immunogenic Substances in culture filtrates and lysates of Pasteurella Tularensis", *Journal of Bacteriology*, 88, 566-573 (1964).

Hollis et al., "*Francisella philomiragia comb. nov.* (Formerly *Yersinia philomiragia*) and *Francisella tularensis* Biogroup Novicida (Formerly *Francisella novicida*) Associated with Human Disease," *J. Clin. Micro.* 27(7):1601-1608 (1989).

Johnson et al., Chapter 25.3 "Routes of Administration and Dosage Regimes," in vol. 5 of Comprehensive Medicinal Chemistry (Corwin Hansch; Chairman of Editorial Board), pp. 593-613, Pergamon Press (1990).

Karlsson et al., "Sequencing of the *Francisella tularensis* Strain Schu 4 Genome Reveals the Shikimate and Purine Metabolic Pathways, Targets for the Construction of a Rationally Attenuated Auxotrophic Vaccine," *Microb. Comp. Genom.*, 5:25-39 (2000).

Kenne. et al., "Bacterial Polysaccharides *The polysaccharides*,"vol. 2, Academic Press, Ed. Gerald O. Aspinall, pp. 287-362 (1983).

Khlebnikov et al., "Outer membranes of a lipopolysaccharide-protein complex (LPS-17 kDa protein) as chemical tularemia vaccines," *FEMS Immunology and Medical Microbiology*, 13:227-233 (1996).

Knirel et al., "Somatic antigens of *Pseudomonas aeruginosa*," *Eur. J. Biochem.* 150:541-550 (1985).

Laemmli, "Cleavage of Structural Proteins during the Assembly of the Head of Bacteriophage T4," *Nature* 227:680-685 (1970).

Lipman et al. "Rapid and Sensitive Protein Similarity Searches," *Science*, 227:1435-1441 (1985).

Mack et al. "A New Cell Assay to Determine the Virulence of *Francisella tularensis*," *Letters in Applied Microbiology*, 19:158-160 (1994).

Mc. Murry et al. "Diversity of *Francisella tularensis* Schu4 antigens recognized by T lymphocytes after natural infections in humans: identification of candidate epitopes for inclusion in a rationally designed tularemia vaccine," *Vaccine.*, 25(16):3179-91 (2007).

Narayanan et al., "Immunotherapy of Tularemia: Characterisation of a monoclonal antibody reactive with *Francisella tularensis*", *Journal of Leukocyte Biology*, 53:112-116 (1993).

Nutter et al., "Antigens of *Pasteurella Tularensis*: Preparative Procedures", *Applied Microbiology*, 22(1):44-48 (Jul. 1971).

Olsufiev et al., "Comparative Study of Strains of *B. Tularense* in the Old and New World and Their Taxonomy," *J. Hyg. Epidemiol. Microbiol. Immunol.*, 3:138-149 (1959).

Ormsbee et al., "Studies on Bacterium Tularense Antigens, II Chemical and Physical Characteristics of Protective Antigen Preparations", *Journal of Immunology*, 74: 359-370 (1995).

Ormsbee et al., "Studies on Bacterium Tularense Antigens, I. The Isolation, Purification, and Biologic Activity of Antigen Preparations from *Bacterium tularense*", *Journal of Immunology*, 74: 351-358 (1995).

Petrosino et al. "Chromosome rearrangement and diversification of *Francisella tularensis* revealed by the type B (OSU18) genome sequence," *J. Bacteriol.*, 188(19):6977-85 (2006).

Prior et al., "Preliminary analysis and annotation of the partial genome sequence of *Francisella tularensis* strain Schu 4," *Journal of applied microbiology*, 91 614-620 (2001).

Russell et al. "The efficacy of ciprofloxacin and doxycycline against experimental tularaemia," *J. Antimicrob. Chemother.*, 41:461-5 (1998).

Sanger et al., "DNA sequencing with chain-terminating inhibitors," *Proc. Natl. Acad. Sci. U.S.A.*, 74:5463-5467 (1977).

Sonnhammer et al., "A hidden Markov model for predicting transmembrane helices in protein sequences," In: Glasgow S, Littlejohn T et al. (eds.) *The sixth international conference on intelligent systems for molecular biology*, AAAI Press, Menlo Park, CA, pp. 175-182 (1998).

Vinogradov et al. "Structural Analysis of *Francisella tularensis* Lipopolysaccharide," *Eur. J. Biochem.*, 269:6112-6118 (2002).

Waag et al., "Immunogenicity of a new lot of *Francisella tularensis* live vaccine strain in human volunteers," *FEMS Immunol. Med. Microbiol.*, 13:205-9 (1996).

Waag et al. "Cell-mediated and humoral immune responses after vaccination of human volunteers with the live vaccine strain of *Francisella tularensis*." *Clin. Diagn. Lab. Immunol.*, 2:143-8 (1995).

Waldo et al. "Proteome cataloging and relative quantification of *Francisella tularensis tularensis* strain Schu4 in 2D PAGE using preparative isoelectric focusing," *J. Proteome. Res,.* 6(9):3484-90 (2007).

Westphal et al., "Bacterial Lipopolysaccharides," *Methods in Carbohydrate Chemistry*, Ed. Roy L. Whistler, Academic Press, 5:83-91 (1965).

Whitfield et al., "Modulation of the surface architecture of Gram-negative bacteria by the action of surface polymer:lipid A-core ligase and by determinants of polymer chain length," *Mol. Micro.*, 23(4):629-638) (1997).

International Search Report dated Nov. 3, 2003 in International Application No. PCT/GB03/02338.

* cited by examiner

Fig.4.

SEQ ID NO 41

```
   1  tcttttataa atgatgatag caaacaaaaa ataataggtt ctgtgcacaa aaaacttaaa
  61  ttatattgaa aatagctaaa ccgctgttat ttaagatttg aaaagcaata aatatcaatg
 121  gtttagcaaa tgaattatca tataaaagaa gtattctggt caattatttt atcattctta
 181  aaatcacaaa aaggtataca taccaatgat gaagccaaat taagattgtt tattgaagct
 241  gtattttatg tgttacgtac aggctgtcaa tggagaatgt taccatttta ttatggtaaa
 301  tatagatcaa tacataagcg tttttaaagat tggtgtgata agatatatt ttctagatta
 361  tttaaatcag tacaaaaccc tgatttacaa gaagtcatgc ttgattcaac aatagcaaga
 421  gcacatgctt gtgctacggg atatgataaa gatgataacc aagcaattgg tagatcagtt
 481  ggtaggataa ccactaaaat ccatgctatg actgatgctt taggtaatcc aatagaaata
 541  ttgttgtcag aggataaaac tcatgatagt aaagtagcta tagatttact aaaaaatgta
 601  tataatacaa aagttatcgc tgatagagca tatcattcta atgaaatcag gcagcatatt
 661  caaggtatat cctctgaagc tgttatccct tgtaaatcaa atactctaaa ccatatacct
 721  tttgatagtc atgtatataa agaaagacat ttgatagaga atttcttttc taaaattaag
 781  cattttagaa gagtattctc tagatttgat aaaaccattt tagcatatat aggaatgatt
 841  aaattagctt gtacttttat ttggttacga tgaatattta tttttgtgca cagaacctaa
 901  tttgcatttt tgtgcacaaa gaaaatttt ttgatataat agactttaat aggatatttt
 961  ctaaaaatta acaaatgtct ttctacgata atagaacgct taatttcgtg gtaataatag
1021  ttttaactat tattactgtt aattggactt tctatatttt caagcaagat gttaatttac
1081  atttttact tgcattagtt ttgctgagat gcttgtcatc tttttacta cttagagatt
1141  atatggctag ttggcgtaag tcgactcaaa aaacttttt acgtaaggct tttattaatt
1201  tgccagtatt tttcatagtg gcattatttt tttatggcaa agtcacttt tcgttgatat
1261  tctctgagtt tttattttat gttttttga tcagtttaag tgtctacttt tattggtatt
1321  tgatgaacag aggatcagtg gataaaagta aaactgcggt tatttatggt gcaggtgctg
1381  caggaacaaa gattgctcaa gaacttgctt ctgctggtta tcgcatcaaa tgttttgttg
1441  atgacaatga aactttacaa aaaagaagta ttgatagtaa aaggttcta tctaaagctg
1501  aattaacaaa actattgcta tctagtagat ttgaccttt ggttattgca ttgccaagaa
1561  atgcaaacca agtagtcaaa aatatatata agaatttga aaggatttt aatcagatta
1621  gaattatgcc gcctcttgag gaaattcttc aagatgagaa ttttatgtca cagttgaagc
1681  ctgtttcact ctatgatcta ttagcgcgtg atactaagag tttagataaa gaatctatct
1741  ctaattttat caaaaataag gtggtgctag tcacaggagc tggaggtagt ataggttctg
1801  aaatagtaca tcaatgtatc aagtatcagg caaaagagtt gatattggtt gatcatagtg
1861  agtttaactt atataaaatt actgaggagt gtagtcattt taatatcaat agtgtgctat
1921  gttctgtttg tgatagaaaa gcattggctg aggttttca aaagtatact ccaaatatag
1981  tatttcatgc tgctgcctac aagcatgttc ccttagttga ggagaatatc tctagagcaa
2041  ttagaaataa tatcttaggt actaagaatg ctatagatct ggctatagaa gctggtgttg
2101  agtcatttat attgatttcc actgataaag cagtgcgacc aacgaatgtt atgggggcta
2161  ccaagagagt ttgtgagctg tatttacaga atgttgatcc caaaaatacc aagcttgctg
2221  cagtgcgttt tggtaatgtg cttggtagta gtggcagtgt gattccaaaa tttgaagagc
2281  aaataagaaa aggtggtcct gttacagtta ctcatcctga aattacacgt tattttatgt
2341  tgataccaga agcttgtgaa ctggtcctac aagctggtgc tattgcaaaa aattcagagg
2401  tctttgtctt agatatgggg caacctgtca agattattga tcttgctaaa caatttatta
2461  gactttctgg tagaggtgat attgatatta aaatagttgg tttgcgtcca ggagagaaac
2521  tttacgaaga gcttttgata gaggaagatg atgttagtac cgactacaaa gatatttta
2581  ttggtagaag gactttttac gatattaata ctctaaacca agatattgaa tcgttgatca
2641  aggatgatgt tgatcagctt gtgatattaa agaaaattgt tccggaattt gaacatagat
2701  tgaatgggta gtggtttat gttttatgag gttttaaaa gattgcttga tattttactt
2761  tcttttatgg ggttgttgtt attaagtcct attttcttaa ttattatttt tatgataaag
2821  aaagattcaa aaggacctat atttttaaa caaagcgct atggtaaaga taagcaattt
2881  ttttacatat ataagtttag aactatgtat gttgatactc caaagatat gccaacgcac
2941  atgttacagg atccatcgaa atgtataact aaggttggag gatttttaag gaaatcatct
3001  ttagatgagt tgccacaaat tataaatatt ctaaaggtg aaatgagcat cgtgggtcca
3061  agaccagcat tatggaatca agatgactta atagcacaaa gagataagta tggggcaaat
```

Fig.4 (Cont I).

```
3121  gctgtgcctg tgggactgac tggctgggca cagattaatg gtagggatga attaccaata
3181  cctgataaag ctaaacttga tggtgattat gtaaaaaata aaagtacatg gtttgattta
3241  aaatgtattt ttttgacagt attttctgtt tttgccaaaa agggcgtcgt tgagggtggt
3301  actggagctt taggtaacaa agaggattta aagtagtatg aaaaaaagaa tcttagttac
3361  aggtttgagt agctatattg gtaactcatt tgcggctaaa tataactcag attttagtat
3421  cgataaaata tctttgcgcg atgtttcgtg ggcaaatata gacttaagtg gttatgatgc
3481  tgtattgcat gtcgctggaa ttgcccatac ttcaaaggat cctaaactaa aagaaaata
3541  ctataaaata aatacgcaat taacttatga tctggcaaaa caagctaaag atcaaggtgt
3601  tcgacagttt gtgttttaa gtagtattat agtttatggt gatagtgcgc caataggtca
3661  acaaaaagtt ataactaaat ataccgaacc taaaccagat gatttttatg gagatagtaa
3721  gcttcaaact gaaattaagc taaatagcct ggctagtgat gactttaata ttgctataat
3781  cagaccacca atggtatatg gagaaggctc aaaaggcaac tatccaaagt tggttaaact
3841  tgcaaagtat acttttattt ttcctaatat taataaccaa agaagtgtta tatctataga
3901  taatttatct aaagagattg cagaaataat tttgcaaact aaacatggag ttttctact
3961  tcaagataat gaatattttt gcacttcaca gtttataaaa aactatagaa aagatgtttt
4021  aggtaagaga acttatctga caaaattt taatccaatt ataagattgc ttgctaaaaa
4081  agtagatttt attaataaag tttttgggaa tttgacttat gagaagtaag ttattattca
4141  tagctaatga ttttgatatt gtaatatatc gtttcagaag agaagtaatc gagtctttg
4201  ctgctaaaga gtatgagata gtactagtaa caccatattc taagaaagca gaggttttt
4261  gtaaagtct tggtgttaag tatataaatg ttgatataga tagcgaggc aaaaatcctt
4321  ttaaggattt gcttctttta tttaactatt tcaaaataat aaaaaaagaa aaacctgatt
4381  acatttttag ctatacaatt aaaccaatt tgtatgttgg gttagtgaat ttgttttta
4441  ggaagaagtt ttatccaaat gtaacaggct taggaagtgt ttttgctaat catggtattg
4501  ttcagaagtt tataatatct ttatataagt tatcatttaa aagcaccaca aaagtattct
4561  ttcagaatga gcaaaataaa aagttattta tagctaagaa aataatcagt ggagaaaaat
4621  caatattatt accaggttct ggggtaaact tagatgaaaa taaatatgtt gactatccta
4681  aagaccaagg aatattaaaa ttcgttttc ttggccgaat aatgaaagaa aaggggattt
4741  atgaattgtt agaagccttt gctatacttg agaaaaaata taaaatatt agtcttgaca
4801  tttatggttt ttgtgatgaa aataaatcta attttatggg aaaggttaat acgataaaat
4861  cagtaaaatt ttatggtttt actgataata ctaaagaaaa aatagctagt gcacatgcag
4921  ttgttttgcc atcttaccat gaaggaatgt caaatgtgct gttagaagca gctgcgatag
4981  gtagacctgt aattgcgtca gatattcctg ggtgtagaga aattttgat gatggtctct
5041  ctggcttatc atgtaaccct aatgatgtga gttctttacg taactcatta gagcagttta
5101  taaatatgtc gtatactgat aaaatagcta tgagctataa agctagagct aagatagaaa
5161  aagattttga tagaagtatt gttgtcaatg catacttaca gcaaaattaa taataagggt
5221  ttaaattatg agtttatatg aggatatagt cgctaaaaga gaaaaggttt cattggttgg
5281  cttgggttat gttggtttac caatagctat tgcatttgca aaaaaaatag atgtgttagg
5341  atttgatatt tgtgaaacaa aagttcaaca ttataaggat ggttttgatc caacaaaaga
5401  agtaggagat gaggctgtca gaaatacgac aatgaaattt agttgtgatg aaacaagtct
5461  taaagagtgt aaatttcata ttgttgcagt tcctacacca gttaaagcag ataaaactcc
5521  tgatttgacg ccgattatta aggcaagtga gacggttggt aggaatcttg tcaaaggcgc
5581  ttatgttgtg tttgaatcaa ctgtttatcc tggtgttaca gaagatgttt gcgtaccaat
5641  acttgaaaaa gagtctggct tgaggtctgg tgaagatttc aaagttggtt actctcctga
5701  gaggataaat cctggtgata aggttcatag gttagaaaca attatcaaag tagtatctgg
5761  tatggatgaa gagtctttag atactatagc aaaagtttat gagctagtag tagacgcagg
5821  agtttataga gctagtagta taaaagtggc tgaagctgct aaggttatag aaaactctca
5881  aagagatgtt aatatagctt ttgttaatga gttatcgata atatttaatc agatgggtat
5941  tgatactcta gaggttttag cagcagctgc aactaaatgg aatttcttaa actttaagcc
6001  tggtcttgtt ggtggacatt gtattggtgt tgacccatat tacctaacgt acaaggcagc
6061  tgagcttgga tatcattctc aggtaatatt atctggtcgt aggataaatg atagtatggg
6121  taaatttgta gttgagaatt tagtcaaaaa actgatatct gcagatatac ctgttaagcg
6181  agctagagta gcaatttcg gctttacttt taagaagac tgtcctgaca ctaggaatac
6241  tcgagttata gatatggtaa aagagctcaa cgagtatggt atagagccat atattataga
6301  tccggtagct gataaagaag aggctaaaca tgagtatgga cttgagtttg atgatctaag
6361  taaaatggtc aatctagatg cgatcattat tgctgttagt cacgaacagt ttaaagatat
```

Fig.4 (Cont II).

```
6421  aacaaagcaa cagtttgata ggctatatgc gcataattct agaaagatta tatttgacat
6481  caaaggtagt ttagataaat ctgagtttga aaaagattat atttattgga gattgtagtg
6541  gcttacgata atgttaaatt tcctcatggt tcgttttttt tggtgactgg aggtgcgggt
6601  tttattggct ctaatttatg tgaagtttta cttagtaagg gttatagagt taggtgttta
6661  gatgatctct caaatggtca ctatcacaat gttgagccgt ttttaactaa ttctaattat
6721  gagtttataa aaggtgatat tagagattta gatacttgca tgaaagcttg tgaaggtatt
6781  gattatgttc tacatcaagc tgcttgggga agcgtaccaa gaagtattga gatgccatta
6841  gtgtatgaag atataaatgt taaaggtgca ttaaatatgc ttgaagcggc tagacaaaat
6901  aacgttaaaa aatttgtcta tgcttctagt tcatcagtat atggtgatga gccaaattta
6961  cctaaaaaag aaggtagaga aggaaatgtt ttatcaccct atgcatttac aaagaaagct
7021  aatgaagagt gggcgagact atacacaaag ttatatggtc tagatactta tggtctaaga
7081  tattttaatg ttttcggtag aagacaagat cctaatggtg cgtatgcagc agttatacct
7141  aaatttatca aacagttatt aaatgatgaa gcgccaacta taatggaga tggtaaacag
7201  tcgagagatt ttacatatat agagaatgtt attgaggcaa atcttaaagc atgtttagca
7261  gatagtaagt atgccggaga gtcttttaat atagcttatg gaggtagaga gtatcttata
7321  gatttgtact ataatctttg tgatgccttg ggtaaaaaaa tagagccaaa ttttggtcca
7381  gatagagcgg gtgatattaa gcatagtaat gctgatattt cgaaggctag gaatatgctc
7441  ggatataatc cggaatatga ttttgaatta ggcataaagc atgctgttga gtggtattta
7501  attaattaaa tggtatttta atcaagtgta cataaaaaaa gtgtctttta aaatttata
7561  tttatattta ctagcttttt gtattatttt tagtttagaa tttaaatttg ctatattgaa
7621  tattatagtt tatcttccgg cttgtatttt gggtttttta gctcttaaaa aactatttgt
7681  cggaaatatt gttaagaaac aattagcttt cctttttttc tttttctttt tatcaatgat
7741  ttatttaata atagtccaaa taatcttact tgatgcagca tcattgtttc ctcagttttt
7801  atttaacatt ttgatcgcga taggtttttg taactttatt tttgtttcat atgataataa
7861  tgaaaattat tttttaata tgtctaaaat aatatttttt gttactttct tacaatctat
7921  ttttgtattt ctttcaaggt attatatatt tttaaatgat tggatattct tttttttagt
7981  gaaaaaggg aatattgaga tttcgaatgt tattgaatat aagttaagag tattcggact
8041  tagtaacgct ggaggggatg gtttaggatt ttcaattact ataggattat gttttctat
8101  attttatttt atcaaatata ttaaaggtaa atctatattt accaaactta tgctgtttgt
8161  accttttaatt cttattgtgt tttctaatat tttcatatct agaacatcac tcttaacttc
8221  ttcacttata ttgttaataa caatatttta tatatatatt aaaaagaaa aattactgtt
8281  tattataata ttggcgctat tctttttatc aatatggata ttgttcaaat taaatttgaa
8341  tttgagttgg gcttttgaaa atatttactc gtacattcaa tctggcgatt tttcacatgg
8401  aagtctaagt gttttaatca ataaaatgct ttttgtgcca gataaccttt tgacttggat
8461  atttggttgt gaggatgtta gtaatactga tattggttat attaaatatt tatactatta
8521  tgggattata tttagtatgt ttttttatat tcttattatt ttcttgtact ttgaaatgag
8581  aaaatgtttt atattttcag agtatcgatc attatttcta ttgttgttaa tagtatgttt
8641  agttttcaa gcaaaaataa ttttttttgac agtaggatta tttactaaat taaccattat
8701  attatttatt ttttctctta agaaaacag ctttacaact aggagtgtga tttgaaaagg
8761  tttgtacatt taataataaa ccttaaccaa ggtggtgctg aaacaatgct ttataaactt
8821  tgcaaatcta tggataagtc aatatatcat attacgatta tatcacttat gggtagggga
8881  gtatttgcaa ataagttaga agcttatggt gttaaagttt atacattaaa tttaaataaa
8941  tttaatgtac tatttgtatt gtttaaatat attaagatta tcagaagaat aaagcctgat
9001  gttattcatg cttggatgta tcatgcaaat gtaatttcta tattatgcaa gcctttttat
9061  agaaagacta aatatataaa tagtataaga atgggattgg agaattatga tggtcataag
9121  aatcttacaa agtttatgat aaagttgaat gcaaaatttt ctaagttctc agatttaaca
9181  ttaaataatt caaagaaatc attagaagat catcaaaata taggttttaa aaaccaatgc
9241  tttatagcaa atggttttga taaagatgtt tttaaaccga gcttttttaaa gtatgaaaaa
9301  ttcgtttaa ataatgattt agatgataat gttaaaatta taggtatcat agcaagaaat
9361  catgctgata aaaatatttc tcgtttctta caaatagcta atttattgtt aaaaagtaat
9421  cctagtttac ggttttttaat tgctggaaga gagtgttcga aaatagatat aggtagttat
9481  ctagataaca aaagtaatgt aaataagttt tttgtatttg aatctgtgga ttctagtgaa
9541  tacttaccag tattagattt atatttgtct acatcaaaag ttgaaggttt tccaaatata
9601  cttgcagaag ccatgctatg tgaagttcct attgttgctt ctaatgttgg agattgtaaa
9661  gatatactta atggatacgg tgaagttttt gagcttagtc aaggtaataa agaaataata
```

Fig.4 (Cont III).

```
 9721 gaaaagatta tgaaagtttt agaaacaacg gtagtcatga aaaagcgcat gagagaatat
 9781 ataataaata attttagtat agaagctatt ttggaaaaac acgaaaaact ttatcatgag
 9841 ggcagtgtct aatgtgtgga gtagtaggct tttactcatt taataaagaa gaaggttttg
 9901 actcaataat taatcaatca ttgctttcta taaagcatag agggtcggat gatagtgggt
 9961 attggtgcga caatcaagtt actctggggc atactagatt atcaatacac gatataacta
10021 atgcgggaca tcagccaatg ttatctaata gcggtaatac tgctattgtg tttaatggag
10081 aaatatataa ttacttatcc ataaaaatc agctattaag tgaatattca aatcttaaat
10141 ttaaaagtaa cagtgatact gaggttttgg tcaatgctat tgaactttgg ggtatagata
10201 aaactttaga aaaatgcata ggaatgtttg cttttggagt ttacagtaga aaaactagtt
10261 gcttaatact agctagagat agatttggcg agaagccatt atatttggt atccaaaatg
10321 gtattttggg ttttgcatca gaattgaagg cacttaagcc attaaaggaa tgtggctgga
10381 ggtttgatat agatagagat gctttagcaa catatatgag gtatgcttat gtaccaacac
10441 catactctat ttataaaaat atatctaaac taaatgtagg tagttacata aaatttgatg
10501 ctaaaggtaa tagtaaagag tataaatatt gggattctaa aaaagtacta gattcagaaa
10561 aatataaaga ttcgtatgat caagcaatcc tagatttaga aattaagctt aaaagtacac
10621 tatcaataca aatgcagtca gatgttcctc taggagcatt tttatccgga ggaattgact
10681 caacaactgt agttgctctt atgcaaagta tgtctaaaga taagataaac acttttagta
10741 taggttttaa tcaaaaagaa tataatgaag ctgagcatgc aagagcagta gcaaaacata
10801 taggtacaaa ccacacagat atgtatgtta cagaaagaga tgctcttgat gtaataccaa
10861 aacttgctgg aatatatgac gagccctttg ctgattcatc acaaatacca acgtatcttg
10921 tgagtaaaat agctaagtcg aaagtaacag ttgcactatc aggtgacgct ggtgatgagc
10981 tctttggcgg ttataataga tactttttag caccaaatat tgctaaaaaa atcaaatttg
11041 ctaagttact taaatatgca ccagatgctt ggataaaaaa agctgagata ttaaattttg
11101 gtaagttcgc tttattagca gataaactac taaaactaaa aagagttctc gaaaaagcaa
11161 aaacaaataa agagctttat gtactacttt gttcacaaat aaatgatact agctttgtgt
11221 taggagcaaa agagtatgat atattaagag ataagaatat ttatgatatt ccacaattat
11281 cttttccaaga gtggatgatg tttgttgatt ctaatacata tatgatagat gatatattgg
11341 ttaaggttga tagagcagct atggctaact ctctagagac aagagtgcca tttttagatc
11401 ataatattta tgaatttgct tattccttac caattgacta taaaatacaa cgaggtaacg
11461 gaaaagaat tttgaaagat ttgttatata aatatgtgcc agaaagtttg gtcaataggt
11521 ctaagatggg gtttggtatt ccgcttgcta aatggttaag agaagattta cgagagtggg
11581 cagataattt actggattat agtaaaatag acaagcaagg ttacttaagt cctgaggtgg
11641 tgcaaaaata ttggcaagag catttgagtg gtaaaagaaa ttggcaagca atattatgga
11701 atattctaat ttttcaggag tggttagata atgagtaaag taaatgtaac aaaaccatac
11761 ttaccagata taaataaata taaagctat gtaaataaaa tatacaaaaa tggatggctt
11821 actaataatg gtccgttagt gcaagagcta gaaaaagac ttgcaaagta tctaggtgtt
11881 aaaaatatag ttttagtatc aaatggtaca attgcattag aaatcgcgta tagagcgtta
11941 ggagtcaaag gaagtgcaat tactactcca ttttcatttg ttgctactac atcttcattg
12001 gtttctaaca atgtaaaacc agtgtttgtt gatattgatg agaatactct aagtatagac
12061 gtctctaaaa ttaagtatgc tattgaagag gatacttcag ctattgtgcc agttcatgtg
12121 tttggaaatg gttgtgaagt tgaaaaaata gacatgctgg ctaaaaaaca taacttaaaa
12181 gttatttatg atgcagcaca tgcttttgat gttaagtata gggtgagag tatattaaac
12241 tatggtgata tttcgacatt aagttttcat gcaacaaaga ttttttcattc tattgaagga
12301 ggtgcgctta tcattaatga tgatagtctt gttgaaaaag ttcgttattt cattaatttt
12361 ggtatagaaa gctcagaatc aatacctttac ttaggtacta atgctaaaat gaatgaattt
12421 gaggcggcta tgggactttg tgttctagat gatattatag aaattaagag caaaaggaaa
12481 gttattacag agatatatga ggctgggtta gatggattgg taaagtttca agaacagaat
12541 cagcattcta gtaggaatta tagctatttt ccagtaatat ttaggactga ggaggaactt
12601 ctcagagtac agaaagcact aatacaaaat gatataatat cgcgtagata tttttatcca
12661 tcattagata gtcttagtta tatagagcca aagcagtata tgccaatctc aagagatata
12721 tctaaaagaa tattatgttt gccaatttat gcagagttag aagacgataa aattaataaa
12781 ataattaata atatcaaaga ggtttcctca tgaaaaaaat atttgttgtt acagataata
12841 gaactattct aagtgatttt aaaaatatca ttggtagtaa aaatgatgta caggttgatt
12901 atttttgtag tttcaagagt caaacttctt ttgccaaaga aatatataac agtgagatta
12961 agccaataga tatgaaaaaa aatggcaatg atcttattgg taagtatgat ttaggttttt
```

Fig.4 (Cont IV).

```
13021 cttgtcattc gaaacaatta tttccagcaa aattagttaa ttcagtatta tgtataaata
13081 ttcatcctgg acttaatcca tataatagag ggtggtttcc acaggtcttc tctattataa
13141 ataaactacc tataggagca actattcatg tgatggatga agagatagat catggagata
13201 taatcattca ggaagaagtt gaagttaatt ctttcgaaaa ctctttgat gtttatgcta
13261 aagttcaaaa aaaagaagtt gagttgttca ctaaagtcat agatgatatt ttgaataata
13321 agttcactcg aatcaaacct aactccgaag gcaactataa ttcaattcat gattataaaa
13381 acatgtgtga aattgattta gataaaatag taacaatgcg ggaagcaatt gactatctaa
13441 gggctatgac acaccctcca tataaaaata gttatttcat tgatgagcat ggaaataaag
13501 tatttgttgc tcttgaactt gaaaagataa gttagaaaaa tgagccttaa aaaaaataca
13561 atatcaaatt atataacaca actatatact agcttaattg gtattgttat acttcctttg
13621 tatttacaac atttaagtca tgatgcattt ggtctgattg gttttttac agtttttcaa
13681 acgtggttac ggttgttgga tgttggtata acaccaactt tatcaagaga agtggctcat
13741 gttagaggta gtactgatga ctatcattac ttacgcaagt tggttagatc gttagagcta
13801 ttttttcatta ttgttggtgt tctggtattt attgtaatta gtacacattc aaggtatata
13861 tccacctctt ggttacatat aggctcgcta gatgctgata gtgtaagtgt atgtattgca
13921 cttatgggtt taatgtttgc attaagatgg gtgtctgatc tatatggtgg tggtttgcgt
13981 ggctttgaaa gacaggttct ttataataat ttaagtatca tacaaacgac actacagttt
14041 attggtggat tattatttat ctgctatgtg tctactaata ttatgtatta ttttgtatat
14101 cagacaataa ttgcgatact atatctagta tgtattgcaa ttgcatttta taaaatacta
14161 ccatcatcat ttagcgtggg tttaaggttt gattttaaaa taattagaaa agtgcttcca
14221 tttgcactag gcattgcata ttctacaaca gtttggatta ttgtcactca atctgataaa
14281 ttagtgttct cacatgtatt accattatct gagtatggtt atttatcttt attgatagtg
14341 atatctagtg ctgttacgat attgtcctct ccgattagca tagctattca gcctagaatg
14401 acaatgctat tagcccaaca aaatgtaaaa ggaatggaaa gcttatattt aaaatcatcc
14461 ttgatctcaa ttactttttt atctgctgta gtaacatgtg ttttgatgta ttctcatcag
14521 ctgttgcagt catggacagg aagtatggaa attgctaatt ggggtagtaa tatcttaaat
14581 atatatgttt tatcagcatc tattatttgt ataatatcat ttcaatattt tttacagtat
14641 gcttatggta agttaaagct acataataca tataatacaa ttagtttagt attttttgct
14701 cctatagtta tatatactgc ttataattat ggagtgtata ctacagcact attatggctt
14761 ggatatgcta tagtggggct gataatctgg atgcctattg tacaccatgt atttgctaaa
14821 ggtatcaata ggtattttt tataaattta gcagttatta ctatagtatg ttttttatta
14881 tcgttaatat ttaaggttg gtatatttat ccaagtaaaa ttgggttggt agaattaata
14941 ttgattgggt ttgcattttt atttatacaa atttgtatag agtatgtttt gtttcggtac
15001 aaggttttga ggtgtataga tgattaaagt ttcagtatgt gtgatgacat acaatcaaga
15061 aaagtatatt ggtcaatgtt tagagtcttt ggttactcaa gagactgatt ttgactttga
15121 gataatcgtt ggagatgatt tttctacaga tggtacaaga gatgttattc aagagtatca
15181 aaaaaagtat ccggatatca taaagccagt ttttagagat aagaatgtgg gaattactga
15241 aaatattaaa gaaatctatt ttgttgcaaa tggtgagtat atagctcata tggatggtga
15301 tgattatgca ttgcctggta aacttcaaat tcaggctgat tttttggata taatccaag
15361 atgtacggga gtttttcata atataaatat actctatcca aatggtaata tacaacatag
15421 taggtttgct tgttcaaata agagtatatt caatttatca gacactttac gcggagttgc
15481 tgttggtgca aatagttcaa aaatgttcag aacatcggtt ttggatgatt tgattttacc
15541 ggatatagag cttctagatt attattttca tgttataaca gcagaaaaag gttatttaag
15601 ttttttaaat tctaatgaat cctatagtgt gtacagaaaa ggtattggta tcacatctaa
15661 gtctaaggaa aaaatctata atacttatgc tggattattt gaatattttt tggatagata
15721 tcctgaagag aaattaaata tttgtatccc tgttgtgcaa atgataattt cggctattaa
15781 agggagatgt tttattagtg ctattcgtct attcaaaatt ttaattagat caagatgtat
15841 tccattagta agttggttta aatatagatt tgaaaaataa atatcattta gaggattatg
15901 tgaaatgaag ggaataattc tagctggtgg cagtggtaca aggctatatc cacttacctt
15961 gggtgttagc aaacagctgc tacctgttta tgacaagcca tgttatact atccactatc
16021 tgtgcttatg cttgcaggta ttagggagat attaattatc tctacagtgc gtgatatctc
16081 acttatccaa gagcttcttg gtgatggttc acaatttggt atacagttga gttataaaat
16141 ccagccatca ccagatgggc ttgctcaagc atttattctt ggtgaggagt ttttggcggg
16201 tgactcagct tgtttgatat taggagataa tatctactat ggtcaaggta tgactacaat
16261 gctagagtct gcaagagcac agtgtggagg tccagctggt ggcgcttgtg ttttggggtta
```

Fig.4 (Cont V).

```
16321 ttatgttaat gatccgcata gatatggtat agtcgaattt gataagcaaa aaaatgtaat
16381 ttcggtagag gaaaagccac agaatcctaa gtcacactat gctatcacag gtttatattt
16441 ttatgataat aatgttgttg agtatgctaa acaagtcaaa ccatctgcac gtggtgagct
16501 agagattact tcacttaatg agttatatct aaaagaaaat aagctaaatg tcgaactctt
16561 agggcgtggc tttgcttggc ttgatgctgg tacgcatgat tcattgctag aggcaggtca
16621 atatgtcgca actattgaga aaagacaagg gcttaaaatt gcatgtttgg aagaaattgc
16681 atggcgtaaa ggctttatct caacacaaca agttctagct caagctgaaa aactttctaa
16741 gacagagtat ggtcagtatc tgaagaattt aattaaggat ggtttataaa ttaatccgtc
16801 atacccatga aggtgggtat ctcataaaag ttggatatgt tttggagatt ccaatctgcg
16861 cagtaatgac aggtttggta atatatagcg atgttttaca atgactaaaa atggttttat
16921 gtatattctt acaaataagg ataatactgt tctgtacata gttgtaacat ctaatttgat
16981 aaaaagaatg tatgagcata acatagcct tgcagatggt tttactaaaa atataatgtt
17041 aataagttag tttattttga aatttatgaa gatataaaag cagcaattct gtgagaaaag
17101 cagttgaaaa aatgaaacag atcttggaaa gaacgaatta ttaatgagat gaatccgaat
17161 tggaatgatt tatatgaatt aatatgtgag taaaacttt gtcttactgg tgcagatagg
17221 tatctctaaa tatcagatgt gattgggaga ttaccgccta cgcggtaatg acaagtttat
17281 gcggtaatga tagtttagtg agagaatgac tagtcactat aggaatgatg atgtaatgag
17341 gaatgaaaaa atgaactaca aaccaaaaaa tatcctagta acaggtgcgg cgggattat
17401 tggtagtaac tatgtgcgta tgatgttatc acgctatagt gatatcaaaa taatctcgta
17461 tgataagctt acttatgcgg gtagtttaga taatctaaaa gacttgaata atgaacataa
17521 ccatactttt ataaaggtg atatttgtga tgaagttta gtatatcaaa cactgaaaga
17581 atataaaatt gatacgatag tacatttgc tgcagaatcg catgttgata attcaattgc
17641 taatccaaag gtatttttag aaacgaatgt gataggtaca tttacacttt tagattgtgc
17701 taaaaggtat tggttagatg agctaggttt agaagaaact agttgtaggt ttcatcatgt
17761 atctactgat gaggtatatg gtaccttggc aaaagatgaa ccagcctta ctgagattaa
17821 ggcttatgag ccaaattcac cgtattcggc atctaaggcg ggatctgatc atatttctag
17881 agcatatcat catacctata aacttccggt aacaatttca aattgttcaa caactatgg
17941 accataccaa catcgagaga aattaatccc tgtagtgata aatagttgta taaactacaa
18001 gcctattcct gtttacggag atggttcgaa tattcgagat tggctatatg tagaagatca
18061 ctgcgatgct atccagacaa ttgttgagaa aggagtggtt ggagaggttt ataatattgg
18121 tggtattaat gaagttgata atctaacctt ggtaaaaact atctgtaaac taatggatga
18181 atataaacca gaaaatgctc cacattctaa cttaatcaca tttgtggaag atagaaaagg
18241 acatgattgg cgttatgcta ttgataacag caagattcag aatgagttag gatggaagcc
18301 atcacaagat tttgataaga tgtttagaca aactattgag ttttatctat agcttaaata
18361 tttatcttat gagtatctct aaaaaatcaa tttaatttat ttttgtgtta aaaagtagtg
18421 ttcgcaagaa tatagttaat ccgaaagata tttgtagaaa aagatatttg tagaaatgtt
18481 ataatgtcta ataaaaatgc catcatatag ccaagatttt agagacatcg taattaataa
18541 acatgaagaa ggtatgacgg agttcgagct gagtaagttt tttaacatag ataagcgtac
18601 agttgtttca tggatagagt tttataaaag aaccggagat tatagttcaa agcaaggagt
18661 tggttgtggc agagtcgcta gctttaccga taaacattg attgaacagt atttgataga
18721 tcatccagat gcaagtgcat tagatataaa agaagcatta gcccctgata ttccaagaag
18781 tacattttat gattgtctta atagacttgg ttttagtttt aaaaaaagac tccaaaatat
18841 aagcaaagaa aagaacatga aaggttggag tatatagaaa aactaaaaga aatagccaat
18901 aaatttgatg tacaaatatt atatctacct ccgtactctc cagatttaaa tcctattgaa
18961 aaggtttggg ctaactatta aaaaatatt tagaaaagtg aataatagtt ttgaaaaatt
19021 ttgtgatgct atctcttatg tgtttaacaa aatactctcg gattaactat atcatgctgc
19081 taaaatattc ttggtattct ctggtcaaaa ctgacataat gatgctctac tttgtataag
19141 gtttgctaca aatattatct aaacaaacat acaaggtaa tttttagaga tcctattata
19201 aacctactat ctaaatttag taagttaagt tatgacaata tttaatttgc tgatttattg
19261 ttgaatatat tagctttcta tataattaat caatatcaaa gttatttagg ttttttataat
19321 gattactcct attatcttat ctggaggatt cggctcaagg ctatggccac tatcacgaga
19381 ggcatcgcca aagcagttta tcggcttggt tgatgaacat agtctattag aaaatacaat
19441 taagcgacta gataatgtca aggatataac ttcacctgta gttgtctgta atgaaagtca
19501 tagattccaa gttgctgaag tgttgcggaa aatcaataaa aaaggcgata tactcctaga
19561 gccattagcc agaaatactg ctccagcaat tgcacttgca gcactacatt tagctattaa
```

Fig.4 (Cont VI).

```
19621 tgatccaaat acaattatgc tagttttagc tgctgaccat catattgaaa atctggagat
19681 ttttcatcaa gctatcgaaa aagcacagca aaaagttatt aaagatgatt ctttagttac
19741 ctttggcatt acaccaactt gtcctcatga aggctatggt tatattaaac aagggtaca
19801 gactactgta aatggagttt ataaggtaga taaatttgtt gagaagccta gtgtggtcgt
19861 tgcacaagag tatttagata gtggcaaata ctattggaat agcggtatgt ttatgttcac
19921 agctagagtg tatttagagg ttttagagaa gttacagcca gagatttaca gaggatgtga
19981 aaaaacttat caaaagtcac agcaggattt agattttgtg cgttttgata aacaaagctt
20041 tgccctagtt caatcacagt caatagacta cgcagttatg gagaaagcaa ctaatgttgc
20101 tatagtgcct atgcaacaaa gtggctggtc tgatgttggc tcttgggact ctttgtatga
20161 tattgctgca aagatagtt gtggtaatgt ggttattggc gatgtgatta ctagtaatgt
20221 caaaaatagt tatttacgct cgcatgatcg tttattggct gcagtcggag ttaatgattt
20281 aataattgtt gaaacagcag atgctatact tgtcgcggat aagaacaaaa ctcaagatgt
20341 caaaaaaata gtcgaagttt tgaaaattca gcagcgaagt gaattattac agcataagca
20401 aatttataaa ccttgggggtt cagcgacaat attagaggat aagtctggtt ataagataca
20461 ggcgattcaa cttgaaccgg gcaagaagtt atcattacag caacattatc accgtagtga
20521 gcattggatt gtgatttctg gaactgctac ggtaactatt ggtactacta agtctattgt
20581 tagaccaaat gagtctgtat atataaaaat aggcgaatct cacagacttg aaaataatgg
20641 caagattcca gttattctta tagaagtaca agttggagaa tatataagtg aagacgatat
20701 tgttagacta gatacaagta gttaatataa aaacaattag atagaaaaaa atataatgag
20761 acaaactata ataaagaaa taatcaaatc tagcggcgta aagtttggta ctagtggagt
20821 tagaggtctt gtttcagcta tgacagataa gatctgttgg ctttatacaa aagcttttat
20881 tcaattccta gagcaaaaat actctattgc taagggtact aaaattgcta tagctcatga
20941 tctacgtgag agtagccta gaataacaac agttgttatt aaagctatca tagatagtgg
21001 tcatgagcca atatactgtg gtgagataccc atcaccagct gtaatgctat atggtatatc
21061 taatcagata ccgtcagtta tggttactgg tagtcatatt ccagaggata gaaatggtat
21121 taagtttaat actccatatg gtgaagttct caaagaagat gaagaaatga ttgttagcca
21181 aactatcagc attgatgaaa gtattttga taaaaatggc atgttttac aaaaactaga
21241 attaccagag cctagtaagc aagcatatac acagtatatt gacaggtatg tagatttttt
21301 ccctaacaac tgtctagcag gtaagactat agggctttat cagcactcat ctgtaggacg
21361 agagatagtc aaagagattc tagagaaact aggtgctaag gttatcttgc tagaattttc
21421 cgaaaaattt gtatctgtag ataccgaggc aattcgccag gaagatgtaa agcttgctaa
21481 gcagtgggca agcaagtata agttgatag tatagtttca actgatggcg atgctgatag
21541 gccactagtt agtgatgagt atggcaattg gctaaaaggt gatattttag gtgtactgac
21601 agctaaatat ctccaagcca atgttatcgt gacaccagta agtagcaata ctgtggcaga
21661 aaagataggt tattttagta acgtgattag aactaaaata ggctcgccgt atgtaattgc
21721 tgcaatgaat gaattactct caaataatca aaatgctgtg gttggatatg aggcaaatgg
21781 aggatttcta ttggctagtg atatttgtaa agatgataaa actctaaaag cgctgcctac
21841 aagagatgct gttataccaa tgttggctgt aatgatgcta tctatcaact ctaataaaac
21901 cgtgtcagag cttttatttg atttgccatc tcgatataca gcaagtagta aaattgatga
21961 ttttgcttcc gagaaaagcc aagaaatctt gaagtcaata ttagcaggtg aatcagatct
22021 tttagataaa attatatcgg agcattttga tggtaaaaat agcattgaaa atatcgatac
22081 tacagatggt gttagagtaa ctttgacaaa tcaagatatt atccatctta gaccatctgg
22141 taatgctcca gagcttaggt gctatacaga ggcagctagt gatgagcagg caaaaagttt
22201 aaatcaatat tgtgtggatt tgattaacaa aaacatttga agatcagtca aaaatattcc
22261 ctaacttttc tcttcaccat tgaaccatta ctaaccttat ctatagctag ccacagataa
22321 aaatgtcatg ctggatttat ttcagcgttt cattataaat atcaatttta ttgagatcct
22381 gaaactagtt caggatgaca g
```

Fig.5.

SEQ ID NO 2
MNYHIKEVFWSIILSFLKSQKGIHTNDEAKLRLFIEAVFYVLRT
GCQWRMLPFYYGKYRSIHKRFKDWCDKDIFSRLFKSVQNPDLQEVMLDSTIARAHACA
TGYDKDDNQAIGRSVGRITTKIHAMTDALGNPIEILLSEDKTHDSKVAIDLLKNVYNT
KVIADRAYHSNEIRQHIQGISSEAVIPCKSNTLNHIPFDSHVYKERHLIENFFSKIKH
FRRVFSRFDKTILAYIGMIKLACTFIWLR

SEQ ID NO 3
MSFYDNRTLNFVVIIVLTIITVNWTFYIFKQDVNLHFLLALVLL
RCLSSFLLLRDYMASWRKSTQKTFLRKAFINLPVFFIVALFFYGKVTFSLIFSEFLFY
VFLISLSVYFYWYLMNRGSVDKSKTAVIYGAGAAGTKIAQELASAGYRIKCFVDDNET
LQKRSIDSKKVLSKAELTKLLLSSRFDLLVIALPRNANQVVKNIYKEFEKDFNQIRIM
PPLEEILQDENFMSQLKPVSLYDLLARDTKSLDKESISNFIKNKVVLVTGAGGSIGSE
IVHQCIKYQAKELILVDHSEFNLYKITEECSHFNINSVLCSVCDRKALAEVFQKYTPN
IVFHAAAYKHVPLVEENISRAIRNNILGTKNAIDLAIEAGVESFILISTDKAVRPTNV
MGATKRVCELYLQNVDPKNTKLAAVRFGNVLGSSGSVIPKFEEQIRKGGPVTVTHPEI
TRYFMLIPEACELVLQAGAIAKNSEVFVLDMGQPVKIIDLAKQFIRLSGRGDIDIKIV
GLRPGEKLYEELLIEEDDVSTDYKDIFIGRRTFYDINTLNQDIESLIKDDVDQLVILK
KIVPEFEHRLNG

SEQ ID NO 4
MFYEVFKRLLDILLSFMGLLLLSPIFLIIIFMIKKDSKGPIFFK
QKRYGKDKQFFYIYKFRTMYVDTPKDMPTHMLQDPSKCITKVGGFLRKSSLDELPQII
NILKGEMSIVGPRPALWNQDDLIAQRDKYGANAVPVGLTGWAQINGRDELPIPDKAKL
DGDYVKNKSTWFDLKCIFLTVFSVFAKKGVVEGGTGALGNKEDLK

SEQ ID NO 5
MKKRILVTGLSSYIGNSFAAKYNSDFSIDKISLRDVSWANIDLS
GYDAVLHVAGIAHTSKDPKLKEKYYKINTQLTYDLAKQAKDQGVRQFVFLSSIIVYGD
SAPIGQQKVITKYTEPKPDDFYGDSKLQTEIKLNSLASDDFNIAIIRPPMVYGEGSKG
NYPKLVKLAKYTFIFPNINNQRSVISIDNLSKEIAEIILQTKHGVFLLQDNEYFCTSQ
FIKNYRKDVLGKRTYLTKIFNPIIRLLAKKVDFINKVFGNLTYEK

SEQ ID NO 6
MRSKLLFIANDFDIVIYRFRREVIESFAAKEYEIVLVTPYSKKA
EVFCKSLGVKYINVDIDRRGKNPFKDLLLLFNYFKIIKKEKPDYIFSYTIKPNLYVGL
VNLFFRKKFYPNVTGLGSVFANHGIVQKFIISLYKLSFKSTTKVFFQNEQNKKLFIAK
KIISGEKSILLPGSGVNLDENKYVDYPKDQGILKFVFLGRIMKEKGIYELLEAFAILE
KKYKNISLDIYGFCDENKSNFMGKVNTIKSVKFYGFTDNTKEKIASAHAVVLPSYHEG
MSNVLLEAAAIGRPVIASDIPGCREIFDDGLSGLSCNPNDVSSLRNSLEQFINMSYTD
KIAMSYKARAKIEKDFDRSIVVNAYLQQN

SEQ ID NO 7
MSLYEDIVAKREKVSLVGLGYVGLPIAIAFAKKIDVLGFDICET
KVQHYKDGFDPTKEVGDEAVRNTTMKFSCDETSLKECKFHIVAVPTPVKADKTPDLTP
IIKASETVGRNLVKGAYVVFESTVYPGVTEDVCVPILEKESGLRSGEDFKVGYSPERI
NPGDKVHRLETIIKVVSGMDEESLDTIAKVYELVVDAGVYRASSIKVAEAAKVIENSQ
RDVNIAFVNELSIIFNQMGIDTLEVLAAAATKWNFLNFKPGLVGGHCIGVDPYYLTYK
AAELGYHSQVILSGRRINDSMGKFVVENLVKKLISADIPVKRARVAIFGFTFKEDCPD
TRNTRVIDMVKELNEYGIEPYIIDPVADKEEAKHEYGLEFDDLSKMVNLDAIIIAVSH
EQFKDITKQQFDRLYAHNSRKIIFDIKGSLDKSEFEKDYIYWRL

Fig.5 (Cont I).

SEQ ID NO 8
VAYDNVKFPHGSFFLVTGGAGFIGSNLCEVLLSKGYRVRCLDDL
SNGHYHNVEPFLTNSNYEFIKGDIRDLDTCMKACEGIDYVLHQAAWGSVPRSIEMPLV
YEDINVKGALNMLEAARQNNVKKFVYASSSSVYGDEPNLPKKEGREGNVLSPYAFTKK
ANEEWARLYTKLYGLDTYGLRYFNVFGRRQDPNGAYAAVIPKFIKQLLNDEAPTINGD
GKQSRDFTYIENVIEANLKACLADSKYAGESFNIAYGGREYLIDLYYNLCDALGKKIE
PNFGPDRAGDIKHSNADISKARNMLGYNPEYDFELGIKHAVEWYLIN

SEQ ID NO 9
VYIKKVSFKILYLYLLAFCIIFSLEFKFAILNIIVYLPACILGF
LALKKLFVGNIVKKQLAFLFFFFFLSMIYLIIVQIILLDAASLFPQFLFNILIAIGFC
NFIFVSYDNNENYFFNMSKIIFFVTFLQSIFVFLSRYYIFLNDWIFFFLVKKGNIEIS
NVIEYKLRVFGLSNAGGDGLGFSITIGLCFSIFYFIKYIKGKSIFTKLMLFVPLILIV
FSNIFISRTSLLTSSLILLITIFYIYIKKEKLLFIIILALFFLSIWILFKLNLNLSWA
FENIYSYIQSGDFSHGSLSVLINKMLFVPDNLLTWIFGCEDVSNTDIGYIKYLYYGI
IFSMFFYILIIFLYFEMRKCFIFSEYRSLFLLLLIVCLVFQAKIIFLTVGLFTKLTII
LFIFSLKENSFTTRSVI

SEQ ID NO 10
LKRFVHLIINLNQGGAETMLYKLCKSMDKSIYHITIISLMGRGV
FANKLEAYGVKVYTLNLNKFNVLFVLFKYIKIIRRIKPDVIHAWMYHANVISILCKPF
YRKTKYINSIRMGLENYDGHKNLTKFMIKLNAKFSKFSDLTLNNSKKSLEDHQNIGFK
NQCFIANGFDKDVFKPSFLKYEKFRLNNDLDDNVKIIGIIARNHADKNISRFLQIANL
LLKSNPSLRFLIAGRECSKIDIGSYLDNKSNVNKFFVFESVDSSEYLPVLDLYLSTSK
VEGFPNILAEAMLCEVPIVASNVGDCKDILNGYGEVFELSQGNKEIIEKIMKVLETTV
VMKKRMREYIINNFSIEAILEKHEKLYHEGSV

SEQ ID NO 11
MCGVVGFYSFNKEEGFDSIINQSLLSIKHRGSDDSGYWCDNQVT
LGHTRLSIHDITNAGHQPMLSNSGNTAIVFNGEIYNYLSIKNQLLSEYSNLKFKSNSD
TEVLVNAIELWGIDKTLEKCIGMEAFGVYSRKTSCLILARDREFGEKPLYFGIQNGILG
FASELKALKPLKECGWRFDIDRDALATYMRYAYVPTPYSIYKNISKLNVGSYIKFDAK
GNSKEYKYWDSKKVLDSEKYKDSYDQAILDLEIKLKSTLSIQMQSDVPLGAFLSGGID
STTVVALMQSMSKDKINTFSIGFNQKEYNEAEHARAVAKHIGTNHTDMYVTERDALDV
IPKLAGIYDEPFADSSQIPTYLVSKIAKSKVTVALSGDAGDELFGGYNRYFLAPNIAK
KIKFAKLLKYAPDAWIKKAEILNFGKFALLADKLLKLKRVLEKAKTNKELYVLLCSQI
NDTSFVLGAKEYDILRDKNIYDIPQLSFQEWMMFVDSNTYMIDDILVKVDRAAMANSL
ETRVPFLDHNIYEFAYSLPIDYKIQRGNGKRILKDLLYKYVPESLVNRSKMGFGIPLA
KWLREDLREWADNLLDYSKIDKQGYLSPEVVQKYWQEHLSGKRNWQAILWNILIFQEW
LDNE

SEQ ID NO 12
MSKVNVTKPYLPDINKYKSYVNKIYKNGWLTNNGPLVQELEKRL
AKYLGVKNIVLVSNGTIALEIAYRALGVKGSAITTPFSFVATTSSLVSNNVKPVFVDI
DENTLSIDVSKIKYAIEEDTSAIVPVHVFGNGCEVEKIDMLAKKHNLKVIYDAAHAFD
VKYKGESILNYGDISTLSFHATKIFHSIEGGALIINDDSLVEKVRYFINFGIESSESI
PYLGTNAKMNEFEAAMGLCVLDDIIEIKSKRKVITEIYEAGLDGLVKFQEQNQHSSRN
YSYFPVIFRTEEELLRVQKALIQNDIISRRYFYPSLDSLSYIEPKQYMPISRDISKRI
LCLPIYAELEDDKINKIINNIKEVSS

SEQ ID NO 13
MKKIFVVTDNRTILSDFKNIIGSKNDVQVDYFCSFKSQTSFAKE
IYNSEIKPIDMKKNGNDLIGKYDLGFSCHSKQLFPAKLVNSVLCINIHPGLNPYNRGW
FPQVFSIINKLPIGATIHVMDEEIDHGDIIIQEEVEVNSFENSFDVYAKVQKKEVELF
TKVIDDILNNKFTRIKPNSEGNYNSIHDYKNMCEIDLDKIVTMREAIDYLRAMTHPPY
KNSYFIDEHGNKVFVALELEKIS

Fig.5 (Cont II).

SEQ ID NO 14  MSLKKNTISNYITQLYTSLIGIVILPLYLQHLSHDAFGLIGFFT
VFQTWLRLLDVGITPTLSREVAHVRGSTDDYHYLRKLVRSLELFFIIVGVLVFIVIST
HSRYISTSWLHIGSLDADSVSVCIALMGLMFALRWVSDLYGGGLRGFERQVLYNNLSI
IQTTLQFIGGLLFICYVSTNIMYYFVYQTIIAILYLVCIAIAFYKILPSSFSVGLRFD
FKIIRKVLPFALGIAYSTTVWIIVTQSDKLVFSHVLPLSEYGYLSLLIVISSAVTILS
SPISIAIQPRMTMLLAQQNVKGMESLYLKSSLISITFLSAVVTCVLMYSHQLLQSWTG
SMEIANWGSNILNIYVLSASIICIISFQYFLQYAYGKLKLHNTYNTISLVFFAPIVIY
TAYNYGVYTTALLWLGYAIVGLIIWMPIVHHVFAKGINRYFFINLAVITIVCFLLSLI
FKGWYIYPSKIGLVELILIGFAFLFIQICIEYVLFRYKVLRCIDD

SEQ ID NO 15  MIKVSVCVMTYNQEKYIGQCLESLVTQETDFDFEIIVGDDFSTD
GTRDVIQEYQKKYPDIIKPVFRDKNVGITENIKEIYFVANGEYIAHMDGDDYALPGKL
QIQADFLDNNPRCTGVFHNINILYPNGNIQHSRFACSNKSIFNLSDTLRGVAVGANSS
KMFRTSVLDDLILPDIELLDYYFHVITAEKGYLSFLNSNESYSVYRKGIGITSKSKEK
IYNTYAGLFEYFLDRYPEEKLNICIPVVQMIISAIKGRCFISAIRLFKILIRSRCIPL
VSWFKYRFEK

SEQ ID NO 16  MKGIILAGGSGTRLYPLTLGVSKQLLPVYDKPLLYYPLSVLMLA
GIREILIISTVRDISLIQELLGDGSQFGIQLSYKIQPSPDGLAQAFILGEEFLAGDSA
CLILGDNIYYGQGMTTMLESARAQCGGPAGGACVFGYYVNDPHRYGIVEFDKQKNVIS
VEEKPQNPKSHYAITGLYFYDNNVVEYAKQVKPSARGELEITSLNELYLKENKLNVEL
LGRGFAWLDAGTHDSLLEAGQYVATIEKRQGLKIACLEEIAWRKGFISTQQVLAQAEK
LSKTEYGQYLKNLIKDGL

SEQ ID NO 17  MTSHYRNDDVMRNEKMNYKPKNILVTGAAGFIGSNYVRMMLSRY
SDIKIISYDKLTYAGSLDNLKDLNNEHNHTFIKGDICDEVLVYQTLKEYKIDTIVHFA
AESHVDNSIANPKVFLETNVIGTFTLLDCAKRYWLDELGLEETSCRFHHVSTDEVYGT
LAKDEPAFTEIKAYEPNSPYSASKAGSDHISRAYHHTYKLPVTISNCSNNYGPYQHRE
KLIPVVINSCINYKPIPVYGDGSNIRDWLYVEDHCDAIQTIVEKGVVGEVYNIGGINE
VDNLTLVKTICKLMDEYKPENAPHSNLITFVEDRKGHDWRYAIDNSKIQNELGWKPSQ
DFDKMFRQTIEFYL

SEQ ID NO 18  MPSYSQDFRDIVINKHEEGMTEFELSKFFNIDKRTVVSWIEFYK
RTGDYSSKQGVGCGRVASFTDKTLIEQYLIDHPDASALDIKEALAPDIPRSTFYDCLN
RLGFSFKKRLQNISKEKNMKGWSI

SEQ ID NO 19  MITPIILSGGFGSRLWPLSREASPKQFIGLVDEHSLLENTIKRL
DNVKDITSPVVVCNESHRFQVAEVLRKINKKGDILLEPLARNTAPAIALAALHLAIND
PNTIMLVLAADHHIENLEIFHQAIEKAQQKVIKDDSLVTFGITPTCPHEGYGYIKQGV
QTTVNGVYKVDKFVEKPSVVVAQEYLDSGKYYWNSGMFMFTARVYLEVLEKLQPEIYR
GCEKTYQKSQQDLDFVRFDKQSFALVQSQSIDYAVMEKATNVAIVPMQQSGWSDVGSW
DSLYDIAAKDSCGNVVIGDVITSNVKNSYLRSHDRLLAAVGVNDLIIVETADAILVAD
KNKTQDVKKIVEVLKIQQRSELLQHKQIYKPWGSATILEDKSGYKIQAIQLEPGKKLS
LQQHYHRSEHWIVISGTATVTIGTTKSIVRPNESVYIKIGESHRLENNGKIPVILIEV
QVGEYISEDDIVRLDTSS

Fig.5 (Cont III).

SEQ ID NO 20  MRQTIIKEIIKSSGVKFGTSGVRGLVSAMTDKICWLYTKAFIQF
LEQKYSIAKGTKIAIAHDLRESSPRITTVVIKAIIDSGHEPIYCGEIPSPAVMLYGIS
NQIPSVMVTGSHIPEDRNGIKFNTPYGEVLKEDEEMIVSQTISIDESIFDKNGMFLQK
LELPEPSKQAYTQYIDRYVDFFPNNCLAGKTIGLYQHSSVGREIVKEILEKLGAKVIL
LEFSEKFVSVDTEAIRQEDVKLAKQWASKYKVDSIVSTDGDADRPLVSDEYGNWLKGD
ILGVLTAKYLQANVIVTPVSSNTVAEKIGYFSNVIRTKIGSPYVIAAMNELLSNNQNA
VVGYEANGGFLLASDICKDDKTLKALPTRDAVIPMLAVMMLSINSNKTVSELLFDLPS
RYTASSKIDDFASEKSQEILKSILAGESDLLDKIISEHFDGKNSIENIDTTDGVRVTL
TNQDIIHLRPSGNAPELRCYTEAASDEQAKSLNQYCVDLINKNI

Fig.6.

SEQ ID NO 1
atatttattttttgtgcacagaacctaatttgcattttttgtgcacaaagaaaattttttg
atataatagactttaataggatatttctaaaaattaacaaatgtcttctacgataata
gaacgcttaatttcgtggtaataatagttttaactattattactgttaattggactttct
atattttcaagcaagatgttaatttacattttttacttgcattagttttgctgagatgct
tgtcatcttttttactacttagagattatatggctagttggcgtaagtcgactcaaaaaa
cttttttacgtaaggcttttattaatttgccagtattttcatagtggcattattttttt
atggcaaagtcacttttttcgttgatattctctgagttttttattttatgtttttttgatca
gtttaagtgtctacttttattggtatttgatgaacagaggatcagtggataaaagtaaaa
ctgcggttatttatggtgcaggtgctgcaggaacaaagattgctcaagaacttgcttctg
ctggttatcgcatcaaatgttttgttgatgacaatgaaactttacaaaaaagaagtattg
atagtaaaaaggttctatctaaagctgaattaacaaaactattgctatctagtagatttg
accttttggttattgcattgccaagaaatgcaaaccaagtagtcaaaaatatatataaag
aatttgaaaaggatttttaatcagattagaattatgccgcctcttgaggaaattcttcaag
atgagaatttttatgtcacagttgaagcctgtttcactctatgatctattagcgcgtgata
ctaagagtttagataaagaatctatctctaatttttatcaaaaataaggtggtgctagtca
caggagctggaggtagtataggttctgaaatagtacatcaatgtatcaagtatcaggcaa
aagagttgatattggttgatcatagtgagtttaacttatataaaattactgaggagtgta
gtcattttaatatcaatagtgtgctatgttctgtttgtgatagaaaagcattggctgagg
ttttcaaaagtatactccaaatatagtatttcatgctgctgcctacaagcatgttccct
tagttgaggagaatatctctagagcaattagaaataatatcttaggtactaagaatgcta
tagatctggctatagaagctggtgttgagtcatttatattgatttccactgataaagcag
tgcgaccaacgaatgttatgggggctaccaagagagtttgtgagctgtatttacagaatg
ttgatcccaaaaataccaagcttgctgcagtgcgttttggtaatgtgcttggtagtagtg
gcagtgtgattccaaaatttgaagagcaaataagaaaggtggtcctgttacagttactc
atcctgaaattacacgttattttatgttgataccagaagcttgtgaactggtcctacaag
ctggtgctattgcaaaaaattcagaggtctttgtcttagatatggggcaacctgtcaaga
ttattgatcttgctaaacaatttattagactttctggtagaggtgatattgatattaaaa
tagttggtttgcgtccaggagagaaactttacgaagagcttttgatagaggaagatgatg
ttagtaccgactataaagatatttttattggtagaaggacttttacgatattaatactc
taaaccaagatattgaatcgttgatcaaggatgatgttgatcagcttgtgatattaaaga
aaattgttccggaatttgaacatagattgaatgggtagtggttttatgttttatgaggtt
tttaaaagattgcttgatattttacttcttttatggggttgttgttattaagtcctatt
ttcttaattattattttttatgataaagaaagattcaaaaggacctatatttttaaacaa
aagcgctatggtaaagataagcaatttttttacatatataagtttagaactatgtatgtt
gatactccaaaagatatgccaacgcacatgttacaggatccatcgaaatgtataactaag
gttggaggattttttaaggaaatcatctttagatgagttgccacaaattataaatattcta
aaaggtgaaatgagcatcgtgggtccaagaccagcattatggaatcaagatgacttaata
gcacaaagagataagtatggggcaaatgctgtgcctgtgggactgactggctgggcacag
attaatggtagggatgaattaccaatacctgataaagctaaacttgatggtgattatgta
aaaaataaaagtacatggtttgatttaaaatgtatttttttgacagtatttctgttttt
gccaaaaagggcgtcgttgagggtggtactggagctttaggtaacaagaggatttaaag
tagtatgaaaaaagaatcttagttacaggtttgagtagctatattggtaactcatttgc
ggctaaatataactcagatttagtatcgataaaatatctttgcgcgatgtttcgtgggc
aaatatagacttaagtggttatgatgctgtattgcatgtcgctggaattgcccatacttc
aaaggatcctaaactaaaagaaaaatactataaaataaatacgcaattaacttatgatct
ggcaaaacaagctaaagatcaaggtgttcgacagtttgtgttttaagtagtattatagt
ttatggtgatagtgcgccaataggtcaacaaaagttataactaaatataccgaacctaa
accagatgatttttatggagatagtaagcttcaaactgaaattaagctaaatagcctggc
tagtgatgactttaatattgctataatcagaccaccaatggtatatggagaaggctcaaa
aggcaactatccaaagttggttaaacttgcaaagtatacttttattttttcctaatattaa
taaccaaagaagtgttatatctatagataatttatctaaagagattgcagaaataattt
gcaaactaaacatggagttttctacttcaagataatgaatatttttgcacttcacagtt

Fig.6 (Cont I).

```
tataaaaaactatagaaaagatgttttaggtaagagaacttatctgacaaaaattttta
tccaattataagattgcttgctaaaaaagtagattttattaataaagttttgggaattt
gacttatgagaagtaagttattattcatagctaatgatttgatattgtaatatatcgtt
tcagaagagaagtaatcgagtcttttgctgctaaagagtatgagatagtactagtaacac
catattctaagaaagcagaggttttttgtaaaagtcttggtgttaagtatataaatgttg
atatagatagacgaggcaaaaatcctttaaggatttgcttctttattaactattttca
aaataataaaaaagaaaaacctgattacatttttagctatacaattaaaccaaatttgt
atgttgggttagtgaatttgttttttaggaagaagttttatccaaatgtaacaggcttag
gaagtgtttttgctaatcatggtattgttcagaagtttataatatctttatataagttat
catttaaaagcaccacaaaagtattctttcagaatgagcaaaataaaaagttatttatag
ctaagaaaataatcagtggagaaaaatcaatattattaccaggttctggggtaaacttag
atgaaaataaatatgttgactatcctaaagaccaaggaatattaaaattcgttttttcttg
gccgaataatgaaagaaaaggggatttatgaattgttagaagcctttgctatacttgaga
aaaaatataaaaatattagtcttgacatttatggttttttgtgatgaaaataaatctaatt
ttatgggaaaggttaatacgataaaatcagtaaaattttatggttttactgataatacta
aagaaaaaatagctagtgcacatgcagttgttttgccatcttaccatgaaggaatgtcaa
atgtgctgttagaagcagctgcgataggtagacctgtaattgcgtcagatattcctggt
gtagagaaattttttgatgatggtctctctggcttatcatgtaaccctaatgatgtgagtt
ctttacgtaactcattagagcagtttataaatatgtcgtatactgataaaatagctatga
gctataaagctagagctaagatagaaaaagattttgatagaagtattgttgtcaatgcat
acttacagcaaaattaataataagggtttaaattatgagtttatatgaggatatagtcgc
taaaagagaaaaggtttcattggttggcttgggttatgttggtttaccaatagctattgc
atttgcaaaaaaatagatgtgttaggatttgatatttgtgaaacaaaagttcaacatta
taaggatggttttgatccaacaaaagaagtaggagatgaggctgtcagaaatacgacaat
gaaatttagttgtgatgaaacaagtcttaaagagtgtaaatttcatattgttgcagttcc
tacaccagttaaagcagataaaactcctgatttgacgccgattattaaggcaagtgagac
ggttggtaggaatcttgtcaaggcgcttatgttgtgtttgaatcaactgtttatcctgg
tgttacagaagatgtttgcgtaccaatacttgaaaaagagtctggcttgaggtctggtga
agatttcaaagttggttactctcctgagaggataaatcctggtgataaggttcataggtt
agaaacaattatcaaagtagtatctggtatggatgaagagtctttagatactatagcaaa
agtttatgagctagtagtagacgcaggagtttatagagctagtagtataaaagtggctga
agctgctaaggttatagaaaactctcaaagagatgttaatatagcttttgttaatgagtt
atcgataatatttaatcagatgggtattgatactctagaggttttagcagcagctgcaac
taaatggaatttcttaaactttaagcctggtcttgttggtggacattgtattggtgttga
cccatattacctaacgtacaaggcagctgagcttggatatcattctcaggtaatattatc
tggtcgtaggataaatgatagtatgggtaaatttgtagttgagaatttagtcaaaaaact
gatatctgcagatatacctgttaagcgagctagagtagcaattttcggcttacttttaa
agaagactgtcctgacactaggaatactcgagttatagatatggtaaaagagctcaacga
gtatggtatagagccatatattatagatccggtagctgataaagaagaggctaaacatga
gtatggacttgagtttgatgatctaagtaaaatggtcaatctagatgcgatcattattgc
tgttagtcacgaacagtttaaagatataacaaagcaacagtttgataggctatatgcgca
taattctagaaagattatatttgacatcaaaggtagtttagataaatctgagtttgaaaa
agattatatttattggagattgtagtggcttacgataatgttaaatttcctcatggttcg
ttttttttggtgactggaggtgcgggttttattggctctaatttatgtgaagttttactt
agtaagggttatagagttaggtgtttagatgatctctcaaatggtcactatcacaatgtt
gagccgttttttaactaattctaattatgagtttataaaggtgatattagagatttagat
acttgcatgaaagcttgtgaaggtattgattatgttctacatcaagctgcttggggaagc
gtaccaagaagtattgagatgccattagtgtatgaagatataaatgttaaaggtgcatta
aatatgcttgaagcggctagacaaaataacgttaaaaaatttgtctatgcttctagttca
tcagtatatggtgatgagccaaatttacctaaaaaagaaggtagagaaggaaatgtttta
tcaccctatgcatttacaaagaaagctaatgaagagtgggcgagactatacacaaagtta
tatggtctagatacttatggtctaagatattttaatgttttcggtagaagacaagatcct
aatggtgcgtatgcagcagttatacctaaatttatcaaacagttattaaatgatgaagcg
ccaactataaatggagatggtaaacagtcgagagattttacatatatagagaatgttatt
gaggcaaatcttaaagcatgtttagcagatagtaagtatgccggagagtcttttaatata
```

Fig.6 (Cont II).

```
gcttatggaggtagagagtatcttatagatttgtactataatctttgtgatgccttgggt
aaaaaaatagagccaaattttggtccagatagagcgggtgatattaagcatagtaatgct
gatatttcgaaggctaggaatatgctcggatataatccggaatatgattttgaattaggc
ataaagcatgctgttgagtggtatttaattaattaaatggtattttaatcaagtgtacat
aaaaaaagtgtcttttaaaattttatatttatatttactagcttttgtattattttag
tttagaatttaaattttgctatattgaatattatagtttatcttccggcttgtatttggg
tttttagctcttaaaaaactatttgtcggaaatattgttaagaaacaattagctttcct
ttttttctttttcttttttatcaatgatttatttaataatagtccaaataatcttacttga
tgcagcatcattgtttcctcagtttttatttaacattttgatcgcgataggttttgtaa
ctttattttgtttcatatgataataatgaaaattatttttttaatatgtctaaaataat
atttttgttactttcttacaatctattttgtatttctttcaaggtattatatattttt
aaatgattggatattctttttttagtgaaaaaagggaatattgagatttcgaatgttat
tgaatataagttaagagtattcggacttagtaacgctggaggggatggtttaggattttc
aattactataggattatgttttctatatttatttcaaatatattaaaggtaaatc
tatatttaccaaacttatgctgtttgtaccttaattcttattgtgttttctaatatttt
catatctagaacatcactcttaacttcttcacttatattgttaataacaatatttatat
atatattaaaaagaaaaattactgtttattataatattggcgctattctttttatcaat
atggatattgttcaaattaaatttgaatttgagttgggcttttgaaaatatttactcgta
cattcaatctggcgattttcacatggaagtctaagtgttaatcaataaaatgctttt
tgtgccagataacctttgacttggatatttggttgtgaggatgttagtaatactgatat
tggttatattaaatatttatactattatgggattatattagtatgttttttatattct
tattattttcttgtactttgaaatgagaaaatgttttatatttcagagtatcgatcatt
atttctattgttgttaatagtatgtttagttttcaagcaaaaataatttttttgacagt
aggattatttactaaattaaccattatattatttattttttctcttaaagaaaacagctt
tacaactaggagtgtgatttgaaaaggtttgtacatttaataataaaccttaaccaaggt
ggtgctgaaacaatgctttataaactttgcaaatctatggataagtcaatatatcatat
acgattatatcacttatgggtaggggagtatttgcaaataagttagaagcttatggtgtt
aaagtttatacattaaatttaaataaatttaatgtactatttgtattgtttaaatatatt
aagattatcagaagaataaagcctgatgttattcatgcttggatgtatcatgcaaatgta
atttctatattatgcaagccttttatagaaagactaaatatataaatagtataagaatg
ggattggagaattatgatggtcataagaatcttacaaagtttatgataaagttgaatgca
aaattttctaagttctcagatttaacattaaataattcaaagaaatcattagaagatcat
caaaatataggttttaaaaaccaatgctttatagcaaatggttttgataaagatgttttt
aaaccgagcttttaaagtatgaaaaattcgtttaaataatgatttagatgataatgtt
aaaattataggtatcatagcaagaaatcatgctgataaaaatatttctcgtttcttacaa
atagctaatttattgttaaaaagtaatcctagtttacggttttttaattgctggaagagag
tgttcgaaaatagatataggtagttatctagataacaaaagtaatgtaaataagttttt
gtatttgaatctgtggattctagtgaatacttaccagtattagatttatatttgtctaca
tcaaaagttgaaggttttccaaatatacttgcagaagccatgctatgtgaagttcctatt
gttgcttctaatgttggagattgtaaagatatacttaatggatacggtgaagttttgag
cttagtcaaggtaataaagaaataatagaaagattatgaaagttttagaaacaacggta
gtcatgaaaaagcgcatgagagaatatataataaataattttagtatagaagctattttg
gaaaaacacgaaaaactttatcatgagggcagtgtctaatgtgtggagtagtaggctttt
actcatttaataaagaagaaggttttgactcaataattaatcaatcattgctttctataa
agcatagagggtcggatgatagtgggtattggtgcgacaatcaagttactctggggcata
ctagattatcaatacacgatataactaatgcgggacatcagccaatgttatctaatagcg
gtaatactgctattgtgtttaatggagaaatatataattacttatccataaaaaatcagc
tattaagtgaatattcaaatcttaaatttaaaagtaacagtgatactgaggttttggtca
atgctattgaactttggggtatagataaaactttagaaaaatgcataggaatgtttgctt
ttggagtttacagtagaaaaactagttgcttaatactagctagagatagatttggcgaga
agccattatattttggtatccaaaatggtatttgggttttgcatcagaattgaaggcac
ttaagccattaaaggaatgtggctggaggtttgatatagatagagatgctttagcaacat
atatgaggtatgcttatgtaccaacaccatactctatttataaaaatatatctaaactaa
atgtaggtagttacataaaatttgatgctaaaggtaatagtaaagagtataaatattggg
attctaaaaaagtactagattcagaaaaatataaagattcgtatgatcaagcaatcctag
```

Fig.6 (Cont III).

```
atttagaaattaagcttaaaagtacactatcaatacaaatgcagtcagatgttcctctag
gagcattttatccggaggaattgactcaacaactgtagttgctcttatgcaaagtatgt
ctaaagataagataaacacttttagtataggttttaatcaaaaagaatataatgaagctg
agcatgcaagagcagtagcaaaacatataggtacaaaccacacagatatgtatgttacag
aaagagatgctcttgatgtaataccaaaacttgctggaatatatgacgagcccttttgctg
attcatcacaaataccaacgtatcttgtgagtaaaatagctaagtcgaaagtaacagttg
cactatcaggtgacgctggtgatgagctctttggcggttataatagatacttttttagcac
caaatattgctaaaaaaatcaaatttgctaagttacttaaatatgcaccagatgcttgga
taaaaaagctgagatattaaattttggtaagttcgctttattagcagataaactactaa
aactaaaaagagttctcgaaaaagcaaaaacaaataaagagctttatgtactactttgtt
cacaaataaatgatactagctttgtgttaggagcaaaagagtatgatatattaagagata
agaatatttatgatattccacaattatctttccaagagtggatgatgtttgttgattcta
atacatatatgatagatgatatattggttaaggttgatagagcagctatggctaactctc
tagagacaagagtgccatttttagatcataatatttatgaatttgcttattccttaccaa
ttgactataaaatacaacgaggtaacggaaaaagaatttttgaaagatttgttatataaat
atgtgccagaaagtttggtcaataggtctaagatggggtttggtattccgcttgctaaat
ggttaagagaagatttacgagagtgggcagataatttactggattatagtaaaatagaca
agcaaggttacttaagtcctgaggtggtgcaaaaatattggcaagagcatttgagtggta
aaagaaattggcaagcaatattatggaatattctaattttcaggagtggttagataatg
agtaaagtaaatgtaacaaaaccatacttaccagatataaataaatataaaagctatgta
aataaaatatacaaaaatggatggcttactaataatggtccgttagtgcaagagctagaa
aaaagacttgcaaagtatctaggtgttaaaaatatagttttagtatcaaatggtacaatt
gcattagaaatcgcgtatagagcgttaggagtcaaaggaagtgcaattactactccattt
tcatttgttgctactacatcttcattggtttctaacaatgtaaaaccagtgtttgttgat
attgatgagaatactctaagtatagacgtctctaaaattaagtatgctattgaagaggat
acttcagctattgtgccagttcatgtgtttggaaatggttgtgaagttgaaaaaatagac
atgctggctaaaaaacataacttaaaagttatttatgatgcagcacatgcttttgatgtt
aagtataagggtgagagtatattaaactatggtgatatttcgacattaagttttcatgca
acaaagatttttcattctattgaaggaggtgcgcttatcattaatgatgatagtcttgtt
gaaaaagttcgttatttcattaattttggtatagaaagctcagaatcaataccttactta
ggtactaatgctaaaatgaatgaatttgaggcggctatgggactttgtgttctagatgat
attatagaaattaagagcaaaaggaaagttattacagagatatatgaggctgggttagat
ggattggtaaagtttcaagaacagaatcagcattctagtaggaattatagctattttcca
gtaatatttaggactgaggaggaacttctcagagtacagaaagcactaatacaaaatgat
ataatatcgcgtagatatttttatccatcattagatagtcttagttatatagagccaaag
cagtatatgccaatctcaagagatatatctaaaagaatattatgtttgccaatttatgca
gagttagaagacgataaaattaataaaataattaataatatcaaagaggtttcctcatga
aaaaaatatttgttgttacagataatagaactattctaagtgattttaaaaatatcattg
gtagtaaaaatgatgtacaggttgattattttgtagtttcaagagtcaaacttcttttg
ccaaagaaatatataacagtgagattaagccaatagatatgaaaaaaatggcaatgatc
ttattggtaagtatgatttaggttttttcttgtcattcgaaacaattatttccagcaaaat
tagttaattcagtattatgtataaatattcatcctggacttaatccatataatagagggt
ggtttccacaggtcttctctattataaataaactacctataggagcaactattcatgtga
tggatgaagagatagatcatggagatataatcattcaggaagaagttgaagttaattctt
tcgaaaactcttttgatgtttatgctaaagttcaaaaaaagaagttgagttgttcacta
aagtcatagatgatattttgaataataagttcactcgaatcaaacctaactccgaaggca
actataattcaattcatgattataaaaacatgtgtgaaattgatttagataaaatagtaa
caatgcgggaagcaattgactatctaagggctatgacacacctccatataaaaatagtt
atttcattgatgagcatggaaataaagtatttgttgctcttgaacttgaaaagataagtt
agaaaatgagccttaaaaaaaatacaatatcaaattatataacacaactatatactagc
ttaattggtattgttatacttcctttgtatttacaacatttaagtcatgatgcatttggt
ctgattggttttttttacagttttttcaaacgtggttacggttgttggatgttggtataaca
ccaactttatcaagagaagtggctcatgttagaggtagtactgatgactatcattactta
cgcaagttggttagatcgttagagctatttttcattattgttggtgttctggtatttatt
gtaattagtacacattcaaggtatatatccacctcttggttacatataggctcgctagat
```

Fig.6 (Cont IV).

```
gctgatagtgtaagtgtatgtattgcacttatgggtttaatgtttgcattaagatgggtg
tctgatctatatggtggtggtttgcgtggctttgaaagacaggttctttataataattta
agtatcatacaaacgacactacagtttattggtggattattatttatctgctatgtgtct
actaatattatgtattattttgtatatcagacaataattgcgatactatatctagtatgt
attgcaattgcattttataaaatactaccatcatcatttagcgtgggtttaaggtttgat
tttaaaataattagaaaagtgcttccatttgcactaggcattgcatattctacaacagtt
tggattattgtcactcaatctgataaattagtgttctcacatgtattaccattatctgag
tatggttatttatctttattgatagtgatatctagtgctgttacgatattgtcctctccg
attagcatagctattcagcctagaatgacaatgctattagcccaacaaatgtaaaagga
atggaaagcttatatttaaaatcatccttgatctcaattactttttatctgctgtagta
acatgtgttttgatgtattctcatcagctgttgcagtcatggacaggaagtatggaaatt
gctaattggggtagtaatatcttaaatatatatgttttatcagcatctattatttgtata
atatcatttcaatatttttacagtatgcttatggtaagttaaagctacataatacatat
aatacaattagtttagtattttttgctcctatagttatatatactgcttataattatgga
gtgtatactacagcactattatggcttggatatgctatagtggggctgataatctggatg
cctattgtacaccatgtatttgctaaaggtatcaataggtatttttttataaatttagca
gttattactatagtatgttttttattatcgttaatatttaagggttggtatatttatcca
agtaaaattgggttggtagaattaatattgattgggtttgcattttatttatacaaatt
tgtatagagtatgttttgtttcggtacaaggttttgaggtgtatagatgattaaagtttc
agtatgtgtgatgacatacaatcaagaaaagtatattggtcaatgtttagagtctttggt
tactcaagagactgattttgactttgagataatcgttggagatgattttctacagatgg
tacaagagatgttattcaagagtatcaaaaaaagtatccggatatcataaagccagtttt
tagagataagaatgtgggaattactgaaaatattaaagaaatctattttgttgcaaatgg
tgagtatatagctcatatggatggtgatgattatgcattgcctggtaaacttcaaattca
ggctgattttttggataataatccaagatgtacgggagtttttcataatataaatatact
ctatccaaatggtaatatacaacatagtaggtttgcttgttcaaataagagtatattcaa
tttatcagacactttacgcggagttgctgttggtgcaaatagttcaaaaatgttcagaac
atcggttttggatgatttgattttaccggatatagagcttctagattattattttcatgt
tataacagcagaaaaggttatttaagttttttaaattctaatgaatcctatagtgtgta
cagaaaaggtattggtatcacatctaagtctaaggaaaaaatctataatacttatgctgg
attatttgaatattttttggatagatatcctgaagagaaattaaatatttgtatccctgt
tgtgcaaatgataatttcggctattaaagggagatgttttattagtgctattcgtctatt
caaaattttaattagatcaagatgtattccattagtaagttggtttaaatatagatttga
aaaatataatcatttagaggattatgtgaaatgaagggaataattctagctggtggcag
tggtacaaggctatatccacttaccttgggtgttagcaaacagctgctacctgtttatga
caagccattgttatactatccactatctgtgcttatgcttgcaggtattagggagatatt
aattatctctacagtgcgtgatatctcacttatccaagagcttcttggtgatggttcaca
atttggtatacagttgagttataaaatccagccatcaccagatgggcttgctcaagcatt
tattcttggtgaggagttttggcgggtgactcagcttgtttgatattaggagataatat
ctactatggtcaaggtatgactacaatgctagagtctgcaagagcacagtgtggaggtcc
agctggtggcgcttgtgtttttggttattatgttaatgatccgcatagatatggtatagt
cgaatttgataagcaaaaaatgtaatttcggtagaggaaaagccacagaatcctaagtc
acactatgctatcacaggtttatatttttatgataataatgttgttgagtatgctaaaca
agtcaaaccatctgcacgtggtgagctagagattacttcacttaatgagttatatctaaa
agaaaataagctaaatgtcgaactcttagggcgtggctttgcttggcttgatgctggtac
gcatgattcattgctagaggcaggtcaatatgtcgcaactattgagaaaagacaagggct
taaaattgcatgtttggaagaaattgcatggcgtaaaggctttatctcaacacaacaagt
tctagctcaagctgaaaaactttctaagacagagtatggtcagtatctgaagaatttaat
taaggatggtttataaattaatccgtcatacccatgaaggtgggtatctcataaaagttg
gatatgttttggagattccaatctgcgcagtaatgacaggtttggtaatatatagcgatg
ttttacaatgactaaaaatggttttatgtatattcttacaaataaggataatactgttct
gtacatagttgtaacatctaatttgataaaaagaatgtatgagcataaacatagccttgc
agatggttttactaaaaatataatgttaataagttagtttatttttgaaatttatgaagat
ataaaagcagcaattctgtgagaaaagcagttgaaaaaatgaaacagatcttggaaagaa
cgaattattaatgagatgaatccgaattggaatgatttatatgaattaatatgtgagtaa
```

Fig.6 (Cont V).

aacttttgtcttactggtgcagataggtatctctaaatatcagatgtgattgggagatta
ccgcctacgcggtaatgacaagtttatgcggtaatgatagtttagtgagagaatgactag
tcactataggaatgatgatgtaatgaggaatgaaaaaatgaactacaaaccaaaaaatat
cctagtaacaggtgcggcgggatttattggtagtaactatgtgcgtatgatgttatcacg
ctatagtgatatcaaaataatctcgtatgataagcttacttatgcgggtagtttagataa
tctaaaagacttgaataatgaacataaccatactttataaaaggtgatatttgtgatga
agttttagtatatcaaacactgaaagaatataaaattgatacgatagtacattttgctgc
agaatcgcatgttgataattcaattgctaatccaaaggtattttagaaacgaatgtgat
aggtacatttacactttagattgtgctaaaaggtattggttagatgagctaggtttaga
agaaactagttgtaggtttcatcatgtatctactgatgaggtatatggtaccttggcaaa
agatgaaccagccttactgagattaaggcttatgagccaaattcaccgtattcggcatc
taaggcgggatctgatcatatttctagagcatatcatcatacctataaacttccggtaac
aatttcaaattgttcaaacaactatggaccataccaacatcgagagaaattaatccctgt
agtgataaatagttgtataaactacaagcctattcctgtttacggagatggttcgaatat
tcgagattggctatatgtagaagatcactgcgatgctatccagacaattgttgagaaagg
agtggttggagaggtttataatattggtggtattaatgaagttgataatctaaccttggt
aaaaactatctgtaaactaatggatgaatataaaccagaaatgctccacattctaactt
aatcacatttgtggaagatagaaaggacatgattggcgttatgctattgataacagcaa
gattcagaatgagttaggatggaagccatcacaagatttgataagatgtttagacaaac
tattgagttttatctatagcttaaatatttatcttatgagtatctctaaaaaatcaattt
aatttattttttgtgttaaaaagtagtgttcgcaagaatatagttaatccgaaagatattt
gtagaaaagatatttgtagaaatgttataatgtctaataaaa

SEQUENCE LISTING

<160> NUMBER OF SEQ ID NOS: 41

<210> SEQ ID NO 1
<211> LENGTH: 17623

```
<212> TYPE: DNA
<213> ORGANISM: Francisella tularensis

<400> SEQUENCE: 1
atatttattt ttgtgcacag aacctaattt gcattttttgt gcacaaagaa aattttttg      60 atataataga ctttaatagg atattttcta aaaattaaca aatgtctttc tacgataata    120
gaacgcttaa tttcgtggta ataatagttt taactattat tactgttaat tggactttct    180
atattttcaa gcaagatgtt aatttacatt ttttacttgc attagttttg ctgagatgct    240
tgtcatcttt tttactactt agagattata tggctagttg gcgtaagtcg actcaaaaaa    300
cttttttacg taaggctttt attaatttgc cagtattttt catagtggca ttatttttt    360 atggcaaagt cacttttcg ttgatattct ctgagttttt attttatgtt tttttgatca    420
gtttaagtgt ctacttttat tggtatttga tgaacagagg atcagtggat aaaagtaaaa    480
ctgcggttat ttatggtgca ggtgctgcag gaacaaagat tgctcaagaa cttgcttctg    540
ctggttatcg catcaaatgt tttgttgatg acaatgaaac tttacaaaaa agaagtattg    600
atagtaaaaa ggttctatct aaagctgaat taacaaaact attgctatct agtagatttg    660 acctttggt tattgcattg ccaagaaatg caaaccaagt agtcaaaaat atatataaag    720
aatttgaaaa ggattttaat cagattagaa ttatgccgcc tcttgaggaa attcttcaag    780
atgagaattt tatgtcacag ttgaagcctg tttcactcta tgatctatta gcgcgtgata    840
ctaagagttt agataaagaa tctatctcta attttatcaa aaataaggtg gtgctagtca    900
caggagctgg aggtagtata ggttctgaaa tagtacatca atgtatcaag tatcaggcaa    960
aagagttgat attggttgat catagtgagt ttaacttata taaaattact gaggagtgta   1020 gtcatttaa tatcaatagt gtgctatgtt ctgtttgtga tagaaaagca ttggctgagg   1080 ttttttcaaaa gtatactcca aatatagtat ttcatgctgc tgcctacaag catgttccct   1140
tagttgagga gaatatctct agagcaatta gaaataatat cttaggtact aagaatgcta   1200
tagatctggc tatagaagct ggtgttgagt catttatatt gatttccact gataaagcag   1260
tgcgaccaac gaatgttatg ggggctacca agagagtttg tgagctgtat ttacagaatg   1320
ttgatcccaa aaataccaag cttgctgcag tgcgttttgg taatgtgctt ggtagtagtg   1380
gcagtgtgat tccaaaattt gaagagcaaa taagaaaagg tggtcctgtt acagttactc   1440
atcctgaaat tacacgttat tttatgttga taccagaagc ttgtgaactg gtcctacaag   1500
ctggtgctat tgcaaaaaat tcagaggtct ttgtcttaga tatggggcaa cctgtcaaga   1560
ttattgatct tgctaaacaa tttattagac tttctggtag aggtgatatt gatattaaaa   1620
tagttggttt gcgtccagga gagaaacttt acgaagagct tttgatagag gaagatgatg   1680
ttagtaccga ctataaagat attttttattg gtagaaggac tttttacgat attaatactc   1740
taaaccaaga tattgaatcg ttgatcaagg atgatgttga tcagcttgtg atattaaaga   1800
aaattgttcc ggaatttgaa catagattga atgggtagtg gttttatgtt ttatgaggtt   1860
tttaaaagat tgcttgatat tttactttct tttatggggt tgttgttatt aagtcctatt   1920
ttcttaatta ttatttttat gataaagaaa gattcaaaag gacctatatt ttttaaacaa   1980
aagcgctatg gtaaagataa gcaattttt tacatatata agtttagaac tatgtatgtt   2040
gatactccaa agatatgcc aacgcacatg ttacaggatc catcgaaatg tataactaag   2100
gttggaggat tttaaggaa atcatcttta gatgagttgc cacaaattat aaatattcta   2160
aaaggtgaaa tgagcatcgt gggtccaaga ccagccattat ggaatcaaga tgacttaata   2220
gcacaaagag ataagtatgg ggcaaatgct gtgcctgtgg gactgactgg ctgggcacag   2280
```

```
attaatggta gggatgaatt accaatacct gataaagcta aacttgatgg tgattatgta    2340
aaaaataaaa gtacatggtt tgatttaaaa tgtatttttt tgacagtatt ttctgttttt    2400
gccaaaaagg gcgtcgttga gggtggtact ggagctttag gtaacaaaga ggatttaaag    2460
tagtatgaaa aaaagaatct tagttacagg tttgagtagc tatattggta actcatttgc    2520
ggctaaatat aactcagatt ttagtatcga taaaatatct ttgcgcgatg tttcgtgggc    2580
aaatatagac ttaagtggtt atgatgctgt attgcatgtc gctggaattg cccatacttc    2640
aaaggatcct aaactaaaag aaaaatacta taaaataaat acgcaattaa cttatgatct    2700
ggcaaaacaa gctaaagatc aaggtgttcg acagtttgtg ttttttaagta gtattatagt    2760 ttatggtgat agtgcgccaa taggtcaaca aaaagttata actaaatata ccgaacctaa    2820
accagatgat ttttatggag atagtaagct tcaaactgaa attaagctaa atagcctggc    2880
tagtgatgac tttaatattg ctataatcag accaccaatg gtatatggag aaggctcaaa    2940
aggcaactat ccaaagttgg ttaaacttgc aaagtatact tttatttttc ctaatattaa    3000
taaccaaaga agtgttatat ctatagataa tttatctaaa gagattgcag aaataatttt    3060
gcaaactaaa catggagttt ttctacttca agataatgaa tattttttgca cttcacagtt    3120 tataaaaaac tatagaaaag atgttttagg taagagaact tatctgacaa aaattttaa    3180 tccaattata agattgcttg ctaaaaaagt agatttatt aataaagttt ttgggaattt    3240
gacttatgag aagtaagtta ttattcatag ctaatgattt tgatattgta atatatcgtt    3300
tcagaagaga agtaatcgag tcttttgctg ctaaagagta tgagatagta ctagtaacac    3360
catattctaa gaaagcagag gttttttgta aaagtcttgg tgttaagtat ataaatgttg    3420
atatagatag acgaggcaaa aatccttta aggatttgct tcttttattt aactatttca    3480
aaataataaa aaaagaaaaa cctgattaca ttttttagcta tacaattaaa ccaaatttgt    3540
atgttgggtt agtgaatttg ttttttagga agaagttta tccaaatgta acaggcttag    3600
gaagtgtttt tgctaatcat ggtattgttc agaagtttat aatatcttta tataagttat    3660
catttaaaag caccacaaaa gtattctttc agaatgagca aaataaaaag ttatttatag    3720
ctaagaaaat aatcagtgga gaaaaatcaa tattattacc aggttctggg gtaaacttag    3780
atgaaaataa atatgttgac tatcctaaag accaaggaat attaaaattc gttttttcttg    3840 gccgaataat gaaagaaaag gggatttatg aattgttaga agcctttgct atacttgaga    3900
aaaaatataa aaatattagt cttgacattt atggttttg tgatgaaaat aaatctaatt    3960
ttatgggaaa ggttaatacg ataaaatcag taaaatttta tggttttact gataatacta    4020
aagaaaaaat agctagtgca catgcagttg ttttgccatc ttaccatgaa ggaatgtcaa    4080
atgtgctgtt agaagcagct gcgataggta gacctgtaat tgcgtcagat attcctgggt    4140
gtagagaaat ttttgatgat ggtctctctg gcttatcatg taaccctaat gatgtgagtt    4200
ctttacgtaa ctcattagag cagtttataa atatgtcgta tactgataaa atagctatga    4260
gctataaagc tagagctaag atagaaaaag attttgatag aagtattgtt gtcaatgcat    4320
acttacagca aaattaataa taagggttta aattatgagt ttatatgagg atatagtcgc    4380
taaaagagaa aaggtttcat tggttggctt gggttatgtt ggtttaccaa tagctattgc    4440
atttgcaaaa aaaatagatg tgttaggatt tgatatttgt gaaacaaaag ttcaacatta    4500
taaggatggt tttgatccaa caaaagaagt aggagatgag gctgtcagaa atacgacaat    4560
gaaatttagt tgtgatgaaa caagtcttaa agagtgtaaa tttcatattg ttgcagttcc    4620
tacaccagtt aaagcagata aaactcctga tttgacgccg attattaagg caagtgagac    4680
```

```
ggttggtagg aatcttgtca aaggcgctta tgttgtgttt gaatcaactg tttatcctgg    4740
tgttacagaa gatgtttgcg taccaatact tgaaaagag tctggcttga ggtctggtga     4800
agatttcaaa gttggttact ctcctgagag gataaatcct ggtgataagg ttcataggtt   4860
agaaacaatt atcaaagtag tatctggtat ggatgaagag tctttagata ctatagcaaa   4920
agtttatgag ctagtagtag acgcaggagt ttatagagct agtagtataa aagtggctga   4980
agctgctaag gttatagaaa actctcaaag agatgttaat atagcttttg ttaatgagtt   5040
atcgataata tttaatcaga tgggtattga tactctagag gttttagcag cagctgcaac   5100
taaatggaat ttcttaaact ttaagcctgg tcttgttggt ggacattgta ttggtgttga   5160
cccatattac ctaacgtaca aggcagctga gcttggatat cattctcagg taatattatc   5220
tggtcgtagg ataaatgata gtatgggtaa atttgtagtt gagaatttag tcaaaaaact   5280
gatatctgca gatataacctg ttaagcgagc tagagtagca attttcggct ttacttttaa   5340
agaagactgt cctgacacta ggaatactcg agttatagat atggtaaaag agctcaacga   5400
gtatggtata gagccatata ttatagatcc ggtagctgat aaagaagagg ctaaacatga   5460
gtatggactt gagtttgatg atctaagtaa aatggtcaat ctagatgcga tcattattgc   5520
tgttagtcac gaacagttta aagatataac aaagcaacag tttgataggc tatatgcgca   5580
taattctaga aagattatat ttgacatcaa aggtagttta gataaatctg agtttgaaaa   5640
agattatatt tattggagat tgtagtggct tacgataatg ttaaatttcc tcatggttcg   5700
ttttttttgg tgactggagg tgcgggtttt attggctcta atttatgtga agttttactt   5760
agtaagggtt atagagttag gtgtttagat gatctctcaa atggtcacta tcacaatgtt   5820
gagccgtttt taactaattc taattatgag tttataaaag gtgatattag agatttagat   5880
acttgcatga aagcttgtga aggtattgat tatgttctac atcaagctgc ttggggaagc   5940
gtaccaagaa gtattgagat gccattagtg tatgaagata taaatgttaa aggtgcatta   6000
aatatgcttg aagcggctag acaaaataac gttaaaaaat ttgtctatgc ttctagttca   6060
tcagtatatg tgtgatgagcc aaatttacct aaaaagaag gtagagaagg aaatgtttta   6120
tcaccctatg catttacaaa gaaagctaat gaagagtggg cgagactata cacaaagtta   6180
tatggtctag atacttatgg tctaagatat tttaatgttt tcggtagaag acaagatcct   6240
aatggtgcgt atgcagcagt tatacctaaa tttatcaaac agttattaaa tgatgaagcg   6300
ccaactataa atggagatgg taaacagtcg agagatttta catatataga gaatgttatt   6360
gaggcaaatc ttaaagcatg tttagcagat agtaagtatg ccggagagtc ttttaatata   6420
gcttatggag gtagagagta tcttatagat ttgtactata atctttgtga tgccttgggt   6480
aaaaaaatag agccaaattt tggtccagat agagcgggtg atattaagca tagtaatgct   6540
gatatttcga aggctaggaa tatgctcgga tataatccgg aatatgattt tgaattaggc   6600
ataaagcatg ctgttgagtg gtatttaatt aattaaatgg tatttaatc aagtgtacat    6660 aaaaaaagtg tcttttaaaa ttttatattt atatttacta gctttttgta ttatttttag   6720
tttagaattt aaatttgcta tattgaatat tatagttat cttccggctt gtattttggg    6780 tttttttagct cttaaaaaac tatttgtcgg aaatattgtt aagaaacaat tagctttcct   6840
ttttttcttt ttcttttttat caatgattta tttaataata gtccaaataa tcttacttga   6900
tgcagcatca ttgtttcctc agttttatt taacattttg atcgcgatag gttttgtaa     6960 ctttattttt gttcatatg ataataatga aaattattt tttaatatgt ctaaaataat    7020 atttttgtt actttcttac aatctatttt tgtatttctt tcaaggtatt atatattttt    7080
```

```
aaatgattgg atattctttt ttttagtgaa aaaagggaat attgagattt cgaatgttat    7140
tgaatataag ttaagagtat tcggacttag taacgctgga ggggatggtt taggattttc    7200
aattactata ggattatgtt tttctatatt ttattttatc aaatatatta aaggtaaatc    7260
tatatttacc aaacttatgc tgtttgtacc tttaattctt attgtgtttt ctaatatttt    7320
catatctaga acatcactct taacttcttc acttatattg ttaataacaa tattttatat    7380
atatattaaa aaagaaaaat tactgtttat tataatattg gcgctattct ttttatcaat    7440
atggatattg ttcaaattaa atttgaattt gagttgggct tttgaaaata tttactcgta    7500
cattcaatct ggcgattttt cacatggaag tctaagtgtt ttaatcaata aaatgctttt    7560
tgtgccagat aaccttttga cttggatatt tggttgtgag gatgttagta atactgatat    7620
tggttatatt aaatatttat actattatgg gattatattt agtatgtttt tttatattct    7680
tattattttc ttgtactttg aaatgagaaa atgttttata ttttcagagt atcgatcatt    7740
atttctattg ttgttaatag tatgtttagt ttttcaagca aaaataattt ttttgacagt    7800
aggattattt actaaattaa ccattatatt atttattttt tctcttaaag aaaacagctt    7860
tacaactagg agtgtgattt gaaaaggttt gtacatttaa taataaacct taaccaaggt    7920
ggtgctgaaa caatgcttta taaactttgc aaatctatgg ataagtcaat atatcatatt    7980
acgattatat cacttatggg taggggagta tttgcaaata agttagaagc ttatggtgtt    8040
aaagtttata cattaaattt aaataaattt aatgtactat ttgtattgtt taaatatatt    8100
aagattatca gaagaataaa gcctgatgtt attcatgctt ggatgtatca tgcaaatgta    8160
atttctatat tatgcaagcc ttttttataga aagactaaat atataaatag tataagaatg    8220
ggattggaga attatgatgg tcataagaat cttacaaagt ttatgataaa gttgaatgca    8280
aaattttcta agttctcaga tttaacatta aataattcaa agaaatcatt agaagatcat    8340
caaaatatag gttttaaaaa ccaatgcttt atagcaaatg gttttgataa agatgttttt    8400
aaaccgagct ttttaaagta tgaaaaattt cgtttaaata atgatttaga tgataatgtt    8460
aaaattatag gtatcatagc aagaaatcat gctgataaaa atatttctcg tttcttacaa    8520
atagctaatt tattgttaaa aagtaatcct agtttacggt ttttaattgc tggaagagag    8580
tgttcgaaaa tagatatagg tagttatcta gataacaaaa gtaatgtaaa taagtttttt    8640
gtatttgaat ctgtggattc tagtgaatac ttaccagtat tagatttata tttgtctaca    8700
tcaaaagttg aaggttttcc aaatatactt gcagaagcca tgctatgtga agttcctatt    8760
gttgcttcta atgttggaga ttgtaaagat atacttaatg gatacggtga agtttttgag    8820
cttagtcaag gtaataaaga aataatagaa aagattatga aagttttaga acaacggta     8880 gtcatgaaaa agcgcatgag agaatatata ataataatt ttagtataga agctattttg    8940
gaaaaacacg aaaaacttta tcatgagggc agtgtctaat gtgtggagta gtaggctttt    9000
actcatttaa taagaagaa ggttttgact caataattaa tcaatcattg ctttctataa    9060
agcatagagg gtcggatgat agtgggtatt ggtgcgacaa tcaagttact ctggggcata    9120
ctagattatc aatacacgat ataactaatg cgggacatca gccaatgtta tctaatagcg    9180
gtaatactgc tattgtgttt aatggagaaa tatataatta cttatccata aaaaatcagc    9240
tattaagtga atattcaaat cttaaatta aaagtaacag tgatactgag gttttggtca    9300
atgctattga actttggggt atagataaaa ctttagaaaa atgcatagga atgtttgctt    9360
ttggagttta cagtagaaaa actagttgct taatactagc tagagataga tttggcgaga    9420
agccattata ttttggtatc caaaatggta ttttgggttt tgcatcagaa ttgaaggcac    9480
```

```
ttaagccatt aaaggaatgt ggctggaggt ttgatataga tagagatgct ttagcaacat    9540
atatgaggta tgcttatgta ccaacaccat actctattta taaaaatata tctaaactaa    9600
atgtaggtag ttacataaaa tttgatgcta aaggtaatag taaagagtat aaatattggg    9660
attctaaaaa agtactagat tcagaaaaat ataaagattc gtatgatcaa gcaatcctag    9720
atttagaaat taagcttaaa agtacactat caatacaaat gcagtcagat gttcctctag    9780
gagcattttt atccggagga attgactcaa caactgtagt tgctcttatg caaagtatgt    9840
ctaaagataa gataaacact tttagtatag gttttaatca aaaagaatat aatgaagctg    9900
agcatgcaag agcagtagca aaacatatag gtacaaacca cacagatatg tatgttacag    9960
aaagagatgc tcttgatgta ataccaaaac ttgctggaat atatgacgag ccctttgctg   10020
attcatcaca aataccaacg tatcttgtga gtaaaatagc taagtcgaaa gtaacagttg   10080
cactatcagg tgacgctggt gatgagctct tggcggttta atagatac ttttagcac     10140 caaatattgc taaaaaatc aaatttgcta agttacttaa atatgcacca gatgcttgga   10200 taaaaaagc tgagatatta aattttggta agttcgcttt attagcagat aaactactaa   10260
aactaaaaag agttctcgaa aaagcaaaaa caaataaaga gctttatgta ctactttgtt   10320
cacaaataaa tgatactagc tttgtgttag gagcaaaaga gtatgatata ttaagagata   10380
agaatattta tgatattcca caattatctt tccaagagtg gatgatgttt gttgattcta   10440
atacatatat gatagatgat atattggtta aggttgatag agcagctatg gctaactctc   10500
tagagacaag agtgccattt ttagatcata atattatga atttgcttat tccttaccaa   10560
ttgactataa atacaacga ggtaacggaa aaagaatttt gaaagatttg ttatataaat    10620
atgtgccaga aagtttggtc aataggtcta agatgggggtt tggtattccg cttgctaaat  10680
ggttaagaga agatttacga gagtgggcag ataatttact ggattatagt aaaatagaca   10740
agcaaggtta cttaagtcct gaggtggtgc aaaaatattg gcaagagcat ttgagtggta   10800
aaagaaattg gcaagcaata ttatggaata ttctaatttt tcaggagtgg ttagataatg   10860
agtaaagtaa atgtaacaaa accatactta ccagatataa ataaatataa aagctatgta   10920
aataaaatat acaaaaatgg atggcttact aataatggtc cgttagtgca agagctagaa   10980
aaaagacttg caaagtatct aggtgttaaa aatatagttt tagtatcaaa tggtacaatt   11040
gcattagaaa tcgcgtatag agcgttagga gtcaaaggaa gtgcaattac tactccattt   11100
tcatttgttg ctactacatc ttcattggtt tctaacaatg taaaaccagt gtttgttgat   11160
attgatgaga atactctaag tatagacgtc tctaaaatta agtatgctat tgaagaggat   11220
acttcagcta ttgtgccagt tcatgtgttt ggaaatggtt gtgaagttga aaaaatagac   11280
atgctggcta aaaaacataa cttaaaagtt atttatgatg cagcacatgc ttttgatgtt   11340
aagtataagg gtgagagtat attaaactat ggtgatattt cgacattaag ttttcatgca   11400
acaaagattt ttcattctat tgaaggaggt gcgcttatca ttaatgatga tagtcttgtt   11460
gaaaaagttc gttatttcat taattttggt atagaaagct cagaatcaat accttactta   11520
ggtactaatg ctaaaatgaa tgaatttgag gcggctatgg gactttgtgt tctagatgat   11580
attatagaaa ttaagagcaa aaggaaagtt attacagaga tatgaggc tgggttagat    11640 ggattggtaa agtttcaaga acagaatcag cattctagta ggaattatag ctattttcca   11700
gtaatattta ggactgagga ggaacttctc agagtacaga aagcactaat acaaaatgat   11760
ataatatcgc gtagatattt ttatccatca ttagatagtc ttagttatat agagccaaag   11820
cagtatatgc caatctcaag agatatatct aaaagaatat tatgtttgcc aatttatgca   11880
```

```
gagttagaag acgataaaat taataaaata attaataata tcaaagaggt ttcctcatga   11940
aaaaaatatt tgttgttaca gataatagaa ctattctaag tgatttttaaa aatatcattg  12000 gtagtaaaaa tgatgtacag gttgattatt tttgtagttt caagagtcaa acttcttttg   12060
ccaaagaaat atataacagt gagattaagc caatagatat gaaaaaaaat ggcaatgatc   12120
ttattggtaa gtatgattta ggttttttctt gtcattcgaa acaattattt ccagcaaaat  12180
tagttaattc agtattatgt ataaatattc atcctggact taatccatat aatagagggt   12240
ggtttccaca ggtcttctct attataaata aactacctat aggagcaact attcatgtga   12300
tggatgaaga gatagatcat ggagatataa tcattcagga agaagttgaa gttaattctt   12360
tcgaaaactc ttttgatgtt tatgctaaag ttcaaaaaaa agaagttgag ttgttcacta   12420
aagtcataga tgatatttttg aataataagt tcactcgaat caaacctaac tccgaaggca   12480
actataattc aattcatgat tataaaaaca tgtgtgaaat tgatttagat aaaatagtaa   12540
caatgcggga agcaattgac tatctaaggg ctatgacaca ccctccatat aaaaatagtt   12600
atttcattga tgagcatgga aataaagtat ttgttgctct tgaacttgaa aagataagtt   12660
agaaaaatga gccttaaaaa aaatacaata tcaaattata taacacaact atatactagc   12720
ttaattggta ttgttatact tcctttgtat ttacaacatt taagtcatga tgcatttggt   12780
ctgattggtt tttttacagt ttttcaaacg tggttacggt tgttggatgt tggtataaca   12840
ccaactttat caagagaagt ggctcatgtt agaggtagta ctgatgacta tcattactta   12900
cgcaagttgg ttagatcgtt agagctattt ttcattattg ttggtgttct ggtatttatt   12960
gtaattagta cacattcaag gtatatatcc acctcttggt tacatatagg ctcgctagat   13020
gctgatagtg taagtgtatg tattgcactt atgggtttaa tgtttgcatt aagatgggtg   13080
tctgatctat atggtggtgg tttgcgtggc tttgaaagac aggttcttta taataattta   13140 agtatccatac aaacgacact acagtttatt ggtggattat tatttatctg ctatgtgtct  13200
actaatatta tgtattatttt tgtatatcag acaataattg cgatactata tctagtatgt   13260
attgcaattg cattttataa aatactacca tcatcattta gcgtgggttt aaggtttgat   13320
tttaaaataa ttagaaaagt gcttccattt gcactaggca ttgcatattc tacaacagtt   13380
tggattattg tcactcaatc tgataaatta gtgttctcac atgtattacc attatctgag   13440
tatggttatt tatctttatt gatagtgata tctagtgctg ttacgatatt gtcctctccg   13500
attagcatag ctattcagcc tagaatgaca atgctattag cccaacaaaa tgtaaaagga   13560
atggaaagct tatatttaaa atcatccttg atctcaatta cttttttatc tgctgtagta   13620
acatgtgttt tgatgtattc tcatcagctg ttgcagtcat ggacaggaag tatggaaatt   13680
gctaattggg gtagtaatat cttaaatata tatgttttat cagcatctat tatttgtata   13740
atatcatttc aatatttttt acagtatgct tatggtaagt taaagctaca taatacatat  13800
aatacaatta gtttagtatt ttttgctcct atagttatat atactgctta taattatgga   13860
gtgtatacta cagcactatt atggcttgga tatgctatag tggggctgat aatctggatg   13920
cctattgtac accatgtatt tgctaaaggt atcaataggg atttttttat aaatttagca   13980
gttattacta tagtatgttt tttattatcg ttaatattta agggttggta tatttatcca   14040
agtaaaattg ggttggtaga attaatattg attgggtttg cattttttatt tatacaaatt   14100 tgtatagagt atgtttttgtt tcggtacaag gttttgaggt gtatagatga ttaaagtttc   14160
agtatgtgtg atgacataca atcaagaaaa gtatattggt caatgtttag agtctttggt   14220
tactcaagag actgattttg actttgagat aatcgttgga gatgattttt ctacagatgg   14280
```

```
tacaagagat gttattcaag agtatcaaaa aaagtatccg gatatcataa agccagtttt   14340
tagagataag aatgtgggaa ttactgaaaa tattaaagaa atctattttg ttgcaaatgg   14400
tgagtatata gctcatatgg atggtgatga ttatgcattg cctggtaaac ttcaaattca   14460
ggctgatttt ttggataata atccaagatg tacgggagtt tttcataata taaatatact   14520
ctatccaaat ggtaatatac aacatagtag gtttgcttgt tcaaataaga gtatattcaa   14580
tttatcagac actttacgcg gagttgctgt tggtgcaaat agttcaaaaa tgttcagaac   14640
atcggttttg gatgatttga ttttaccgga tatagagctt ctagattatt attttcatgt   14700
tataacagca gaaaaaggtt atttaagttt tttaaattct aatgaatcct atagtgtgta   14760
cagaaaaggt attggtatca catctaagtc taaggaaaaa atctataata cttatgctgg   14820
attatttgaa tattttttgg atagatatcc tgaagagaaa ttaaatattt gtatccctgt   14880
tgtgcaaatg ataatttcgg ctattaaagg gagatgtttt attagtgcta ttcgtctatt   14940
caaaatttta attagatcaa gatgtattcc attagtaagt tggtttaaat atagatttga   15000
aaaataaata tcatttagag gattatgtga aatgaaggga ataattctag ctggtggcag   15060
tggtacaagg ctatatccac ttaccttggg tgttagcaaa cagctgctac ctgtttatga   15120
caagccattg ttatactatc cactatctgt gcttatgctt gcaggtatta gggagatatt   15180
aattatctct acagtgcgtg atatctcact tatccaagag cttcttggtg atggttcaca   15240
atttggtata cagttgagtt ataaaatcca gccatcacca gatgggcttg ctcaagcatt   15300
tattcttggt gaggagtttt tggcgggtga ctcagcttgt ttgatattag gagataatat   15360
ctactatggt caaggtatga ctacaatgct agagtctgca agagcacagt gtggaggtcc   15420
agctggtggc gcttgtgttt ttggttatta tgttaatgat ccgcatagat atggtatagt   15480
cgaatttgat aagcaaaaaa atgtaatttc ggtagaggaa aagccacaga tcctaagtc    15540 acactatgct atcacaggtt tattttta tgataataat gttgttgagt atgctaaaca    15600
agtcaaacca tctgcacgtg gtgagctaga gattacttca cttaatgagt tatatctaaa   15660
agaaaataag ctaaatgtcg aactcttagg gcgtggcttt gcttggcttg atgctggtac   15720
gcatgattca ttgctagagg caggtcaata tgtcgcaact attgagaaaa gacaagggct   15780
taaaattgca tgtttggaag aaattgcatg gcgtaaaggc tttatctcaa cacaacaagt   15840
tctagctcaa gctgaaaaac tttctaagac agagtatggt cagtatctga agaatttaat   15900
taaggatggt ttataaatta atccgtcata cccatgaagg tgggtatctc ataaaagttg   15960
gatatgtttt ggagattcca atctgcgcag taatgacagg tttggtaata tatagcgatg   16020
ttttacaatg actaaaaatg gttttatgta tattcttaca aataaggata atactgttct   16080
gtacatagtt gtaacatcta atttgataaa aagaatgtat gagcataaac atagccttgc   16140
agatggtttt actaaaaata taatgttaat aagttagttt atttttgaaat ttatgaagat   16200 ataaaagcag caattctgtg agaaaagcag ttgaaaaaat gaaacagatc ttggaaagaa   16260
cgaattatta atgagatgaa tccgaattgg aatgatttat atgaattaat atgtgagtaa   16320 aactttgtc ttactggtgc agataggtat ctctaaatat cagatgtgat tgggagatta    16380
ccgcctacgc ggtaatgaca agtttatgcg gtaatgatag tttagtgaga gaatgactag   16440
tcactatagg aatgatgatg taatgaggaa tgaaaaaatg aactacaaac caaaaatat    16500 cctagtaaca ggtgcggcgg gatttattgg tagtaactat gtgcgtatga tgttatcacg   16560
ctatagtgat atcaaaataa tctcgtatga taagcttact tatgcgggta gtttagataa   16620
tctaaaagac ttgaataatg aacataacca tacttttata aaaggtgata tttgtgatga   16680
```

```
agttttagta tatcaaacac tgaaagaata taaaattgat acgatagtac attttgctgc    16740
agaatcgcat gttgataatt caattgctaa tccaaggta tttttagaaa cgaatgtgat     16800
aggtacattt acacttttag attgtgctaa aaggtattgg ttagatgagc taggtttaga   16860
agaaactagt tgtaggtttc atcatgtatc tactgatgag gtatatggta ccttggcaaa    16920
agatgaacca gcctttactg agattaaggc ttatgagcca aattcaccgt attcggcatc    16980
taaggcggga tctgatcata tttctagagc atatcatcat acctataaac ttccggtaac    17040
aatttcaaat tgttcaaaca actatggacc ataccaacat cgagagaaat taatccctgt    17100
agtgataaat agttgtataa actacaagcc tattcctgtt tacggagatg gttcgaatat    17160
tcgagattgg ctatatgtag aagatcactg cgatgctatc cagacaattg ttgagaaagg    17220
agtggttgga gaggtttata atattggtgg tattaatgaa gttgataatc taaccttggt    17280
aaaaactatc tgtaaactaa tggatgaata taaaccagaa aatgctccac attctaactt    17340
aatcacattt gtggaagata gaaaggaca tgattggcgt tatgctattg ataacagcaa     17400
gattcagaat gagttaggat ggaagccatc acaagatttt gataagatgt ttagacaaac    17460
tattgagttt tatctatagc ttaaatattt atcttatgag tatctctaaa aaatcaattt    17520
aatttatttt tgtgttaaaa agtagtgttc gcaagaatat agttaatccg aaagatattt    17580
gtagaaaaag atatttgtag aaatgttata atgtctaata aaa                      17623
```

<210> SEQ ID NO 2
<211> LENGTH: 247
<212> TYPE: PRT
<213> ORGANISM: Francisella tularensis

<400> SEQUENCE: 2

```
Met Asn Tyr His Ile Lys Glu Val Phe Trp Ser Ile Ile Leu Ser Phe
 1               5                   10                  15

Leu Lys Ser Gln Lys Gly Ile His Thr Asn Asp Glu Ala Lys Leu Arg
            20                  25                  30

Leu Phe Ile Glu Ala Val Phe Tyr Val Leu Arg Thr Gly Cys Gln Trp
        35                  40                  45

Arg Met Leu Pro Phe Tyr Tyr Gly Lys Tyr Arg Ser Ile His Lys Arg
    50                  55                  60

Phe Lys Asp Trp Cys Asp Lys Asp Ile Phe Ser Arg Leu Phe Lys Ser
65                  70                  75                  80

Val Gln Asn Pro Asp Leu Gln Glu Val Met Leu Asp Ser Thr Ile Ala
                85                  90                  95

Arg Ala His Ala Cys Ala Thr Gly Tyr Asp Lys Asp Asn Gln Ala
            100                 105                 110

Ile Gly Arg Ser Val Gly Arg Ile Thr Thr Lys Ile His Ala Met Thr
        115                 120                 125

Asp Ala Leu Gly Asn Pro Ile Glu Ile Leu Leu Ser Glu Asp Lys Thr
    130                 135                 140

His Asp Ser Lys Val Ala Ile Asp Leu Leu Lys Asn Val Tyr Asn Thr
145                 150                 155                 160

Lys Val Ile Ala Asp Arg Ala Tyr His Ser Asn Glu Ile Arg Gln His
                165                 170                 175

Ile Gln Gly Ile Ser Ser Glu Ala Val Ile Pro Cys Lys Ser Asn Thr
            180                 185                 190

Leu Asn His Ile Pro Phe Asp Ser His Val Tyr Lys Glu Arg His Leu
        195                 200                 205
```

```
Ile Glu Asn Phe Phe Ser Lys Ile Lys His Phe Arg Arg Val Phe Ser
    210                 215                 220
Arg Phe Asp Lys Thr Ile Leu Ala Tyr Ile Gly Met Ile Lys Leu Ala
225                 230                 235                 240
Cys Thr Phe Ile Trp Leu Arg
                245

<210> SEQ ID NO 3
<211> LENGTH: 578
<212> TYPE: PRT
<213> ORGANISM: Francisella tularensis

<400> SEQUENCE: 3

Met Ser Phe Tyr Asp Asn Arg Thr Leu Asn Phe Val Val Ile Ile Val
1               5                   10                  15
Leu Thr Ile Ile Thr Val Asn Trp Thr Phe Tyr Ile Phe Lys Gln Asp
                20                  25                  30
Val Asn Leu His Phe Leu Leu Ala Leu Val Leu Leu Arg Cys Leu Ser
            35                  40                  45
Ser Phe Leu Leu Leu Arg Asp Tyr Met Ala Ser Trp Arg Lys Ser Thr
50                  55                  60
Gln Lys Thr Phe Leu Arg Lys Ala Phe Ile Asn Leu Pro Val Phe Phe
65                  70                  75                  80
Ile Val Ala Leu Phe Phe Tyr Gly Lys Val Thr Phe Ser Leu Ile Phe
                85                  90                  95
Ser Glu Phe Leu Phe Tyr Val Phe Leu Ile Ser Leu Ser Val Tyr Phe
                100                 105                 110
Tyr Trp Tyr Leu Met Asn Arg Gly Ser Val Asp Lys Ser Lys Thr Ala
            115                 120                 125
Val Ile Tyr Gly Ala Gly Ala Ala Gly Thr Lys Ile Ala Gln Glu Leu
130                 135                 140
Ala Ser Ala Gly Tyr Arg Ile Lys Cys Phe Val Asp Asp Asn Glu Thr
145                 150                 155                 160
Leu Gln Lys Arg Ser Ile Asp Ser Lys Lys Val Leu Ser Lys Ala Glu
                165                 170                 175
Leu Thr Lys Leu Leu Leu Ser Ser Arg Phe Asp Leu Leu Val Ile Ala
            180                 185                 190
Leu Pro Arg Asn Ala Asn Gln Val Lys Asn Ile Tyr Lys Glu Phe
                195                 200                 205
Glu Lys Asp Phe Asn Gln Ile Arg Ile Met Pro Pro Leu Glu Glu Ile
            210                 215                 220
Leu Gln Asp Glu Asn Phe Met Ser Gln Leu Lys Pro Val Ser Leu Tyr
225                 230                 235                 240
Asp Leu Leu Ala Arg Asp Thr Lys Ser Leu Asp Lys Glu Ser Ile Ser
                245                 250                 255
Asn Phe Ile Lys Asn Lys Val Val Leu Val Thr Gly Ala Gly Gly Ser
            260                 265                 270
Ile Gly Ser Glu Ile Val His Gln Cys Ile Lys Tyr Gln Ala Lys Glu
            275                 280                 285
Leu Ile Leu Val Asp His Ser Glu Phe Asn Leu Tyr Lys Ile Thr Glu
            290                 295                 300
Glu Cys Ser His Phe Asn Ile Asn Ser Val Leu Cys Ser Val Cys Asp
305                 310                 315                 320
Arg Lys Ala Leu Ala Glu Val Phe Gln Lys Tyr Thr Pro Asn Ile Val
                325                 330                 335
```

```
Phe His Ala Ala Ala Tyr Lys His Val Pro Leu Val Glu Glu Asn Ile
                340                 345                 350

Ser Arg Ala Ile Arg Asn Asn Ile Leu Gly Thr Lys Asn Ala Ile Asp
            355                 360                 365

Leu Ala Ile Glu Ala Gly Val Glu Ser Phe Ile Leu Ile Ser Thr Asp
        370                 375                 380

Lys Ala Val Arg Pro Thr Asn Val Met Gly Ala Thr Lys Arg Val Cys
385                 390                 395                 400

Glu Leu Tyr Leu Gln Asn Val Asp Pro Lys Asn Thr Lys Leu Ala Ala
                405                 410                 415

Val Arg Phe Gly Asn Val Leu Gly Ser Ser Gly Ser Val Ile Pro Lys
            420                 425                 430

Phe Glu Glu Gln Ile Arg Lys Gly Gly Pro Val Thr Val Thr His Pro
        435                 440                 445

Glu Ile Thr Arg Tyr Phe Met Leu Ile Pro Glu Ala Cys Glu Leu Val
    450                 455                 460

Leu Gln Ala Gly Ala Ile Ala Lys Asn Ser Glu Val Phe Val Leu Asp
465                 470                 475                 480

Met Gly Gln Pro Val Lys Ile Ile Asp Leu Ala Lys Gln Phe Ile Arg
                485                 490                 495

Leu Ser Gly Arg Gly Asp Ile Asp Ile Lys Ile Val Gly Leu Arg Pro
            500                 505                 510

Gly Glu Lys Leu Tyr Glu Gly Leu Leu Ile Glu Glu Asp Asp Val Ser
        515                 520                 525

Thr Asp Tyr Lys Asp Ile Phe Ile Gly Arg Arg Thr Phe Tyr Asp Ile
    530                 535                 540

Asn Thr Leu Asn Gln Asp Ile Glu Ser Leu Ile Lys Asp Asp Val Asp
545                 550                 555                 560

Gln Leu Val Ile Leu Lys Lys Ile Val Pro Glu Phe Glu His Arg Leu
                565                 570                 575

Asn Gly

<210> SEQ ID NO 4
<211> LENGTH: 205
<212> TYPE: PRT
<213> ORGANISM: Francisella tularensis

<400> SEQUENCE: 4

Met Phe Tyr Glu Val Phe Lys Arg Leu Leu Asp Ile Leu Leu Ser Phe
1               5                   10                  15

Met Gly Leu Leu Leu Leu Ser Pro Ile Phe Leu Ile Ile Ile Phe Met
                20                  25                  30

Ile Lys Lys Asp Ser Lys Gly Pro Ile Phe Phe Lys Gln Lys Arg Tyr
            35                  40                  45

Gly Lys Asp Lys Gln Phe Phe Tyr Ile Tyr Lys Phe Arg Thr Met Tyr
        50                  55                  60

Val Asp Thr Pro Lys Asp Met Pro Thr His Met Leu Gln Asp Pro Ser
65                  70                  75                  80

Lys Cys Ile Thr Lys Val Gly Gly Phe Leu Arg Lys Ser Ser Leu Asp
                85                  90                  95

Glu Leu Pro Gln Ile Ile Asn Ile Leu Lys Gly Glu Met Ser Ile Val
            100                 105                 110

Gly Pro Arg Pro Ala Leu Trp Asn Gln Asp Asp Leu Ile Ala Gln Arg
        115                 120                 125

Asp Lys Tyr Gly Ala Asn Ala Val Pro Val Gly Leu Thr Gly Trp Ala
```

-continued

```
            130                 135                 140
Gln Ile Asn Gly Arg Asp Glu Leu Pro Ile Pro Asp Lys Ala Lys Leu
145                 150                 155                 160

Asp Gly Asp Tyr Val Lys Asn Lys Ser Thr Trp Phe Asp Leu Lys Cys
                165                 170                 175

Ile Phe Leu Thr Val Phe Ser Val Phe Ala Lys Lys Gly Val Val Glu
            180                 185                 190

Gly Gly Thr Gly Ala Leu Gly Asn Lys Glu Asp Leu Lys
        195                 200                 205

<210> SEQ ID NO 5
<211> LENGTH: 263
<212> TYPE: PRT
<213> ORGANISM: Francisella tularensis

<400> SEQUENCE: 5

Met Lys Lys Arg Ile Leu Val Thr Gly Leu Ser Ser Tyr Ile Gly Asn
1               5                   10                  15

Ser Phe Ala Ala Lys Tyr Asn Ser Asp Phe Ser Ile Asp Lys Ile Ser
            20                  25                  30

Leu Arg Asp Val Ser Trp Ala Asn Ile Asp Leu Ser Gly Tyr Asp Ala
        35                  40                  45

Val Leu His Val Ala Gly Ile Ala His Thr Ser Lys Asp Pro Lys Leu
    50                  55                  60

Lys Glu Lys Tyr Tyr Lys Ile Asn Thr Gln Leu Thr Tyr Asp Leu Ala
65                  70                  75                  80

Lys Gln Ala Lys Asp Gln Gly Val Arg Gln Phe Val Phe Leu Ser Ser
                85                  90                  95

Ile Ile Val Tyr Gly Asp Ser Ala Pro Ile Gly Gln Gln Lys Val Ile
            100                 105                 110

Thr Lys Tyr Thr Glu Pro Lys Pro Asp Asp Phe Tyr Gly Asp Ser Lys
        115                 120                 125

Leu Gln Thr Glu Ile Lys Leu Asn Ser Leu Ala Ser Asp Asp Phe Asn
    130                 135                 140

Ile Ala Ile Ile Arg Pro Pro Met Val Tyr Gly Glu Gly Ser Lys Gly
145                 150                 155                 160

Asn Tyr Pro Lys Leu Val Lys Leu Ala Lys Tyr Thr Phe Ile Phe Pro
                165                 170                 175

Asn Ile Asn Asn Gln Arg Ser Val Ile Ser Ile Asp Asn Leu Ser Lys
            180                 185                 190

Glu Ile Ala Glu Ile Ile Leu Gln Thr Lys His Gly Val Phe Leu Leu
        195                 200                 205

Gln Asp Asn Glu Tyr Phe Cys Thr Ser Gln Phe Ile Lys Asn Tyr Arg
    210                 215                 220

Lys Asp Val Leu Gly Lys Arg Thr Tyr Leu Thr Lys Ile Phe Asn Pro
225                 230                 235                 240

Ile Ile Arg Leu Leu Ala Lys Lys Val Asp Phe Ile Asn Lys Val Phe
                245                 250                 255

Gly Asn Leu Thr Tyr Glu Lys
            260

<210> SEQ ID NO 6
<211> LENGTH: 363
<212> TYPE: PRT
<213> ORGANISM: Francisella tularensis

<400> SEQUENCE: 6
```

```
Met Arg Ser Lys Leu Leu Phe Ile Ala Asn Asp Phe Asp Ile Val Ile
1               5                   10                  15

Tyr Arg Phe Arg Arg Glu Val Ile Glu Ser Phe Ala Ala Lys Glu Tyr
                20                  25                  30

Glu Ile Val Leu Val Thr Pro Tyr Ser Lys Lys Ala Glu Val Phe Cys
            35                  40                  45

Lys Ser Leu Gly Val Lys Tyr Ile Asn Val Asp Ile Asp Arg Arg Gly
50                  55                  60

Lys Asn Pro Phe Lys Asp Leu Leu Leu Phe Asn Tyr Phe Lys Ile
65              70                  75                  80

Ile Lys Lys Glu Lys Pro Asp Tyr Ile Phe Ser Tyr Thr Ile Lys Pro
                85                  90                  95

Asn Leu Tyr Val Gly Leu Val Asn Leu Phe Phe Arg Lys Lys Phe Tyr
            100                 105                 110

Pro Asn Val Thr Gly Leu Gly Ser Val Phe Ala Asn His Gly Ile Val
                115                 120                 125

Gln Lys Phe Ile Ile Ser Leu Tyr Lys Leu Ser Phe Lys Ser Thr Thr
        130                 135                 140

Lys Val Phe Phe Gln Asn Glu Gln Asn Lys Lys Leu Phe Ile Ala Lys
145                 150                 155                 160

Lys Ile Ile Ser Gly Glu Lys Ser Ile Leu Pro Gly Ser Gly Val
                165                 170                 175

Asn Leu Asp Glu Asn Lys Tyr Val Asp Tyr Pro Lys Asp Gln Gly Ile
            180                 185                 190

Leu Lys Phe Val Phe Leu Gly Arg Ile Met Lys Glu Lys Gly Ile Tyr
        195                 200                 205

Glu Leu Leu Glu Ala Phe Ala Ile Leu Glu Lys Tyr Lys Asn Ile
    210                 215                 220

Ser Leu Asp Ile Tyr Gly Phe Cys Asp Glu Asn Lys Ser Asn Phe Met
225                 230                 235                 240

Gly Lys Val Asn Thr Ile Lys Ser Val Lys Phe Tyr Gly Phe Thr Asp
                245                 250                 255

Asn Thr Lys Glu Lys Ile Ala Ser Ala His Ala Val Val Leu Pro Ser
            260                 265                 270

Tyr His Glu Gly Met Ser Asn Val Leu Leu Glu Ala Ala Ala Ile Gly
        275                 280                 285

Arg Pro Val Ile Ala Ser Asp Ile Pro Gly Cys Arg Glu Ile Phe Asp
290                 295                 300

Asp Gly Leu Ser Gly Leu Ser Cys Asn Pro Asn Asp Val Ser Ser Leu
305                 310                 315                 320

Arg Asn Ser Leu Glu Gln Phe Ile Asn Met Ser Tyr Thr Asp Lys Ile
                325                 330                 335

Ala Met Ser Tyr Lys Ala Arg Ala Lys Ile Glu Lys Asp Phe Asp Arg
            340                 345                 350

Ser Ile Val Val Asn Ala Tyr Leu Gln Gln Asn
        355                 360

<210> SEQ ID NO 7
<211> LENGTH: 436
<212> TYPE: PRT
<213> ORGANISM: Francisella tularensis

<400> SEQUENCE: 7

Met Ser Leu Tyr Glu Asp Ile Val Ala Lys Arg Glu Lys Val Ser Leu
1               5                   10                  15
```

```
Val Gly Leu Gly Tyr Val Gly Leu Pro Ile Ala Ile Ala Phe Ala Lys
            20                  25                  30
Lys Ile Asp Val Leu Gly Phe Asp Ile Cys Glu Thr Lys Val Gln His
            35                  40                  45
Tyr Lys Asp Gly Phe Asp Pro Thr Lys Glu Val Gly Asp Glu Ala Val
 50                  55                  60
Arg Asn Thr Thr Met Lys Phe Ser Cys Asp Glu Thr Ser Leu Lys Glu
 65                  70                  75                  80
Cys Lys Phe His Ile Val Ala Val Pro Thr Pro Val Lys Ala Asp Lys
                 85                  90                  95
Thr Pro Asp Leu Thr Pro Ile Ile Lys Ala Ser Glu Thr Val Gly Arg
            100                 105                 110
Asn Leu Val Lys Gly Ala Tyr Val Val Phe Glu Ser Thr Val Tyr Pro
            115                 120                 125
Gly Val Thr Glu Asp Val Cys Val Pro Ile Leu Glu Lys Glu Ser Gly
130                 135                 140
Leu Arg Ser Gly Glu Asp Phe Lys Val Gly Tyr Ser Pro Glu Arg Ile
145                 150                 155                 160
Asn Pro Gly Asp Lys Val His Arg Leu Glu Thr Ile Ile Lys Val Val
                165                 170                 175
Ser Gly Met Asp Glu Glu Ser Leu Asp Thr Ile Ala Lys Val Tyr Glu
            180                 185                 190
Leu Val Val Asp Ala Gly Val Tyr Arg Ala Ser Ser Ile Lys Val Ala
            195                 200                 205
Glu Ala Ala Lys Val Ile Glu Asn Ser Gln Arg Asp Val Asn Ile Ala
210                 215                 220
Phe Val Asn Glu Leu Ser Ile Ile Phe Asn Gln Met Gly Ile Asp Thr
225                 230                 235                 240
Leu Glu Val Leu Ala Ala Ala Thr Lys Trp Asn Phe Leu Asn Phe
                245                 250                 255
Lys Pro Gly Leu Val Gly Gly His Cys Ile Gly Val Asp Pro Tyr Tyr
            260                 265                 270
Leu Thr Tyr Lys Ala Ala Glu Leu Gly Tyr His Ser Gln Val Ile Leu
            275                 280                 285
Ser Gly Arg Arg Ile Asn Asp Ser Met Gly Lys Phe Val Val Glu Asn
290                 295                 300
Leu Val Lys Lys Leu Ile Ser Ala Asp Ile Pro Val Lys Arg Ala Arg
305                 310                 315                 320
Val Ala Ile Phe Gly Phe Thr Phe Lys Glu Asp Cys Pro Asp Thr Arg
                325                 330                 335
Asn Thr Arg Val Ile Asp Met Val Lys Glu Leu Asn Glu Tyr Gly Ile
            340                 345                 350
Glu Pro Tyr Ile Ile Asp Pro Val Ala Asp Lys Glu Glu Ala Lys His
            355                 360                 365
Glu Tyr Gly Leu Glu Phe Asp Asp Leu Ser Lys Met Val Asn Leu Asp
370                 375                 380
Ala Ile Ile Ile Ala Val Ser His Glu Gln Phe Lys Asp Ile Thr Lys
385                 390                 395                 400
Gln Gln Phe Asp Arg Leu Tyr Ala His Asn Ser Arg Lys Ile Ile Phe
                405                 410                 415
Asp Ile Lys Gly Ser Leu Asp Lys Ser Glu Phe Glu Lys Asp Tyr Ile
            420                 425                 430
Tyr Trp Arg Leu
```

<210> SEQ ID NO 8
<211> LENGTH: 323
<212> TYPE: PRT
<213> ORGANISM: Francisella tularensis

<400> SEQUENCE: 8

```
Val Ala Tyr Asp Asn Val Lys Phe Pro His Gly Ser Phe Phe Leu Val
1               5                   10                  15

Thr Gly Gly Ala Gly Phe Ile Gly Ser Asn Leu Cys Glu Val Leu Leu
            20                  25                  30

Ser Lys Gly Tyr Arg Val Arg Cys Leu Asp Asp Leu Ser Asn Gly His
        35                  40                  45

Tyr His Asn Val Glu Pro Phe Leu Thr Asn Ser Asn Tyr Glu Phe Ile
    50                  55                  60

Lys Gly Asp Ile Arg Asp Leu Asp Thr Cys Met Lys Ala Cys Glu Gly
65                  70                  75                  80

Ile Asp Tyr Val Leu His Gln Ala Ala Trp Gly Ser Val Pro Arg Ser
                85                  90                  95

Ile Glu Met Pro Leu Val Tyr Glu Asp Ile Asn Val Lys Gly Ala Leu
            100                 105                 110

Asn Met Leu Glu Ala Ala Arg Gln Asn Asn Val Lys Lys Phe Val Tyr
        115                 120                 125

Ala Ser Ser Ser Ser Val Tyr Gly Asp Glu Pro Asn Leu Pro Lys Lys
    130                 135                 140

Glu Gly Arg Glu Gly Asn Val Leu Ser Pro Tyr Ala Phe Thr Lys Lys
145                 150                 155                 160

Ala Asn Glu Glu Trp Ala Arg Leu Tyr Thr Lys Leu Tyr Gly Leu Asp
                165                 170                 175

Thr Tyr Gly Leu Arg Tyr Phe Asn Val Phe Gly Arg Arg Gln Asp Pro
            180                 185                 190

Asn Gly Ala Tyr Ala Ala Val Ile Pro Lys Phe Ile Lys Gln Leu Leu
        195                 200                 205

Asn Asp Glu Ala Pro Thr Ile Asn Gly Asp Gly Lys Gln Ser Arg Asp
    210                 215                 220

Phe Thr Tyr Ile Glu Asn Val Ile Glu Ala Asn Leu Lys Ala Cys Leu
225                 230                 235                 240

Ala Asp Ser Lys Tyr Ala Gly Glu Ser Phe Asn Ile Ala Tyr Gly Gly
                245                 250                 255

Arg Glu Tyr Leu Ile Asp Leu Tyr Tyr Asn Leu Cys Asp Ala Leu Gly
            260                 265                 270

Lys Lys Ile Glu Pro Asn Phe Gly Pro Asp Arg Ala Gly Asp Ile Lys
        275                 280                 285

His Ser Asn Ala Asp Ile Ser Lys Ala Arg Asn Met Leu Gly Tyr Asn
    290                 295                 300

Pro Glu Tyr Asp Phe Glu Leu Gly Ile Lys His Ala Val Glu Trp Tyr
305                 310                 315                 320

Leu Ile Asn
```

<210> SEQ ID NO 9
<211> LENGTH: 409
<212> TYPE: PRT
<213> ORGANISM: Francisella tularensis

<400> SEQUENCE: 9

```
Val Tyr Ile Lys Lys Val Ser Phe Lys Ile Leu Tyr Leu Tyr Leu Leu
 1               5                   10                  15

Ala Phe Cys Ile Ile Phe Ser Leu Glu Phe Lys Phe Ala Ile Leu Asn
             20                  25                  30

Ile Ile Val Tyr Leu Pro Ala Cys Ile Leu Gly Phe Leu Ala Leu Lys
             35                  40                  45

Lys Leu Phe Val Gly Asn Ile Val Lys Gln Leu Ala Phe Leu Phe
 50                  55                  60

Phe Phe Phe Phe Leu Ser Met Ile Tyr Leu Ile Val Gln Ile Ile
 65                  70                  75                  80

Leu Leu Asp Ala Ala Ser Leu Phe Pro Gln Phe Leu Phe Asn Ile Leu
                 85                  90                  95

Ile Ala Ile Gly Phe Cys Asn Phe Ile Phe Val Ser Tyr Asp Asn Asn
                100                 105                 110

Glu Asn Tyr Phe Phe Asn Met Ser Lys Ile Ile Phe Phe Val Thr Phe
            115                 120                 125

Leu Gln Ser Ile Phe Val Phe Leu Ser Arg Tyr Tyr Ile Phe Leu Asn
    130                 135                 140

Asp Trp Ile Phe Phe Leu Val Lys Lys Gly Asn Ile Glu Ile Ser
145                 150                 155                 160

Asn Val Ile Glu Tyr Lys Leu Arg Val Phe Gly Leu Ser Asn Ala Gly
                165                 170                 175

Gly Asp Gly Leu Gly Phe Ser Ile Thr Ile Gly Leu Cys Phe Ser Ile
                180                 185                 190

Phe Tyr Phe Ile Lys Tyr Ile Lys Gly Lys Ser Ile Phe Thr Lys Leu
    195                 200                 205

Met Leu Phe Val Pro Leu Ile Leu Ile Val Phe Ser Asn Ile Phe Ile
210                 215                 220

Ser Arg Thr Ser Leu Leu Thr Ser Ser Leu Ile Leu Leu Ile Thr Ile
225                 230                 235                 240

Phe Tyr Ile Tyr Ile Lys Lys Glu Lys Leu Leu Phe Ile Ile Ile Leu
                245                 250                 255

Ala Leu Phe Phe Leu Ser Ile Trp Ile Leu Phe Lys Leu Asn Leu Asn
            260                 265                 270

Leu Ser Trp Ala Phe Glu Asn Ile Tyr Ser Tyr Ile Gln Ser Gly Asp
    275                 280                 285

Phe Ser His Gly Ser Leu Ser Val Leu Ile Asn Lys Met Leu Phe Val
    290                 295                 300

Pro Asp Asn Leu Leu Thr Trp Ile Phe Gly Cys Glu Asp Val Ser Asn
305                 310                 315                 320

Thr Asp Ile Gly Tyr Ile Lys Tyr Leu Tyr Tyr Gly Ile Ile Phe
                325                 330                 335

Ser Met Phe Phe Tyr Ile Leu Ile Ile Phe Leu Tyr Phe Glu Met Arg
            340                 345                 350

Lys Cys Phe Ile Phe Ser Glu Tyr Arg Ser Leu Phe Leu Leu Leu
            355                 360                 365

Ile Val Cys Leu Val Phe Gln Ala Lys Ile Ile Phe Leu Thr Val Gly
            370                 375                 380

Leu Phe Thr Lys Leu Thr Ile Ile Leu Phe Ile Phe Ser Leu Lys Glu
385                 390                 395                 400

Asn Ser Phe Thr Thr Arg Ser Val Ile
                405
```

<210> SEQ ID NO 10

```
<211> LENGTH: 366
<212> TYPE: PRT
<213> ORGANISM: Francisella tularensis

<400> SEQUENCE: 10

Leu Lys Arg Phe Val His Leu Ile Ile Asn Leu Asn Gln Gly Gly Ala
1               5                   10                  15

Glu Thr Met Leu Tyr Lys Leu Cys Lys Ser Met Asp Lys Ser Ile Tyr
            20                  25                  30

His Ile Thr Ile Ile Ser Leu Met Gly Arg Gly Val Phe Ala Asn Lys
        35                  40                  45

Leu Glu Ala Tyr Gly Val Lys Val Tyr Thr Leu Asn Leu Asn Lys Phe
50                  55                  60

Asn Val Leu Phe Val Leu Phe Lys Tyr Ile Lys Ile Arg Arg Ile
65                  70                  75                  80

Lys Pro Asp Val Ile His Ala Trp Met Tyr His Ala Asn Val Ile Ser
                85                  90                  95

Ile Leu Cys Lys Pro Phe Tyr Arg Lys Thr Lys Tyr Ile Asn Ser Ile
            100                 105                 110

Arg Met Gly Leu Glu Asn Tyr Asp Gly His Lys Asn Leu Thr Lys Phe
        115                 120                 125

Met Ile Lys Leu Asn Ala Lys Phe Ser Lys Phe Ser Asp Leu Thr Leu
    130                 135                 140

Asn Asn Ser Lys Lys Ser Leu Glu Asp His Gln Asn Ile Gly Phe Lys
145                 150                 155                 160

Asn Gln Cys Phe Ile Ala Asn Gly Phe Asp Lys Asp Val Phe Lys Pro
                165                 170                 175

Ser Phe Leu Lys Tyr Glu Lys Phe Arg Leu Asn Asn Asp Leu Asp Asp
            180                 185                 190

Asn Val Lys Ile Ile Gly Ile Ile Ala Arg Asn His Ala Asp Lys Asn
        195                 200                 205

Ile Ser Arg Phe Leu Gln Ile Ala Asn Leu Leu Lys Ser Asn Pro
    210                 215                 220

Ser Leu Arg Phe Leu Ile Ala Gly Arg Glu Cys Ser Lys Ile Asp Ile
225                 230                 235                 240

Gly Ser Tyr Leu Asp Asn Lys Ser Asn Val Asn Lys Phe Phe Val Phe
                245                 250                 255

Glu Ser Val Asp Ser Ser Glu Tyr Leu Pro Val Leu Asp Leu Tyr Leu
            260                 265                 270

Ser Thr Ser Lys Val Glu Gly Phe Pro Asn Ile Leu Ala Glu Ala Met
        275                 280                 285

Leu Cys Glu Val Pro Ile Val Ala Ser Asn Val Gly Asp Cys Lys Asp
    290                 295                 300

Ile Leu Asn Gly Tyr Gly Glu Val Phe Glu Leu Ser Gln Gly Asn Lys
305                 310                 315                 320

Glu Ile Ile Glu Lys Ile Met Lys Val Leu Glu Thr Thr Val Val Met
                325                 330                 335

Lys Lys Arg Met Arg Glu Tyr Ile Ile Asn Asn Phe Ser Ile Glu Ala
            340                 345                 350

Ile Leu Glu Lys His Glu Lys Leu Tyr His Glu Gly Ser Val
        355                 360                 365

<210> SEQ ID NO 11
<211> LENGTH: 628
<212> TYPE: PRT
<213> ORGANISM: Francisella tularensis
```

<400> SEQUENCE: 11

```
Met Cys Gly Val Val Gly Phe Tyr Ser Phe Asn Lys Glu Glu Gly Phe
1               5                   10                  15
Asp Ser Ile Ile Asn Gln Ser Leu Leu Ser Ile Lys His Arg Gly Ser
            20                  25                  30
Asp Asp Ser Gly Tyr Trp Cys Asp Asn Gln Val Thr Leu Gly His Thr
        35                  40                  45
Arg Leu Ser Ile His Asp Ile Thr Asn Ala Gly His Gln Pro Met Leu
    50                  55                  60
Ser Asn Ser Gly Asn Thr Ala Ile Val Phe Asn Gly Glu Ile Tyr Asn
65                  70                  75                  80
Tyr Leu Ser Ile Lys Asn Gln Leu Leu Ser Glu Tyr Ser Asn Leu Lys
                85                  90                  95
Phe Lys Ser Asn Ser Asp Thr Glu Val Leu Val Asn Ala Ile Glu Leu
            100                 105                 110
Trp Gly Ile Asp Lys Thr Leu Glu Lys Cys Ile Gly Met Phe Ala Phe
        115                 120                 125
Gly Val Tyr Ser Arg Lys Thr Ser Cys Leu Ile Leu Ala Arg Asp Arg
    130                 135                 140
Phe Gly Glu Lys Pro Leu Tyr Phe Gly Ile Gln Asn Gly Ile Leu Gly
145                 150                 155                 160
Phe Ala Ser Glu Leu Lys Ala Leu Lys Pro Leu Lys Glu Cys Gly Trp
                165                 170                 175
Arg Phe Asp Ile Asp Arg Asp Ala Leu Ala Thr Tyr Met Arg Tyr Ala
            180                 185                 190
Tyr Val Pro Thr Pro Tyr Ser Ile Tyr Lys Asn Ile Ser Lys Leu Asn
        195                 200                 205
Val Gly Ser Tyr Ile Lys Phe Asp Ala Lys Gly Asn Ser Lys Glu Tyr
    210                 215                 220
Lys Tyr Trp Asp Ser Lys Lys Val Leu Asp Ser Glu Lys Tyr Lys Asp
225                 230                 235                 240
Ser Tyr Asp Gln Ala Ile Leu Asp Leu Glu Ile Lys Leu Lys Ser Thr
                245                 250                 255
Leu Ser Ile Gln Met Gln Ser Asp Val Pro Leu Gly Ala Phe Leu Ser
            260                 265                 270
Gly Gly Ile Asp Ser Thr Thr Val Val Ala Leu Met Gln Ser Met Ser
        275                 280                 285
Lys Asp Lys Ile Asn Thr Phe Ser Ile Gly Phe Asn Gln Lys Glu Tyr
    290                 295                 300
Asn Glu Ala Glu His Ala Arg Ala Val Ala Lys His Ile Gly Thr Asn
305                 310                 315                 320
His Thr Asp Met Tyr Val Thr Glu Arg Asp Ala Leu Asp Val Ile Pro
                325                 330                 335
Lys Leu Ala Gly Ile Tyr Asp Glu Pro Phe Ala Asp Ser Ser Gln Ile
            340                 345                 350
Pro Thr Tyr Leu Val Ser Lys Ile Ala Lys Ser Lys Val Thr Val Ala
        355                 360                 365
Leu Ser Gly Asp Ala Gly Asp Glu Leu Phe Gly Gly Tyr Asn Arg Tyr
    370                 375                 380
Phe Leu Ala Pro Asn Ile Ala Lys Lys Ile Lys Phe Ala Lys Leu Leu
385                 390                 395                 400
Lys Tyr Ala Pro Asp Ala Trp Ile Lys Lys Ala Glu Ile Leu Asn Phe
                405                 410                 415
```

Gly Lys Phe Ala Leu Leu Ala Asp Lys Leu Leu Lys Leu Lys Arg Val
                420                 425                 430

Leu Glu Lys Ala Lys Thr Asn Lys Glu Leu Tyr Val Leu Leu Cys Ser
            435                 440                 445

Gln Ile Asn Asp Thr Ser Phe Val Leu Gly Ala Lys Glu Tyr Asp Ile
450                 455                 460

Leu Arg Asp Lys Asn Ile Tyr Asp Ile Pro Gln Leu Ser Phe Gln Glu
465                 470                 475                 480

Trp Met Met Phe Val Asp Ser Asn Thr Tyr Met Ile Asp Asp Ile Leu
                485                 490                 495

Val Lys Val Asp Arg Ala Ala Met Ala Asn Ser Leu Glu Thr Arg Val
                500                 505                 510

Pro Phe Leu Asp His Asn Ile Tyr Glu Phe Ala Tyr Ser Leu Pro Ile
            515                 520                 525

Asp Tyr Lys Ile Gln Arg Gly Asn Gly Lys Arg Ile Leu Lys Asp Leu
530                 535                 540

Leu Tyr Lys Tyr Val Pro Glu Ser Leu Val Asn Arg Ser Lys Met Gly
545                 550                 555                 560

Phe Gly Ile Pro Leu Ala Lys Trp Leu Arg Glu Asp Leu Arg Glu Trp
                565                 570                 575

Ala Asp Asn Leu Leu Asp Tyr Ser Lys Ile Asp Lys Gln Gly Tyr Leu
            580                 585                 590

Ser Pro Glu Val Val Gln Lys Tyr Trp Gln Glu His Leu Ser Gly Lys
            595                 600                 605

Arg Asn Trp Gln Ala Ile Leu Trp Asn Ile Leu Ile Phe Gln Glu Trp
            610                 615                 620

Leu Asp Asn Glu
625

<210> SEQ ID NO 12
<211> LENGTH: 360
<212> TYPE: PRT
<213> ORGANISM: Francisella tularensis

<400> SEQUENCE: 12

Met Ser Lys Val Asn Val Thr Lys Pro Tyr Leu Pro Asp Ile Asn Lys
1               5                   10                  15

Tyr Lys Ser Tyr Val Asn Lys Ile Tyr Lys Asn Gly Trp Leu Thr Asn
                20                  25                  30

Asn Gly Pro Leu Val Gln Glu Leu Glu Lys Arg Leu Ala Lys Tyr Leu
            35                  40                  45

Gly Val Lys Asn Ile Val Leu Val Ser Asn Gly Thr Ile Ala Leu Glu
        50                  55                  60

Ile Ala Tyr Arg Ala Leu Gly Val Lys Gly Ser Ala Ile Thr Thr Pro
65                  70                  75                  80

Phe Ser Phe Val Ala Thr Thr Ser Ser Leu Val Ser Asn Asn Val Lys
                85                  90                  95

Pro Val Phe Val Asp Ile Asp Glu Asn Thr Leu Ser Ile Asp Val Ser
            100                 105                 110

Lys Ile Lys Tyr Ala Ile Glu Glu Asp Thr Ser Ala Ile Val Pro Val
        115                 120                 125

His Val Phe Gly Asn Gly Cys Glu Val Glu Lys Ile Asp Met Leu Ala
    130                 135                 140

Lys Lys His Asn Leu Lys Val Ile Tyr Asp Ala Ala His Ala Phe Asp
145                 150                 155                 160

Val Lys Tyr Lys Gly Glu Ser Ile Leu Asn Tyr Gly Asp Ile Ser Thr
            165                 170                 175

Leu Ser Phe His Ala Thr Lys Ile Phe His Ser Ile Glu Gly Gly Ala
            180                 185                 190

Leu Ile Ile Asn Asp Asp Ser Leu Val Glu Lys Val Arg Tyr Phe Ile
            195                 200                 205

Asn Phe Gly Ile Glu Ser Ser Glu Ser Ile Pro Tyr Leu Gly Thr Asn
210                 215                 220

Ala Lys Met Asn Glu Phe Glu Ala Ala Met Gly Leu Cys Val Leu Asp
225                 230                 235                 240

Asp Ile Ile Glu Ile Lys Ser Lys Arg Lys Val Ile Thr Glu Ile Tyr
            245                 250                 255

Glu Ala Gly Leu Asp Gly Leu Val Lys Phe Gln Glu Gln Asn Gln His
            260                 265                 270

Ser Ser Arg Asn Tyr Ser Tyr Phe Pro Val Ile Phe Arg Thr Glu Glu
            275                 280                 285

Glu Leu Leu Arg Val Gln Lys Ala Leu Ile Gln Asn Asp Ile Ile Ser
            290                 295                 300

Arg Arg Tyr Phe Tyr Pro Ser Leu Asp Ser Leu Ser Tyr Ile Glu Pro
305                 310                 315                 320

Lys Gln Tyr Met Pro Ile Ser Arg Asp Ile Ser Lys Arg Ile Leu Cys
            325                 330                 335

Leu Pro Ile Tyr Ala Glu Leu Glu Asp Asp Lys Ile Asn Lys Ile Ile
            340                 345                 350

Asn Asn Ile Lys Glu Val Ser Ser
            355                 360

<210> SEQ ID NO 13
<211> LENGTH: 241
<212> TYPE: PRT
<213> ORGANISM: Francisella tularensis

<400> SEQUENCE: 13

Met Lys Lys Ile Phe Val Val Thr Asp Asn Arg Thr Ile Leu Ser Asp
1               5                   10                  15

Phe Lys Asn Ile Ile Gly Ser Lys Asn Asp Val Gln Val Asp Tyr Phe
            20                  25                  30

Cys Ser Phe Lys Ser Gln Thr Ser Phe Ala Lys Glu Ile Tyr Asn Ser
        35                  40                  45

Glu Ile Lys Pro Ile Asp Met Lys Lys Asn Gly Asn Asp Leu Ile Gly
    50                  55                  60

Lys Tyr Asp Leu Gly Phe Ser Cys His Ser Lys Gln Leu Phe Pro Ala
65                  70                  75                  80

Lys Leu Val Asn Ser Val Leu Cys Ile Asn Ile His Pro Gly Leu Asn
                85                  90                  95

Pro Tyr Asn Arg Gly Trp Phe Pro Gln Val Phe Ser Ile Ile Asn Lys
            100                 105                 110

Leu Pro Ile Gly Ala Thr Ile His Val Met Asp Glu Glu Ile Asp His
            115                 120                 125

Gly Asp Ile Ile Ile Gln Glu Glu Val Glu Val Asn Ser Phe Glu Asn
130                 135                 140

Ser Phe Asp Val Tyr Ala Lys Val Gln Lys Lys Glu Val Glu Leu Phe
145                 150                 155                 160

Thr Lys Val Ile Asp Asp Ile Leu Asn Asn Lys Phe Thr Arg Ile Lys
                165                 170                 175

```
Pro Asn Ser Glu Gly Asn Tyr Asn Ser Ile His Asp Tyr Lys Asn Met
            180                 185                 190

Cys Glu Ile Asp Leu Asp Lys Ile Val Thr Met Arg Glu Ala Ile Asp
            195                 200                 205

Tyr Leu Arg Ala Met Thr His Pro Pro Tyr Lys Asn Ser Tyr Phe Ile
            210                 215                 220

Asp Glu His Gly Asn Lys Val Phe Val Ala Leu Glu Leu Glu Lys Ile
225                 230                 235                 240

Ser
```

```
<210> SEQ ID NO 14
<211> LENGTH: 495
<212> TYPE: PRT
<213> ORGANISM: Francisella tularensis

<400> SEQUENCE: 14

Met Ser Leu Lys Lys Asn Thr Ile Ser Asn Tyr Ile Thr Gln Leu Tyr
1               5                   10                  15

Thr Ser Leu Ile Gly Ile Val Ile Leu Pro Leu Tyr Leu Gln His Leu
            20                  25                  30

Ser His Asp Ala Phe Gly Leu Ile Gly Phe Phe Thr Val Phe Gln Thr
        35                  40                  45

Trp Leu Arg Leu Leu Asp Val Gly Ile Thr Pro Thr Leu Ser Arg Glu
    50                  55                  60

Val Ala His Val Arg Gly Ser Thr Asp Asp Tyr His Tyr Leu Arg Lys
65                  70                  75                  80

Leu Val Arg Ser Leu Glu Leu Phe Phe Ile Ile Val Gly Val Leu Val
                85                  90                  95

Phe Ile Val Ile Ser Thr His Ser Arg Tyr Ile Ser Thr Ser Trp Leu
            100                 105                 110

His Ile Gly Ser Leu Asp Ala Asp Ser Val Ser Val Cys Ile Ala Leu
        115                 120                 125

Met Gly Leu Met Phe Ala Leu Arg Trp Val Ser Asp Leu Tyr Gly Gly
    130                 135                 140

Gly Leu Arg Gly Phe Glu Arg Gln Val Leu Tyr Asn Asn Leu Ser Ile
145                 150                 155                 160

Ile Gln Thr Thr Leu Gln Phe Ile Gly Gly Leu Leu Phe Ile Cys Tyr
                165                 170                 175

Val Ser Thr Asn Ile Met Tyr Tyr Phe Val Tyr Gln Thr Ile Ile Ala
            180                 185                 190

Ile Leu Tyr Leu Val Cys Ile Ala Ile Ala Phe Tyr Lys Ile Leu Pro
        195                 200                 205

Ser Ser Phe Ser Val Gly Leu Arg Phe Asp Phe Lys Ile Ile Arg Lys
    210                 215                 220

Val Leu Pro Phe Ala Leu Gly Ile Ala Tyr Ser Thr Thr Val Trp Ile
225                 230                 235                 240

Ile Val Thr Gln Ser Asp Lys Leu Val Phe Ser His Val Leu Pro Leu
                245                 250                 255

Ser Glu Tyr Gly Tyr Leu Ser Leu Leu Ile Val Ile Ser Ser Ala Val
            260                 265                 270

Thr Ile Leu Ser Ser Pro Ile Ser Ile Ala Ile Gln Pro Arg Met Thr
        275                 280                 285

Met Leu Leu Ala Gln Gln Asn Val Lys Gly Met Glu Ser Leu Tyr Leu
    290                 295                 300
```

-continued

Lys Ser Ser Leu Ile Ser Ile Thr Phe Leu Ser Ala Val Val Thr Cys
305                 310                 315                 320

Val Leu Met Tyr Ser His Gln Leu Leu Gln Ser Trp Thr Gly Ser Met
            325                 330                 335

Glu Ile Ala Asn Trp Gly Ser Asn Ile Leu Asn Ile Tyr Val Leu Ser
        340                 345                 350

Ala Ser Ile Ile Cys Ile Ile Ser Phe Gln Tyr Phe Leu Gln Tyr Ala
    355                 360                 365

Tyr Gly Lys Leu Lys Leu His Asn Thr Tyr Asn Thr Ile Ser Leu Val
370                 375                 380

Phe Phe Ala Pro Ile Val Ile Tyr Thr Ala Tyr Asn Tyr Gly Val Tyr
385                 390                 395                 400

Thr Thr Ala Leu Leu Trp Leu Gly Tyr Ala Ile Val Gly Leu Ile Ile
            405                 410                 415

Trp Met Pro Ile Val His His Val Phe Ala Lys Gly Ile Asn Arg Tyr
        420                 425                 430

Phe Phe Ile Asn Leu Ala Val Ile Thr Ile Val Cys Phe Leu Leu Ser
    435                 440                 445

Leu Ile Phe Lys Gly Trp Tyr Ile Tyr Pro Ser Lys Ile Gly Leu Val
450                 455                 460

Glu Leu Ile Leu Ile Gly Phe Ala Phe Leu Phe Ile Gln Ile Cys Ile
465                 470                 475                 480

Glu Tyr Val Leu Phe Arg Tyr Lys Val Leu Arg Cys Ile Asp Asp
            485                 490                 495

<210> SEQ ID NO 15
<211> LENGTH: 286
<212> TYPE: PRT
<213> ORGANISM: Francisella tularensis

<400> SEQUENCE: 15

Met Ile Lys Val Ser Val Cys Val Met Thr Tyr Asn Gln Glu Lys Tyr
1               5                   10                  15

Ile Gly Gln Cys Leu Glu Ser Leu Val Thr Gln Glu Thr Asp Phe Asp
            20                  25                  30

Phe Glu Ile Ile Val Gly Asp Asp Phe Ser Thr Asp Gly Thr Arg Asp
        35                  40                  45

Val Ile Gln Glu Tyr Gln Lys Lys Tyr Pro Asp Ile Ile Lys Pro Val
    50                  55                  60

Phe Arg Asp Lys Asn Val Gly Ile Thr Glu Asn Ile Lys Glu Ile Tyr
65                  70                  75                  80

Phe Val Ala Asn Gly Glu Tyr Ile Ala His Met Asp Gly Asp Asp Tyr
                85                  90                  95

Ala Leu Pro Gly Lys Leu Gln Ile Gln Ala Asp Phe Leu Asp Asn Asn
            100                 105                 110

Pro Arg Cys Thr Gly Val Phe His Asn Ile Asn Ile Leu Tyr Pro Asn
        115                 120                 125

Gly Asn Ile Gln His Ser Arg Phe Ala Cys Ser Asn Lys Ser Ile Phe
    130                 135                 140

Asn Leu Ser Asp Thr Leu Arg Gly Val Ala Val Gly Ala Asn Ser Ser
145                 150                 155                 160

Lys Met Phe Arg Thr Ser Val Leu Asp Leu Ile Leu Pro Asp Ile
                165                 170                 175

Glu Leu Leu Asp Tyr Tyr Phe His Val Ile Thr Ala Glu Lys Gly Tyr
            180                 185                 190

```
Leu Ser Phe Leu Asn Ser Asn Glu Ser Tyr Ser Val Tyr Arg Lys Gly
        195                 200                 205

Ile Gly Ile Thr Ser Lys Ser Lys Glu Lys Ile Tyr Asn Thr Tyr Ala
210                 215                 220

Gly Leu Phe Glu Tyr Phe Leu Asp Arg Tyr Pro Glu Glu Lys Leu Asn
225                 230                 235                 240

Ile Cys Ile Pro Val Val Gln Met Ile Ile Ser Ala Ile Lys Gly Arg
                245                 250                 255

Cys Phe Ile Ser Ala Ile Arg Leu Phe Lys Ile Leu Ile Arg Ser Arg
                260                 265                 270

Cys Ile Pro Leu Val Ser Trp Phe Lys Tyr Arg Phe Glu Lys
                275                 280                 285

<210> SEQ ID NO 16
<211> LENGTH: 294
<212> TYPE: PRT
<213> ORGANISM: Francisella tularensis

<400> SEQUENCE: 16

Met Lys Gly Ile Ile Leu Ala Gly Gly Ser Gly Thr Arg Leu Tyr Pro
1               5                   10                  15

Leu Thr Leu Gly Val Ser Lys Gln Leu Leu Pro Val Tyr Asp Lys Pro
                20                  25                  30

Leu Leu Tyr Tyr Pro Leu Ser Val Leu Met Leu Ala Gly Ile Arg Glu
            35                  40                  45

Ile Leu Ile Ile Ser Thr Val Arg Asp Ile Ser Leu Ile Gln Glu Leu
        50                  55                  60

Leu Gly Asp Gly Ser Gln Phe Gly Ile Gln Leu Ser Tyr Lys Ile Gln
65                  70                  75                  80

Pro Ser Pro Asp Gly Leu Ala Gln Ala Phe Ile Leu Gly Glu Glu Phe
                85                  90                  95

Leu Ala Gly Asp Ser Ala Cys Leu Ile Leu Gly Asp Asn Ile Tyr Tyr
                100                 105                 110

Gly Gln Gly Met Thr Thr Met Leu Glu Ser Ala Arg Ala Gln Cys Gly
                115                 120                 125

Gly Pro Ala Gly Gly Ala Cys Val Phe Gly Tyr Tyr Val Asn Asp Pro
130                 135                 140

His Arg Tyr Gly Ile Val Glu Phe Asp Lys Gln Lys Asn Val Ile Ser
145                 150                 155                 160

Val Glu Glu Lys Pro Gln Asn Pro Lys Ser His Tyr Ala Ile Thr Gly
                165                 170                 175

Leu Tyr Phe Tyr Asp Asn Asn Val Val Glu Tyr Ala Lys Gln Val Lys
                180                 185                 190

Pro Ser Ala Arg Gly Glu Leu Glu Ile Thr Ser Leu Asn Glu Leu Tyr
            195                 200                 205

Leu Lys Glu Asn Lys Leu Asn Val Glu Leu Leu Gly Arg Gly Phe Ala
        210                 215                 220

Trp Leu Asp Ala Gly Thr His Asp Ser Leu Leu Glu Ala Gly Gln Tyr
225                 230                 235                 240

Val Ala Thr Ile Glu Lys Arg Gln Gly Leu Lys Ile Ala Cys Leu Glu
                245                 250                 255

Glu Ile Ala Trp Arg Lys Gly Phe Ile Ser Thr Gln Val Leu Ala
                260                 265                 270

Gln Ala Glu Lys Leu Ser Lys Thr Glu Tyr Gly Gln Tyr Leu Lys Asn
                275                 280                 285
```

```
Leu Ile Lys Asp Gly Leu
        290

<210> SEQ ID NO 17
<211> LENGTH: 348
<212> TYPE: PRT
<213> ORGANISM: Francisella tularensis

<400> SEQUENCE: 17

Met Thr Ser His Tyr Arg Asn Asp Asp Val Met Arg Asn Glu Lys Met
1               5                   10                  15

Asn Tyr Lys Pro Lys Asn Ile Leu Val Thr Gly Ala Ala Gly Phe Ile
            20                  25                  30

Gly Ser Asn Tyr Val Arg Met Met Leu Ser Arg Tyr Ser Asp Ile Lys
        35                  40                  45

Ile Ile Ser Tyr Asp Lys Leu Thr Tyr Ala Gly Ser Leu Asp Asn Leu
    50                  55                  60

Lys Asp Leu Asn Asn Glu His Asn His Thr Phe Ile Lys Gly Asp Ile
65                  70                  75                  80

Cys Asp Glu Val Leu Val Tyr Gln Thr Leu Lys Glu Tyr Lys Ile Asp
                85                  90                  95

Thr Ile Val His Phe Ala Ala Glu Ser His Val Asp Asn Ser Ile Ala
            100                 105                 110

Asn Pro Lys Val Phe Leu Glu Thr Asn Val Ile Gly Thr Phe Thr Leu
        115                 120                 125

Leu Asp Cys Ala Lys Arg Tyr Trp Leu Asp Glu Leu Gly Leu Glu Glu
    130                 135                 140

Thr Ser Cys Arg Phe His His Val Ser Thr Asp Glu Val Tyr Gly Thr
145                 150                 155                 160

Leu Ala Lys Asp Glu Pro Ala Phe Thr Glu Ile Lys Ala Tyr Glu Pro
                165                 170                 175

Asn Ser Pro Tyr Ser Ala Ser Lys Ala Gly Ser Asp His Ile Ser Arg
            180                 185                 190

Ala Tyr His His Thr Tyr Lys Leu Pro Val Thr Ile Ser Asn Cys Ser
        195                 200                 205

Asn Asn Tyr Gly Pro Tyr Gln His Arg Glu Lys Leu Ile Pro Val Val
    210                 215                 220

Ile Asn Ser Cys Ile Asn Tyr Lys Pro Ile Pro Val Tyr Gly Asp Gly
225                 230                 235                 240

Ser Asn Ile Arg Asp Trp Leu Tyr Val Glu Asp His Cys Asp Ala Ile
                245                 250                 255

Gln Thr Ile Val Glu Lys Gly Val Val Gly Glu Val Tyr Asn Ile Gly
            260                 265                 270

Gly Ile Asn Glu Val Asp Asn Leu Thr Leu Val Lys Thr Ile Cys Lys
        275                 280                 285

Leu Met Asp Glu Tyr Lys Pro Glu Asn Ala Pro His Ser Asn Leu Ile
    290                 295                 300

Thr Phe Val Glu Asp Arg Lys Gly His Asp Trp Arg Tyr Ala Ile Asp
305                 310                 315                 320

Asn Ser Lys Ile Gln Asn Glu Leu Gly Trp Lys Pro Ser Gln Asp Phe
                325                 330                 335

Asp Lys Met Phe Arg Gln Thr Ile Glu Phe Tyr Leu
            340                 345

<210> SEQ ID NO 18
<211> LENGTH: 126
```

```
<212> TYPE: PRT
<213> ORGANISM: Francisella tularensis

<400> SEQUENCE: 18

Met Pro Ser Tyr Ser Gln Asp Phe Arg Asp Ile Val Ile Asn Lys His
1               5                   10                  15

Glu Glu Gly Met Thr Glu Phe Glu Leu Ser Lys Phe Phe Asn Ile Asp
            20                  25                  30

Lys Arg Thr Val Val Ser Trp Ile Glu Phe Tyr Lys Arg Thr Gly Asp
        35                  40                  45

Tyr Ser Ser Lys Gln Gly Val Gly Cys Gly Arg Val Ala Ser Phe Thr
50                  55                  60

Asp Lys Thr Leu Ile Glu Gln Tyr Leu Ile Asp His Pro Asp Ala Ser
65                  70                  75                  80

Ala Leu Asp Ile Lys Glu Ala Leu Ala Pro Asp Ile Pro Arg Ser Thr
                85                  90                  95

Phe Tyr Asp Cys Leu Asn Arg Leu Gly Phe Ser Phe Lys Lys Arg Leu
            100                 105                 110

Gln Asn Ile Ser Lys Glu Lys Asn Met Lys Gly Trp Ser Ile
        115                 120                 125

<210> SEQ ID NO 19
<211> LENGTH: 468
<212> TYPE: PRT
<213> ORGANISM: Francisella tularensis

<400> SEQUENCE: 19

Met Ile Thr Pro Ile Ile Leu Ser Gly Gly Phe Gly Ser Arg Leu Trp
1               5                   10                  15

Pro Leu Ser Arg Glu Ala Ser Pro Lys Gln Phe Ile Gly Leu Val Asp
            20                  25                  30

Glu His Ser Leu Leu Glu Asn Thr Ile Lys Arg Leu Asp Asn Val Lys
        35                  40                  45

Asp Ile Thr Ser Pro Val Val Val Cys Asn Glu Ser His Arg Phe Gln
50                  55                  60

Val Ala Glu Val Leu Arg Lys Ile Asn Lys Lys Gly Asp Ile Leu Leu
65                  70                  75                  80

Glu Pro Leu Ala Arg Asn Thr Ala Pro Ala Ile Ala Leu Ala Ala Leu
                85                  90                  95

His Leu Ala Ile Asn Asp Pro Asn Thr Ile Met Leu Val Leu Ala Ala
            100                 105                 110

Asp His His Ile Glu Asn Leu Glu Ile Phe His Gln Ala Ile Glu Lys
        115                 120                 125

Ala Gln Gln Lys Val Ile Lys Asp Asp Ser Leu Val Thr Phe Gly Ile
    130                 135                 140

Thr Pro Thr Cys Pro His Glu Gly Tyr Gly Tyr Ile Lys Gln Gly Val
145                 150                 155                 160

Gln Thr Thr Val Asn Gly Val Tyr Lys Val Asp Lys Phe Val Glu Lys
                165                 170                 175

Pro Ser Val Val Val Ala Gln Glu Tyr Leu Asp Ser Gly Lys Tyr Tyr
            180                 185                 190

Trp Asn Ser Gly Met Phe Met Phe Thr Ala Arg Val Tyr Leu Glu Val
        195                 200                 205

Leu Glu Lys Leu Gln Pro Glu Ile Tyr Arg Gly Cys Glu Lys Thr Tyr
    210                 215                 220

Gln Lys Ser Gln Gln Asp Leu Asp Phe Val Arg Phe Asp Lys Gln Ser
```

```
                225                 230                 235                 240
            Phe Ala Leu Val Gln Ser Gln Ser Ile Asp Tyr Ala Val Met Glu Lys
                            245                 250                 255
            Ala Thr Asn Val Ala Ile Val Pro Met Gln Gln Ser Gly Trp Ser Asp
                        260                 265                 270
            Val Gly Ser Trp Asp Ser Leu Tyr Asp Ile Ala Ala Lys Asp Ser Cys
                    275                 280                 285
            Gly Asn Val Val Ile Gly Asp Val Ile Thr Ser Asn Val Lys Asn Ser
                290                 295                 300
            Tyr Leu Arg Ser His Asp Arg Leu Leu Ala Ala Val Gly Val Asn Asp
            305                 310                 315                 320
            Leu Ile Ile Val Glu Thr Ala Asp Ala Ile Leu Val Ala Asp Lys Asn
                            325                 330                 335
            Lys Thr Gln Asp Val Lys Lys Ile Val Glu Val Leu Lys Ile Gln Gln
                        340                 345                 350
            Arg Ser Glu Leu Leu Gln His Lys Gln Ile Tyr Lys Pro Trp Gly Ser
                    355                 360                 365
            Ala Thr Ile Leu Glu Asp Lys Ser Gly Tyr Lys Ile Gln Ala Ile Gln
                370                 375                 380
            Leu Glu Pro Gly Lys Lys Leu Ser Leu Gln Gln His Tyr His Arg Ser
            385                 390                 395                 400
            Glu His Trp Ile Val Ile Ser Gly Thr Ala Thr Val Thr Ile Gly Thr
                            405                 410                 415
            Thr Lys Ser Ile Val Arg Pro Asn Glu Ser Val Tyr Ile Lys Ile Gly
                        420                 425                 430
            Glu Ser His Arg Leu Glu Asn Asn Gly Lys Ile Pro Val Ile Leu Ile
                    435                 440                 445
            Glu Val Gln Val Gly Tyr Ile Ser Glu Asp Asp Ile Val Arg Leu
                450                 455                 460
            Asp Thr Ser Ser
            465

<210> SEQ ID NO 20
<211> LENGTH: 494
<212> TYPE: PRT
<213> ORGANISM: Francisella tularensis

<400> SEQUENCE: 20

Met Arg Gln Thr Ile Ile Lys Glu Ile Ile Lys Ser Ser Gly Val Lys
            1               5                   10                  15
            Phe Gly Thr Ser Gly Val Arg Gly Leu Val Ser Ala Met Thr Asp Lys
                        20                  25                  30
            Ile Cys Trp Leu Tyr Thr Lys Ala Phe Ile Gln Phe Leu Glu Gln Lys
                    35                  40                  45
            Tyr Ser Ile Ala Lys Gly Thr Lys Ile Ala Ile His Asp Leu Arg
                50                  55                  60
            Glu Ser Ser Pro Arg Ile Thr Val Val Lys Ala Ile Ile Asp
            65                  70                  75                  80
            Ser Gly His Glu Pro Ile Tyr Cys Gly Glu Ile Pro Ser Pro Ala Val
                            85                  90                  95
            Met Leu Tyr Gly Ile Ser Asn Gln Ile Pro Ser Val Met Val Thr Gly
                        100                 105                 110
            Ser His Ile Pro Glu Asp Arg Asn Gly Ile Lys Phe Asn Thr Pro Tyr
                    115                 120                 125
            Gly Glu Val Leu Lys Glu Asp Glu Glu Met Ile Val Ser Gln Thr Ile
```

```
              130                 135                 140
Ser Ile Asp Glu Ser Ile Phe Asp Lys Asn Gly Met Phe Leu Gln Lys
145                 150                 155                 160

Leu Glu Leu Pro Glu Pro Ser Lys Gln Ala Tyr Thr Gln Tyr Ile Asp
                165                 170                 175

Arg Tyr Val Asp Phe Phe Pro Asn Asn Cys Leu Ala Gly Lys Thr Ile
            180                 185                 190

Gly Leu Tyr Gln His Ser Ser Val Gly Arg Glu Ile Val Lys Glu Ile
        195                 200                 205

Leu Glu Lys Leu Gly Ala Lys Val Ile Leu Glu Phe Ser Glu Lys
210                 215                 220

Phe Val Ser Val Asp Thr Glu Ala Ile Arg Gln Glu Asp Val Lys Leu
225                 230                 235                 240

Ala Lys Gln Trp Ala Ser Lys Tyr Lys Val Asp Ser Ile Val Ser Thr
                245                 250                 255

Asp Gly Asp Ala Asp Arg Pro Leu Val Ser Asp Glu Tyr Gly Asn Trp
            260                 265                 270

Leu Lys Gly Asp Ile Leu Gly Val Leu Thr Ala Lys Tyr Leu Gln Ala
        275                 280                 285

Asn Val Ile Val Thr Pro Val Ser Ser Asn Thr Val Ala Glu Lys Ile
290                 295                 300

Gly Tyr Phe Ser Asn Val Ile Arg Thr Lys Ile Gly Ser Pro Tyr Val
305                 310                 315                 320

Ile Ala Ala Met Asn Glu Leu Leu Ser Asn Asn Gln Asn Ala Val Val
                325                 330                 335

Gly Tyr Glu Ala Asn Gly Gly Phe Leu Leu Ala Ser Asp Ile Cys Lys
            340                 345                 350

Asp Asp Lys Thr Leu Lys Ala Leu Pro Thr Arg Asp Ala Val Ile Pro
        355                 360                 365

Met Leu Ala Val Met Met Leu Ser Ile Asn Ser Asn Lys Thr Val Ser
370                 375                 380

Glu Leu Leu Phe Asp Leu Pro Ser Arg Tyr Thr Ala Ser Ser Lys Ile
385                 390                 395                 400

Asp Asp Phe Ala Ser Glu Lys Ser Gln Glu Ile Leu Lys Ser Ile Leu
                405                 410                 415

Ala Gly Glu Ser Asp Leu Leu Asp Lys Ile Ile Ser Glu His Phe Asp
            420                 425                 430

Gly Lys Asn Ser Ile Glu Asn Ile Asp Thr Thr Asp Gly Val Arg Val
        435                 440                 445

Thr Leu Thr Asn Gln Asp Ile Ile His Leu Arg Pro Ser Gly Asn Ala
450                 455                 460

Pro Glu Leu Arg Cys Tyr Thr Glu Ala Ala Ser Asp Glu Gln Ala Lys
465                 470                 475                 480

Ser Leu Asn Gln Tyr Cys Val Asp Leu Ile Asn Lys Asn Ile
                485                 490
```

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
ataatgaaat caatccacga g                                         21

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ccagccagtc agtcccacag                                                   20

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
tgtcttagat atggggcaac c                                                 21

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
acaaatatca aatcctaaca catc                                              24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
tagaagcagc tgcgataggt agac                                              24

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26
ttaaataaaa actgaggaaa ca                                                22

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
atggtatttt aatcaagtgt                                                   20

<210> SEQ ID NO 28
<211> LENGTH: 17
<212> TYPE: DNA
<213> ORGANISM: Artificial Sequence
<220> FEATURE:
<223> OTHER INFORMATION: Synthetic oligonucleotide

```
<400> SEQUENCE: 28
ctagtatgcc ccagagt                                                  17

<210> SEQ ID NO 29
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 29
tggtgcgaca atcaagtta                                                19

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 30
agaagttcct cctcagtc                                                 18

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
agaaattaag agcaaaagga aagt                                          24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
atctcaaagt caaaatcagt ctct                                          24

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
tacgatattg tcctctccga ttag                                          24

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
tagttgcgac atattgacct g                                             21

<210> SEQ ID NO 35
<211> LENGTH: 23
<212> TYPE: DNA
```

```
<213> ORGANISM: Artificial Sequence
<220> FEATURE:
<223> OTHER INFORMATION: Synthetic oligonucleotide

<400> SEQUENCE: 35
aggcaggtca atatgtcgca act                                              23

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
tttccgcaac acttcagcaa ctt                                              23

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
gctatggcca ctatcacgag agg                                              23

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
tatacttgct tgcccactgc ttag                                             24

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
accgtagtga gcattggatt gt                                               22

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 40
actagggcct ctgaccgttc tc                                               22

<210> SEQ ID NO 41
<211> LENGTH: 22401
<212> TYPE: DNA
<213> ORGANISM: Francisella tularensis

<400> SEQUENCE: 41
tcttttataa atgatgatag caaacaaaaa ataataggtt ctgtgcacaa aaaacttaaa      60
ttatattgaa aatagctaaa ccgctgttat ttaagatttg aaaagcaata aatatcaatg     120
```

-continued

```
gtttagcaaa tgaattatca tataaaagaa gtattctggt caattatttt atcattctta      180
aaatcacaaa aaggtataca taccaatgat gaagccaaat taagattgtt tattgaagct      240
gtattttatg tgttacgtac aggctgtcaa tggagaatgt taccatttta ttatggtaaa      300
tatagatcaa tacataagcg ttttaaagat tggtgtgata agatatatt ttctagatta       360 tttaaatcag tacaaaaccc tgatttacaa gaagtcatgc ttgattcaac aatagcaaga      420
gcacatgctt gtgctacggg atatgataaa gatgataacc aagcaattgg tagatcagtt      480
ggtaggataa ccactaaaat ccatgctatg actgatgctt taggtaatcc aatagaaata      540
ttgttgtcag aggataaaac tcatgatagt aaagtagcta tagatttact aaaaaatgta      600
tataatacaa aagttatcgc tgatagagca tatcattcta atgaaatcag gcagcatatt      660
caaggtatat cctctgaagc tgttatccct tgtaaatcaa atactctaaa ccatatacct      720
tttgatagtc atgtatataa agaaagacat ttgatagaga atttctttc taaaattaag       780 cattttagaa gagtattctc tagatttgat aaaaccattt tagcatatat aggaatgatt      840
aaattagctt gtacttttat ttggttacga tgaatattta ttttgtgca cagaacctaa       900 tttgcatttt tgtgcacaaa gaaaatttt ttgatataat agactttaat aggatatttt       960
ctaaaaatta acaaatgtct ttctacgata atagaacgct taatttcgtg gtaataatag     1020
ttttaactat tattactgtt aattggactt tctatatttt caagcaagat gttaatttac     1080
attttttact tgcattagtt ttgctgagat gcttgtcatc ttttttacta cttagagatt     1140
atatggctag ttggcgtaag tcgactcaaa aaactttttt acgtaaggct tttattaatt     1200
tgccagtatt tttcatagtg gcattatttt tttatggcaa agtcactttt tcgttgatat     1260
tctctgagtt tttatttat gttttttga tcagtttaag tgtctacttt tattggtatt       1320
tgatgaacag aggatcagtg gataaaagta aaactgcggt tatttatggt gcaggtgctg     1380
caggaacaaa gattgctcaa gaacttgctt ctgctggtta tcgcatcaaa tgttttgttg     1440
atgacaatga aactttacaa aaaagaagta ttgatagtaa aaaggttcta tctaaagctg     1500
aattaacaaa actattgcta tctagtagat ttgacctttt ggttattgca ttgccaagaa     1560
atgcaaacca agtagtcaaa aatatatata agaatttga aaaggatttt aatcagatta      1620
gaattatgcc gcctcttgag gaaattcttc aagatgagaa ttttatgtca cagttgaagc     1680
ctgtttcact ctatgatcta ttagcgcgtg atactaagag tttagataaa gaatctatct     1740
ctaattttat caaaaataag gtggtgctag tcacaggagc tggaggtagt ataggttctg     1800
aaatagtaca tcaatgtatc aagtatcagg caaaagagtt gatattggtt gatcatagtg     1860
agtttaactt atataaaatt actgaggagt gtagtcattt taatatcaat agtgtgctat     1920
gttctgtttg tgatagaaaa gcattggctg aggtttttca aaagtatact ccaaatatag     1980
tatttcatgc tgctgcctac aagcatgttc ccttagttga ggagaatatc tctagagcaa     2040
ttagaaataa tatcttaggt actaagaatg ctatagatct ggctatagaa gctggtgttg     2100
agtcatttat attgatttcc actgataaag cagtgcgacc aacgaatgtt atggggcta      2160 ccaagagagt ttgtgagctg tatttacaga atgttgatcc caaaaatacc aagcttgctg     2220
cagtgcgttt tggtaatgtg cttggtagta gtggcagtgt gattccaaaa tttgaagagc     2280
aaataagaaa aggtggtcct gttacagtta ctcatcctga aattcacgt tatttatgt       2340 tgataccaga agcttgtgaa ctggtcctac aagctggtgc tattgcaaaa aattcagagg     2400
tctttgtctt agatatgggg caacctgtca agattattga tcttgctaaa caatttatta     2460
gactttctgg tagaggtgat attgatatta aaatagttgg tttgcgtcca ggagagaaac     2520
```

```
tttacgaaga gcttttgata gaggaagatg atgttagtac cgactataaa gatattttta    2580
ttggtagaag gacttttac gatattaata ctctaaacca agatattgaa tcgttgatca     2640
aggatgatgt tgatcagctt gtgatattaa agaaaattgt tccggaattt gaacatagat    2700
tgaatgggta gtggttttat gttttatgag gttttaaaa gattgcttga tattttactt     2760
tcttttatgg ggttgttgtt attaagtcct attttcttaa ttattatttt tatgataaag    2820
aaagattcaa aaggacctat attttttaaa caaaagcgct atggtaaaga taagcaattt    2880
ttttacatat ataagtttag aactatgtat gttgatactc caaaagatat gccaacgcac    2940
atgttacagg atccatcgaa atgtataact aaggttggag gattttttaag gaaatcatct   3000
ttagatgagt tgccacaaat tataaatatt ctaaaaggtg aaatgagcat cgtgggtcca    3060
agaccagcat tatggaatca agatgactta atagcacaaa gagataagta tggggcaaat    3120
gctgtgcctg tgggactgac tggctgggca cagattaatg gtagggatga attaccaata    3180
cctgataaag ctaaacttga tggtgattat gtaaaaaata aaagtacatg gtttgattta    3240
aaatgtatt ttttgacagt attttctgtt tttgccaaaa agggcgtcgt tgagggtggt    3300
actggagctt taggtaacaa agaggattta aagtagtatg aaaaaaagaa tcttagttac    3360
aggtttgagt agctatattg gtaactcatt tgcggctaaa tataactcag attttagtat    3420
cgataaaata tctttgcgcg atgtttcgtg ggcaaatata gacttaagtg gttatgatgc    3480
tgtattgcat gtcgctggaa ttgcccatac ttcaaggat cctaaactaa aagaaaaata    3540
ctataaaata aatacgcaat taacttatga tctggcaaaa caagctaaag atcaaggtgt    3600
tcgacagttt gtgtttttaa gtagtattat agtttatggt gatagtgcgc caataggtca    3660
acaaaaagtt ataactaaat ataccgaacc taaaccagat gattttttatg gagatagtaa    3720
gcttcaaact gaaattaagc taaatagcct ggctagtgat gactttaata ttgctataat    3780
cagaccacca atggtatatg gagaaggctc aaaaggcaac tatccaaagt tggttaaact    3840
tgcaaagtat acttttattt ttcctaatat taataaccaa agaagtgtta tatctataga    3900
taatttatct aaagagattg cagaaataat tttgcaaact aaacatggag ttttttctact    3960
tcaagataat gaatatttt gcacttcaca gtttataaaa aactatagaa aagatgtttt    4020
aggtaagaga acttatctga caaaaatttt taatccaatt ataagattgc ttgctaaaaa    4080
agtagatttt attaataaag ttttgggaa tttgacttat gagaagtaag ttattattca    4140
tagctaatga ttttgatatt gtaatatatc gtttcagaag agaagtaatc gagtcttttg    4200
ctgctaaaga gtatgagata gtactagtaa caccatattc taagaaagca gaggtttttt    4260
gtaaaagtct tggtgttaag tatataaatg ttgatataga tagacgaggc aaaaatcctt    4320
ttaaggattt gcttcttta tttaactatt tcaaatataa aaaaaagaa aaacctgatt    4380
acatttttag ctatacaatt aaaccaaatt tgtatgttgg gttagtgaat tgtttttta    4440
ggaagaagtt ttatccaaat gtaacaggct taggaagtgt ttttgctaat catggtattg    4500
ttcagaagtt tataatatct ttatataagt tatcatttaa aagcaccaca aaagtattct    4560
ttcagaatga gcaaaataaa aagttattta agctaagaa aataatcagt ggagaaaaat    4620
caatattatt accaggttct ggggtaaact tagatgaaaa taaatatgtt gactatccta    4680
aagaccaagg aatattaaaa ttcgtttttc ttggccgaat aatgaaagaa aaggggattt    4740
atgaattgtt agaagccttt gctatacttg agaaaaaata taaaaatatt agtcttgaca    4800
tttatggttt ttgtgatgaa aataaatcta ttttatggg aaaggttaat acgataaaat    4860
cagtaaaatt ttatggtttt actgataata ctaaagaaaa aatagctagt gcacatgcag    4920
```

```
ttgttttgcc atcttaccat gaaggaatgt caaatgtgct gttagaagca gctgcgatag    4980
gtagacctgt aattgcgtca gatattcctg ggtgtagaga aatttttgat gatggtctct    5040
ctggcttatc atgtaaccct aatgatgtga gttctttacg taactcatta gagcagttta    5100
taaatatgtc gtatactgat aaaatagcta tgagctataa agctagagct aagatagaaa    5160
aagattttga tagaagtatt gttgtcaatg catacttaca gcaaaattaa taataagggt    5220
ttaaattatg agtttatatg aggatatagt cgctaaaaga gaaaaggttt cattggttgg    5280
cttgggttat gttggtttac caatagctat tgcatttgca aaaaaaatag atgtgttagg    5340
atttgatatt tgtgaaacaa aagttcaaca ttataaggat ggttttgatc caacaaaaga    5400
agtaggagat gaggctgtca gaaatacgac aatgaaattt agttgtgatg aaacaagtct    5460
taaagagtgt aaatttcata ttgttgcagt tcctacacca gttaaagcag ataaaactcc    5520
tgatttgacg ccgattatta aggcaagtga gacggttggt aggaatcttg tcaaaggcgc    5580
ttatgttgtg tttgaatcaa ctgtttatcc tggtgttaca gaagatgttt gcgtaccaat    5640
acttgaaaaa gagtctggct tgaggtctgg tgaagatttc aaagttggtt actctcctga    5700
gaggataaat cctggtgata aggttcatag gttagaaaca attatcaaag tagtatctgg    5760
tatggatgaa gagtctttag atactatagc aaaagtttat gagctagtag tagacgcagg    5820
agtttataga gctagtagta taaaagtggc tgaagctgct aaggttatag aaaactctca    5880
aagagatgtt aatatagctt ttgttaatga gttatcgata atatttaatc agatgggtat    5940
tgatactcta gaggttttag cagcagctgc aactaaatgg aatttcttaa actttaagcc    6000
tggtcttgtt ggtggacatt gtattggtgt tgacccatat tacctaacgt acaaggcagc    6060
tgagcttgga tatcattctc aggtaatatt atctggtcgt aggataaatg atagtatggg    6120
taaatttgta gttgagaatt tagtcaaaaa actgatatct gcagatatac ctgttaagcg    6180
agctagagta gcaattttcg gctttacttt taaagaagac tgtcctgaca ctaggaatac    6240
tcgagttata gatatggtaa aagagctcaa cgagtatggt atagagccat atattataga    6300
tccggtagct gataaagaag aggctaaaca tgagtatgga cttgagtttg atgatctaag    6360
taaaatggtc aatctagatg cgatcattat tgctgttagt cacgaacagt ttaaagatat    6420
aacaaagcaa cagtttgata ggctatatgc gcataattct agaaagatta tatttgacat    6480
caaaggtagt ttagataaat ctgagtttga aaaagattat atttattgga gattgtagtg    6540
gcttacgata atgttaaatt tcctcatggt tcgttttttt tggtgactgg aggtgcgggt    6600
tttattggct ctaatttatg tgaagtttta cttagtaagg gttatagagt taggtgttta    6660
gatgatctct caaatggtca ctatcacaat gttgagccgt ttttaactaa ttctaattat    6720
gagtttataa aaggtgatat tagagattta gatacttgca tgaaagcttg tgaaggtatt    6780
gattatgttc tacatcaagc tgcttgggga agcgtaccaa gaagtattga gatgccatta    6840
gtgtatgaag atataaatgt taaggtgca ttaaatatgc ttgaagcggc tagacaaaat    6900
aacgttaaaa aatttgtcta tgcttctagt tcatcagtat atggtgatga gccaaattta    6960
cctaaaaaag aaggtagaga aggaaatgtt ttatcaccct atgcatttac aaagaaagct    7020
aatgaagagt gggcgagact atacacaaag ttatatggtc tagatactta tggtctaaga    7080
tattttaatg tttttcggtag aagacaagat cctaatggtg cgtatgcagc agttataccT    7140
aaatttatca aacagttatt aaatgatgaa gcgccaacta taaatggaga tggtaaacag    7200
tcgagagatt ttcatatat agagaatgtt attgaggcaa atcttaaagc atgtttagca    7260
gatagtaagt atgccggaga gtcttttaat atagcttatg gaggtagaga gtatcttata    7320
```

```
gatttgtact ataatctttg tgatgccttg ggtaaaaaaa tagagccaaa ttttggtcca    7380
gatagagcgg gtgatattaa gcatagtaat gctgatattt cgaaggctag gaatatgctc    7440
ggataatatc cggaatatga ttttgaatta ggcataaagc atgctgttga gtggtattta    7500
attaattaaa tggtatttta atcaagtgta cataaaaaaa gtgtctttta aaattttata    7560
tttatattta ctagcttttt gtattatttt tagtttagaa tttaaatttg ctatattgaa    7620
tattatagtt tatcttccgg cttgtatttt gggttttta gctcttaaaa aactatttgt    7680
cggaaatatt gttaagaaac aattagcttt cctttttttc ttttctttt tatcaatgat    7740 ttatttaata atagtccaaa taatcttact tgatgcagca tcattgtttc ctcagttttt    7800
atttaacatt ttgatcgcga taggttttg taactttatt tttgtttcat atgataataa    7860
tgaaaattat ttttttaata tgtctaaaat aatatttttt gttactttct tacaatctat    7920
ttttgtattt ctttcaaggt attatatatt tttaaatgat tggatattct tttttttagt    7980 gaaaaaggg aatattgaga tttcgaatgt tattgaatat aagttaagag tattcggact    8040
tagtaacgct ggaggggatg gtttaggatt ttcaattact ataggattat gttttctat    8100 attttatttt atcaaatata ttaaaggtaa atctatattt accaaactta tgctgtttgt    8160
acctttaatt cttattgtgt tttctaatat tttcatatct agaacatcac tcttaacttc    8220
ttcacttata ttgttaataa caatatttta tatatatatt aaaaagaaa aattactgtt    8280 tattataata ttggcgctat tcttttatc aatatggata ttgttcaaat taaatttgaa    8340
tttgagttgg gcttttgaaa atatttactc gtacattcaa tctggcgatt tttcacatgg    8400
aagtctaagt gttttaatca ataaaatgct ttttgtgcca gataacctt tgacttggat    8460 atttggttgt gaggatgtta gtaatactga tattggttat attaaatatt tatactatta    8520
tgggattata tttagtatgt tttttatat tcttattatt ttcttgtact ttgaaatgag    8580
aaaatgtttt atatttcag agtatcgatc attattcta ttgttgttaa tagtatgttt    8640 agttttcaa gcaaaaataa ttttttgac agtaggatta tttactaaat taaccattat    8700
attatttatt ttttctctta aagaaaacag ctttacaact aggagtgtga tttgaaaagg    8760
tttgtacatt taataataaa ccttaaccaa ggtggtgctg aaacaatgct ttataaactt    8820
tgcaaatcta tggataagtc aatatatcat attacgatta tatcacttat gggtagggga    8880
gtatttgcaa ataagttaga agcttatggt gttaaagttt atacattaaa tttaaataaa    8940
tttaatgtac tatttgtatt gtttaaatat attaagatta tcagaagaat aaagcctgat    9000
gttattcatg cttggatgta tcatgcaaat gtaatttcta tattatgcaa gccttttat    9060 agaaagacta aatatataaa tagtataaga atgggattgg agaattatga tggtcataag    9120
aatcttacaa agtttatgat aaagttgaat gcaaaatttt ctaagttctc agatttaaca    9180
ttaaataatt caaagaaatc attagaagat catcaaaata taggttttaa aaaccaatgc    9240
tttatagcaa atggttttga taagatgtt tttaaaccga gcttttaaa gtatgaaaaa    9300 tttcgtttaa ataatgattt agatgataat gttaaaatta taggtatcat agcaagaaat    9360
catgctgata aaaatatttc tcgtttctta caaatagcta atttattgtt aaaaagtaat    9420
cctagtttac ggtttttaat tgctggaaga gagtgttcga aaatagatat aggtagttat    9480
ctagataaca aaagtaatgt aaataagttt tttgtatttg aatctgtgga ttctagtgaa    9540
tacttaccag tattagattt atatttgtct acatcaaaag ttgaaggttt tccaaatata    9600
cttgcagaag ccatgctatg tgaagttcct attgttgctt ctaatgttgg agattgtaaa    9660
gatatactta atggatacgg tgaagttttt gagcttagtc aaggtaataa agaaataata    9720
```

```
gaaaagatta tgaaagtttt agaaacaacg gtagtcatga aaaagcgcat gagagaatat    9780
ataataaata attttagtat agaagctatt ttggaaaaac acgaaaaact ttatcatgag    9840
ggcagtgtct aatgtgtgga gtagtaggct tttactcatt taataaagaa gaaggttttg    9900
actcaataat taatcaatca ttgctttcta taaagcatag agggtcggat gatagtgggt    9960
attggtgcga caatcaagtt actctggggc atactagatt atcaatacac gatataacta   10020
atgcgggaca tcagccaatg ttatctaata gcggtaatac tgctattgtg tttaatggag   10080
aaatatataa ttacttatcc ataaaaaatc agctattaag tgaatattca aatcttaaat   10140
ttaaaagtaa cagtgatact gaggttttgg tcaatgctat tgaactttgg ggtatagata   10200
aaactttaga aaaatgcata ggaatgtttg cttttggagt ttacagtaga aaaactagtt   10260
gcttaatact agctagagat agatttggcg agaagccatt atattttggt atccaaaatg   10320
gtattttggg ttttgcatca gaattgaagg cacttaagcc attaaaggaa tgtggctgga   10380
ggtttgatat agatagagat gctttagcaa catatatgag gtatgctt at gtaccaacac   10440 catactctat ttataaaaat atatctaaac taaatgtagg tagttacata aaatttgatg   10500
ctaaaggtaa tagtaaagag tataaatatt gggattctaa aaaagtacta gattcagaaa   10560
aatataaaga ttcgtatgat caagcaatcc tagatttaga aattaagctt aaaagtacac   10620
tatcaataca aatgcagtca gatgttcctc taggagcatt tttatccgga ggaattgact   10680
caacaactgt agttgctctt atgcaaagta tgtctaaaga taagataaac acttttagta   10740
taggttttaa tcaaaaagaa tataatgaag ctgagcatgc aagagcagta gcaaaacata   10800
taggtacaaa ccacacagat atgtatgtta cagaaagaga tgctcttgat gtaataccaa   10860
aacttgctgg aatatatgac gagccctttg ctgattcatc acaaatacca acgtatcttg   10920
tgagtaaaat agctaagtcg aaagtaacag ttgcactatc aggtgacgct ggtgatgagc   10980
tctttggcgg ttataataga tactttttag caccaaatat tgctaaaaaa atcaaatttg   11040
ctaagttact aaatatgca ccagatgctt ggataaaaaa agctgagata ttaaattttg   11100
gtaagttcgc tttattagca gataaactac taaaactaaa aagagttctc gaaaaagcaa   11160
aaacaaataa agagctttat gtactacttt gttcacaaat aaatgatact agctttgtgt   11220
taggagcaaa agagtatgat atattaagag ataagaatat ttatgatatt ccacaattat   11280 cttt ccaaga gtggatgatg tttgttgatt ctaatacata tatgatagat gatatattgg   11340
ttaaggttga tagagcagct atggctaact ctctagagac aagagtgcca tttttagatc   11400 ataatatta tgaatttgct tattccttac caattgacta taaaatacaa cgaggtaacg   11460 gaaaagaat tttgaaagat ttgttatata aatatgtgcc agaaagtttg gtcaataggt   11520
ctaagatggg gtttggtatt ccgcttgcta aatggttaag agaagattta cgagagtggg   11580
cagataattt actggattat agtaaaatag acaagcaagg ttacttaagt cctgaggtgg   11640
tgcaaaaata ttggcaagag catttgagtg gtaaaagaaa ttggcaagca atattatgga   11700
atattctaat ttttcaggag tggttagata atgagtaaag taaatgtaac aaaaccatac   11760
ttaccagata taaataaata taaagctat gtaaataaaa tatacaaaaa tggatggctt   11820
actaataatg gtccgttagt gcaagagcta gaaaaaagac ttgcaaagta tctaggtgtt   11880
aaaaatatag ttttagtatc aaatggtaca attgcattag aaatcgcgta tagagcgtta   11940
ggagtcaaag gaagtgcaat tactactcca ttttcatttg ttgctactac atcttcattg   12000
gtttctaaca atgtaaaacc agtgtttgtt gatattgatg agaatactct aagtatagac   12060
gtctctaaaa ttaagtatgc tattgaagag gatacttcag ctattgtgcc agttcatgtg   12120
```

```
tttggaaatg gttgtgaagt tgaaaaaata gacatgctgg ctaaaaaaca taacttaaaa    12180
gttatttatg atgcagcaca tgcttttgat gttaagtata agggtgagag tatattaaac    12240
tatggtgata tttcgacatt aagttttcat gcaacaaaga ttttcattc tattgaagga     12300 ggtgcgctta tcattaatga tgatagtctt gttgaaaaag ttcgttattt cattaatttt    12360
ggtatagaaa gctcagaatc aataccttac ttaggtacta atgctaaaat gaatgaattt    12420
gaggcggcta tgggactttg tgttctagat gatattatag aaattaagag caaaaggaaa    12480
gttattacag agatatatga ggctgggtta gatggattgg taaagtttca agaacagaat    12540
cagcattcta gtaggaatta tagctatttt ccagtaatat ttaggactga ggaggaactt    12600
ctcagagtac agaaagcact aatacaaaat gatataatat cgcgtagata tttttatcca    12660
tcattagata gtcttagtta tatagagcca aagcagtata tgccaatctc aagagatata    12720
tctaaaagaa tattatgttt gccaatttat gcagagttag aagacgataa aattaataaa    12780
ataattaata atatcaaaga ggtttcctca tgaaaaaaat atttgttgtt acagataata    12840
gaactattct aagtgatttt aaaaatatca ttggtagtaa aaatgatgta caggttgatt    12900 attttttgtag tttcaagagt caaacttctt ttgccaaaga aatatataac agtgagatta    12960
agccaataga tatgaaaaaa aatggcaatg atcttattgg taagtatgat ttaggttttt    13020
cttgtcattc gaaacaatta tttccagcaa aattagttaa ttcagtatta tgtataaata    13080
ttcatcctgg acttaatcca tataatagag ggtggtttcc acaggtcttc tctattataa    13140
ataaactacc tataggagca actattcatg tgatggatga agagatagat catggagata    13200
taatcattca ggaagaagtt gaagttaatt cttttcgaaaa ctcttttgat gtttatgcta    13260
aagttcaaaa aaaagaagtt gagttgttca ctaaagtcat agatgatatt ttgaataata    13320
agttcactcg aatcaaacct aactccgaag gcaactaaa ttcaattcat gattataaaa     13380
acatgtgtga aattgattta gataaaatag taacaatgcg ggaagcaatt gactatctaa    13440
gggctatgac acaccctcca tataaaaata gttatttcat tgatgagcat ggaaataaag    13500
tatttgttgc tcttgaactt gaaaagataa gttagaaaaa tgagccttaa aaaaaataca    13560
atatcaaatt atataacaca actatatact agcttaattg gtattgttat acttcctttg    13620
tatttacaac atttaagtca tgatgcattt ggtctgattg gttttttac agttttcaa      13680 acgtggttac ggttgttgga tgttggtata acaccaactt tatcaagaga agtggctcat    13740
gttagaggta gtactgatga ctatcattac ttcgcaagt tggttagatc gttagagcta     13800
tttttcatta ttgttggtgt tctggtattt attgtaatta gtacacattc aaggtatata    13860
tccacctctt ggttacatat aggctcgcta gatgctgata gtgtaagtgt atgtattgca    13920 cttatggggtt taatgtttgc attaagatgg gtgtctgatc tatatggtgg tggtttgcgt    13980
ggctttgaaa gacaggttct ttataataat ttaagtatca tacaaacgac actacagttt    14040
attggtggat tattatttat ctgctatgtg tctactaata ttatgtatta ttttgtatat    14100
cagacaataa ttgcgatact atatctagta tgtattgcaa ttgcatttta taaaatacta    14160
ccatcatcat ttagcgtggg tttaaggttt gattttaaaa taattagaaa agtgcttcca    14220
tttgcactag gcattgcata ttctacaaca gtttggatta ttgtcactca atctgataaa    14280
ttagtgttct cacatgtatt accattatct gagtatggtt attatctttt attgatagtg    14340
atatctagtg ctgttacgat attgtcctct ccgattagca tagctattca gcctagaatg    14400
acaatgctat tagcccaaca aaatgtaaaa ggaatggaaa gcttatattt aaaatcatcc    14460
ttgatctcaa ttacttttttt atctgctgta gtaacatgtg ttttgatgta ttctcatcag    14520
```

```
ctgttgcagt catggacagg aagtatggaa attgctaatt ggggtagtaa tatcttaaat   14580
atatatgttt tatcagcatc tattatttgt ataatatcat ttcaatattt tttacagtat   14640
gcttatggta agttaaagct acataataca tataatacaa ttagtttagt attttttgct   14700
cctatagtta tatatactgc ttataattat ggagtgtata ctacagcact attatggctt   14760
ggatatgcta tagtggggct gataatctgg atgcctattg tacaccatgt atttgctaaa   14820
ggtatcaata ggtattttt tataaattta gcagttatta ctatagtatg ttttttatta   14880
tcgttaatat ttaagggttg gtatatttat ccaagtaaaa ttgggttggt agaattaata   14940
ttgattgggt ttgcattttt atttatacaa atttgtatag agtatgtttt gtttcggtac   15000
aaggttttga ggtgtataga tgattaaagt ttcagtatgt gtgatgacat acaatcaaga   15060
aaagtatatt ggtcaatgtt tagagtcttt ggttactcaa gagactgatt ttgactttga   15120
gataatcgtt ggagatgatt tttctacaga tggtacaaga gatgttattc aagagtatca   15180
aaaaaagtat ccggatatca taaagccagt ttttagagat aagaatgtgg gaattactga   15240
aaatattaaa gaaatctatt ttgttgcaaa tggtgagtat atagctcata tggatggtga   15300
tgattatgca ttgcctggta aacttcaaat tcaggctgat ttttttggata ataatccaag   15360 atgtacggga gttttttcata atataaatat actctatcca aatggtaata tacaacatag   15420 taggttttgct tgttcaaata agagtatatt caatttatca gacactttac gcggagttgc   15480
tgttggtgca aatagttcaa aaatgttcag aacatcggtt ttggatgatt tgattttacc   15540
ggatatagag cttctagatt attatttca tgttataaca gcagaaaaag gttatttaag   15600 tttttttaaat tctaatgaat cctatagtgt gtacagaaaa ggtattggta tcacatctaa   15660
gtctaaggaa aaaatctata atacttatgc tggattattt gaatatttt tggatagata   15720 tcctgaagag aaattaaata tttgtatccc tgttgtgcaa atgataattt cggctattaa   15780
agggagatgt tttattagtg ctattcgtct attcaaaatt ttaattagat caagatgtat   15840
tccattagta agttggttta atatagatt tgaaaaataa atatcattta gaggattatg   15900
tgaaatgaag ggataaattc tagctggtgg cagtggtaca aggctatatc cacttacctt   15960
gggtgttagc aaacagctgc tacctgttta tgacaagcca ttgttatact atccactatc   16020
tgtgcttatg cttgcaggta ttagggagat attaattatc tctacagtgc gtgatatctc   16080
acttatccaa gagcttcttg gtgatggttc acaatttggt atacagttga gttataaaat   16140
ccagccatca ccagatgggc ttgctcaagc atttattctt ggtgaggagt ttttggcggg   16200
tgactcagct tgtttgatat taggagataa tatctactat ggtcaaggta tgactacaat   16260
gctagagtct gcaagagcac agtgtggagg tccagctggt ggcgcttgtg tttttggtta   16320
ttatgttaat gatccgcata gatatggtat agtcgaattt gataagcaaa aaatgtaat   16380 ttcggtagag gaaaagccac agaatcctaa gtcacactat gctatcacag gtttatattt   16440
ttatgataat aatgttgttg agtatgctaa acaagtcaaa ccatctgcac gtggtgagct   16500
agagattact tcacttaatg agttatatct aaaagaaaat aagctaaatg tcgaactctt   16560
agggcgtggc tttgcttggc ttgatgctgg tacgcatgat tcattgctag aggcaggtca   16620
atatgtcgca actattgaga aaagacaagg gcttaaaatt gcatgtttgg aagaaattgc   16680
atggcgtaaa ggctttatct caacacaaca agttctagct caagctgaaa aactttctaa   16740
gacagagtat ggtcagtatc tgaagaattt aattaaggat ggtttataaa ttaatccgtc   16800
atacccatga aggtgggtat ctcataaaag ttggatatgt tttggagatt ccaatctgcg   16860
cagtaatgac aggtttggta atatatagcg atgttttaca atgactaaaa atggttttat   16920
```

```
gtatattctt acaaataagg ataatactgt tctgtacata gttgtaacat ctaatttgat    16980
aaaaagaatg tatgagcata aacatagcct tgcagatggt tttactaaaa atataatgtt    17040
aataagttag tttattttga aatttatgaa gatataaaag cagcaattct gtgagaaaag    17100
cagttgaaaa aatgaaacag atcttggaaa gaacgaatta ttaatgagat gaatccgaat    17160
tggaatgatt tatatgaatt aatatgtgag taaaactttt gtcttactgg tgcagatagg    17220
tatctctaaa tatcagatgt gattgggaga ttaccgccta cgcggtaatg acaagtttat    17280
gcggtaatga tagtttagtg agagaatgac tagtcactat aggaatgatg atgtaatgag    17340
gaatgaaaaa atgaactaca aaccaaaaaa tatcctagta acaggtgcgg cgggatttat    17400
tggtagtaac tatgtgcgta tgatgttatc acgctatagt gatatcaaaa taatctcgta    17460
tgataagctt acttatgcgg gtagtttaga taatctaaaa gacttgaata atgaacataa    17520
ccatactttt ataaaaggtg atatttgtga tgaagtttta gtatatcaaa cactgaaaga    17580
atataaaatt gatacgatag tacattttgc tgcagaatcg catgttgata attcaattgc    17640
taatccaaag gtattttag aaacgaatgt gataggtaca tttacacttt tagattgtgc    17700
taaaaggtat tggttagatg agctaggttt agaagaaact agttgtaggt ttcatcatgt    17760
atctactgat gaggtatatg gtaccttggc aaaagatgaa ccagccttta ctgagattaa    17820
ggcttatgag ccaaattcac cgtattcggc atcaaggcg ggatctgatc atatttctag    17880
agcatatcat catacctata aacttccggt aacaatttca aattgttcaa caactatgg    17940 accataccaa catcgagaga aattaatccc tgtagtgata aatagttgta taaactacaa    18000
gcctattcct gtttacggag atggttcgaa tattcgagat tggctatatg tagaagatca    18060
ctgcgatgct atccagacaa ttgttgagaa aggagtggtt ggagaggttt ataatattgg    18120
tggtattaat gaagttgata atctaaccttt ggtaaaaact atctgtaaac taatggatga    18180
atataaacca gaaaatgctc cacattctaa cttaatcaca tttgtggaag atagaaaagg    18240
acatgattgg cgttatgcta ttgataacag caagattcag aatgagttag gatggaagcc    18300
atcacaagat tttgataaga tgtttagaca aactattgag ttttatctat agcttaaata    18360
tttatcttat gagtatctct aaaaaatcaa tttaatttat ttttgtgtta aaagtagtg    18420 ttcgcaagaa tatagttaat ccgaaagata tttgtagaaa aagatatttg tagaaatgtt    18480
ataatgtcta ataaaaatgc catcatatag ccaagatttt agagacatcg taattaataa    18540
acatgaagaa ggtatgacgg agttcgagct gagtaagttt tttaacatag ataagcgtac    18600
agttgtttca tggatagagt tttataaaag aaccggagat tatagttcaa agcaaggagt    18660
tggttgtggc agagtcgcta gctttaccga taaaacattg attgaacagt atttgataga    18720
tcatccagat gcaagtgcat tagatataaa agaagcatta gcccctgata ttccaagaag    18780
tacattttat gattgtctta atagacttgg ttttagtttt aaaaaaagac tccaaaatat    18840
aagcaaagaa aagaacatga aaggttggag tatatagaaa aactaaaaga aatagccaat    18900
aaatttgatg tacaaatatt atatctacct ccgtactctc cagatttaaa tcctattgaa    18960
aaggtttggg ctaactatta aaaaatatt tagaaaagtg aataatagtt ttgaaaaatt    19020
ttgtgatgct atctcttatg tgtttaacaa atactctcg gattaactat atcatgctgc    19080
taaaatattc ttggtattct ctggtcaaaa ctgacataat gatgctctac tttgtataag    19140
gtttgctaca aatattatct aaacaaacat acaaaggtaa ttttagaga tcctattata    19200 aacctactat ctaaatttag taagttaagt tatgacaata tttaatttgc tgatttattg    19260
ttgaatatat tagctttcta tataattaat caatatcaaa gttatttagg ttttatat   19320
```

```
gattactcct attatcttat ctggaggatt cggctcaagg ctatggccac tatcacgaga   19380
ggcatcgcca aagcagttta tcggcttggt tgatgaacat agtctattag aaaatacaat   19440
taagcgacta gataatgtca aggatataac ttcacctgta gttgtctgta atgaaagtca   19500
tagattccaa gttgctgaag tgttgcggaa aatcaataaa aaaggcgata tactcctaga   19560
gccattagcc agaaatactg ctccagcaat tgcacttgca gcactacatt tagctattaa   19620
tgatccaaat acaattatgc tagttttagc tgctgaccat catattgaaa atctggagat   19680 tttcatcaa gctatcgaaa aagcacagca aaaagttatt aaagatgatt ctttagttac    19740
ctttggcatt acaccaactt gtcctcatga aggctatggt tatattaaac aaggggtaca   19800
gactactgta aatggagttt ataaggtaga taaatttgtt gagaagccta gtgtggtcgt   19860
tgcacaagag tatttagata gtggcaaata ctattggaat agcggtatgt ttatgttcac   19920
agctagagtg tatttagagg ttttagagaa gttacagcca gagatttaca gaggatgtga   19980
aaaaacttat caaagtcac agcaggattt agattttgtg cgttttgata acaaagctt     20040 tgccctagtt caatcacagt caatagacta cgcagttatg gagaaagcaa ctaatgttgc   20100
tatagtgcct atgcaacaaa gtggctggtc tgatgttggc tcttgggact ctttgtatga   20160
tattgctgca aaagatagtt gtggtaatgt ggttattggc gatgtgatta ctagtaatgt   20220
caaaaatagt tatttacgct cgcatgatcg tttattggct gcagtcggag ttaatgattt   20280
aataattgtt gaaacagcag atgctatact tgtcgcggat aagaacaaaa ctcaagatgt   20340
caaaaaaata gtcgaagttt tgaaaattca gcagcgaagt gaattattac agcataagca   20400
aatttataaa ccttggggtt cagcgacaat attagaggat aagtctggtt ataagataca   20460
ggcgattcaa cttgaaccgg gcaagaagtt atcattacag caacattatc accgtagtga   20520
gcattggatt gtgatttctg gaactgctac ggtaactatt ggtactacta agtctattgt   20580
tagaccaaat gagtctgtat atataaaaat aggcgaatct cacagacttg aaaataatgg   20640
caagattcca gttattctta tagaagtaca agttggagaa tatataagtg aagacgatat   20700
tgttagacta gatacaagta gttaatataa aaacaattag atagaaaaaa atataatgag   20760
acaaactata ataaaagaaa taatcaaatc tagcggcgta aagtttggta ctagtggagt   20820
tagaggtctt gtttcagcta tgacagataa gatctgttgg ctttatacaa agcttttat    20880 tcaattccta gagcaaaaat actctattgc taagggtact aaaattgcta tagctcatga   20940
tctacgtgag agtagcccta gaataacaac agttgttatt aaagctatca tagatagtgg   21000
tcatgagcca atatactgtg gtgagatacc atcaccagct gtaatgctat atggtatatc   21060
taatcagata ccgtcagtta tggttactgg tagtcatatt ccagaggata gaaatggtat   21120
taagtttaat actccatatg gtgaagttct caaagaagat gaagaaatga ttgttagcca   21180
aactatcagc attgatgaaa gtattttga taaaaatggc atgtttttac aaaaactaga    21240
attaccagag cctagtaagc aagcatatac acagtatatt gacaggtatg tagatttttt   21300
ccctaacaac tgtctagcag gtaagactat agggctttat cagcactcat ctgtaggacg   21360
agagatagtc aaagagattc tagagaaact aggtgctaag gttatcttgc tagaattttc   21420
cgaaaaattt gtatctgtag ataccgaggc aattcgccag gaagatgtaa agcttgctaa   21480
gcagtgggca agcaagtata aagttgatag tatagtttca actgatggcg atgctgatag   21540
gccactagtt agtgatgagt atggcaattg gctaaaaggt gatattttag gtgtactgac   21600
agctaaatat ctccaagcca atgttatcgt gacaccagta agtagcaata ctgtggcaga   21660
aaagataggt tattttagta acgtgattag aactaaaata ggctcgccgt atgtaattgc   21720
```

```
tgcaatgaat gaattactct caaataatca aaatgctgtg gttggatatg aggcaaatgg    21780
aggatttcta ttggctagtg atatttgtaa agatgataaa actctaaaag cgctgcctac    21840
aagagatgct gttataccaa tgttggctgt aatgatgcta tctatcaact ctaataaaac    21900
cgtgtcagag cttttatttg atttgccatc tcgatataca gcaagtagta aaattgatga    21960
ttttgcttcc gagaaaagcc aagaaatctt gaagtcaata ttagcaggtg aatcagatct    22020
tttagataaa attatatcgg agcattttga tggtaaaaat agcattgaaa atatcgatac    22080
tacagatggt gttagagtaa cttgacaaa tcaagatatt atccatctta gaccatctgg     22140
taatgctcca gagcttaggt gctatacaga ggcagctagt gatgagcagg caaaagttt     22200 aaatcaatat tgtgtggatt tgattaacaa aaacatttga agatcagtca aaaatattcc    22260
ctaacttttc tcttcaccat tgaaccatta ctaaccttat ctatagctag ccacagataa    22320
aaatgtcatg ctggatttat ttcagcgttt cattataaat atcaatttta ttgagatcct    22380
gaaactagtt caggatgaca g                                              22401
```

IMMUNOGENIC SEQUENCES

CROSS REFERENCE TO RELATED APPLICATIONS

This application is a continuation of U.S. patent application Ser. No. 10/516,215, filed Sep. 1, 2005, which is the U.S. national phase of International Application No. PCT/GB2003/02338, filed May 30, 2003, and published in English as International Publication No. WO 03/102191 A1 Dec. 11, 2003, which application claims priority to Great Britain Application No. 0212666.2, filed May 31, 2002, the contents of each of the foregoing are incorporated by reference herein.

The present invention relates to nucleic acid sequences, in particular genes that encode the enzymes which produce the O-antigen of *Francisella tularensis*, and their use as or in the production of vaccines and in diagnosis.

*Francisella tularensis* is a small Gram-negative coccobacillus, which causes the zoonotic disease Tularemia. According to Bergey's manual of systematic bacteriology the genus *Francisella* contains two species: *F. tularensis* and *Francisella novicida*. However, recently several workers have suggested that *F. novicida* be considered a subspecies of *F. tularensis* (Hollis D G, et al., *J. Clin. Micro.* 27: 1601-1608). The closely related bacterium *Yersinia philomiragia* is now also considered a member of the genus *Francisella*, due to its high degree of relatedness at the DNA level. There are several proposed subspecies of *F. tularensis* other than novicida; these are: subspecies *tularensis*, subspecies *holarctica* and subspecies *mediaasiatica*. The subspecies *tularensis* and holarctica can be identified on the basis of virulence, citrulline ureidase activity and acid production from glycerol (Olsufjev N G, et al. (1959) *J. Hyg. Epidemiol. Xicrobiol. Immunol.* 3: 138-149. *Francisella tularensis* subspecies *mediaasiatica* is predominantly found in central asian republics of the former USSR. Strains of this subspecies possess citrulline ureidase activity, and are able to ferment glycerol, but are less virulent than strains of *F. tularensis* subspecies *tularensis* in rabbit.

Tularemia is a disease occurring in the northern hemisphere; with cases frequently found in Europe, N. America, Asia, N. Russia and Japan. Rodents are thought to be the main reservoir of the bacteria, with ticks as one of the main vectors.

The lipopolysaccharide (LPS) of Gram-negative bacteria is the major component of the outer membrane. The molecule is composed of 3 regions, lipid-A, which is embedded in the outer membrane and has a conserved structure between species, and two polysaccharides, the core oligosaccharide which can vary in complexity between species, and the O-antigen which is a very polymorphic structure (Kenne L, et al. (1983) Bacterial Polysaccharides *The polysaccharides*. Academic Press, pp. 287-362). The LPS molecule is thought to be required by the bacteria for protection against serum killing (Whitfield C, et al, (1997) *Mol. Micro.* 23: 629-638) and cationic antimicrobial peptides (Groisman E A. (1994). *Trends. Microbiol.* 2: 444-449).

The structure and immunogenicity of LPS isolated from the less virulent *F. tularensis* subspecies *holarctica* strains has been studied to some degree (Dreisbach V C, et al. (2000) *Infect. Immun* 68: 1988-1996). Animals immunised with this LPS are protected against a subspecies *holarctica* strain challenge (Fulop M J, et al. (1995). *Vaccine* 13: 1220-1225), but not a subspecies *tularensis* strain challenge (Fulop M J, et al. (2001). *Vaccine* 19: 4465-4472). However, the LPS from a subspecies *holarctica* strain appears to be less toxic than other Gram-negative LPS and its O-antigen contains rare sugars which are related in structure to those found in *Pseudomonas aeruginosa* 06 and *Shigella dysenteriae* type 7.

There are no reports of LPS isolation from the more virulent subspecies *tularensis* strains.

When LPS structure is studied in other species, it is frequently observed that the only difference in structure between strains is the composition of the O-antigen. Therefore, it would be useful to elucidate the structure of the O-antigen part of the LPS molecule in virulent subspecies in order to provide the basis for diagnostic tests and also to allow it to be produced recombinantly, to avoid handling a pathogenic organism.

However, the genetic basis of O-antigen expression is complex; in most bacteria the genes required for production of a complete O-antigen are located in a cluster on the bacterial chromosome. Therefore identification and isolation of genes responsible for the O-antigen is not straightforward. Furthermore, the identification and isolation of LPS from virulent strains is further complicated because it is difficult to stain using conventional methods.

The applicants have now determined the genetic basis of O-antigen production in *F. tularensis* subspecies *tularensis*. Furthermore, they have established the efficacy of LPS from various *F. tularensis* strains as a vaccine.

According to the present invention there is provided a nucleic acid which encodes a series of enzymes or enzyme fragments which, when expressed together in a cell, are able to produce an immunogenic moiety able to produce an immune response in an animal to which it is administered, which response is protective against *Francisella tularensis* infection, said nucleic acid encoding at least some of the enzymes of SEQ ID NOS 3-17, or modifications thereof.

The expression "modification" refers to sequences of amino acids, which differ from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably modifications will be at least 60% identical, preferably at least 75% identical, and more preferably at least 90% identical to the base sequence.

Identity in this instance can be judged for example using the algorithm of Lipman-Pearson, with Ktuple:2, gap penalty:4, Gap Length Penalty:12, standard PAM scoring matrix (Lipman, D. J. and Pearson, W. R., Rapid and Sensitive Protein Similarity Searches, *Science,* 1985, vol. 227, 1435-1441).

In particular, the invention comprises a nucleic acid which encodes enzymes of SEQ ID NOS 3-17.

A preferred example of such a nucleic acid comprises SEQ ID NO 1 or a variant thereof. In particular the nucleic acid is of SEQ ID NO 1.

The term "variant thereof" in relation to a nucleic acid sequences means any substitution of, variation of, modification of, replacement of, deletion of, or the addition of one or more nucleic acid(s) from or to a polynucleotide sequence providing the resultant protein sequence encoded by the polynucleotide exhibits the similar properties as the protein encoded by the basic sequence. The term therefore includes alleleic variants, degenerate variants which encode similar proteins but vary only as a result of the degeneracy of the genetic code. It also includes a polynucleotide which substantially hybridises to the polynucleotide sequence of the present invention. Preferably, such hybridisation occurs at, or between low and high stringency conditions. In general terms, low stringency conditions can be defined as 3×SSC at about ambient temperature to about 55° C. and high stringency condition as 0.1×SSC at about 65° C. SSC is the name of the buffer of 0.15M NaCl, 0.015M tri-sodium citrate. 3×SSC is three times as strong as SSC and so on.

Typically, variants have 65% or more of the nucleotides in common with the polynucleotide sequence of the present invention, more typically 70%, preferably 75%, even more preferably 80% or 85% and, especially preferred are 90%, 95%, 98% or 99% or more identity.

Variants may comprise the basic sequence which has been modified to ensure that the codon usage is enhanced or optimised, as would be understood in the art, for a particular organism in which it is required that the sequence is expressed in a desired organism, for example a prokaryotic cell such as E. coli. This may involve modifying the content of particular nucleotides, for instance changing the percentage of G and C present in the sequence, to suit that usually found in genes which are highly expressed in the target organism. In addition, particular variants of SEQ ID NO 1 are synthetic variants, engineered to remove codons rarely found in highly expressed genes from common expression hosts such as E. coli and, at the same time, avoid the introduction of codons rarely found in genes coding for O-antigens. For example, wherever possible the codons for the amino acids arg, leu, ile, gly and pro are changed to CGT or CGC (arg), CTG, CTT or CTC (leu), ATC or ATT (ile), GGT or GGC (gly), and CCG CCA or CCT (pro), thus eliminating rare codons.

When comparing nucleic acid sequences for the purposes of determining the degree of identity, programs such as BESTFIT and GAP (both from Wisconsin Genetics Computer Group (GCG) software package). BESTFIT, for example, compares two sequences and produces an optimal alignment of the most similar segments. GAP enables sequences to be aligned along their whole length and fins the optimal alignment by inserting spaces in either sequence as appropriate. Suitably, in the context of the present invention when discussing identity of nucleic acid sequences, the comparison is made by alignment of the sequences along their whole length.

SEQ ID NO 1 comprises a series of genes which encode a number of enzymes which are shown hereinafter in FIG. 5 and SEQ ID NOs 3-17. Preferably any variants of SEQ ID NO 1 encode enzymes of SEQ ID NOS 3-17 or modifications of these.

The expression "fragment" used in relation to amino acid sequences refers to any portion of the given amino acid sequence which has the same activity as the complete amino acid sequence. Fragments will suitably comprise at least 20 and preferably at least 50 consecutive amino acids from the basic sequence.

The term "fragments" is also used in relation to nucleic acid sequences. Fragments of SEQ ID NO 1 may have applications in diagnostics, and these form a further aspect of the invention. For diagnostic purposes, fragments may be quite short, for example from 5-30 bases, which may be used as primers or probes. Particular characteristic regions of SEQ ID NO 1 from which suitable fragments for diagnostic purposes may be identified are elucidated hereinafter. Fragments which are useful in therapy would generally be expected to be longer, for example from 600-17,000 bases long.

A region of genome of the F. tularensis strain Schu 24 (subspecies tularensis) which includes SEQ ID NO 1, and which is responsible for expression of the set of enzymes necessary for constructing the polysaccharide, has been identified. It is shown hereinafter in FIG. 4 as SEQ ID NO 41. This sequence includes a number of genes including a series of genes that encode the enzymes illustrated in FIG. 5 hereinafter as SEQ ID NOS 3-20. Putative functions were applied to these genes by comparison with known sequences as illustrated in Table 1.

TABLE 1

| SEQ ID NO | F. tularensis protein | Gene product size (aa) | Putative function |
|---|---|---|---|
| 2 | Transposase | 247 | Hypothetical protein Transposase |
| 3 | WbtA | 578 | Sugar epimerase |
| 4 | WbtB | 205 | Galactosyl transferase Glycosyl transferase |
| 5 | WbtC | 263 | UDP-glucose 4-epimerase |
| 6 | WbtD | 363 | Sugar transferase |
| 7 | WbtE | 436 | LPS biosynthesis Dehydrogenase |
| 8 | WbtF | 323 | C 4-epimerase |
| 9 | Wzy | 409 | Membrane protein/O-antigen polymerase |
| 10 | WbtG | 366 | Transferase |
| 11 | WbtH | 628 | Asparagine synthetase |
| 12 | WbtI | 360 | Sugar transaminase/perosamine synthetase |
| 13 | WbtJ | 241 | Formyl transferase |
| 14 | Wzx | 495 | o-antigen flippase |
| 15 | WbtK | 286 | Glycosyl transferase |
| 16 | WbtL | 294 | Glucose-1-phosphate thymidylyltransferase |
| 17 | WbtM | 348 | dTDP-D-glucose 4,6-dehydratase dTDP-D-glucose 4,6-dehydratase |
| 18 | Transposase | 126 | Transposase |
| 19 | ManC | 468 | Mannose-1-phosphate guanylyltransferase |
| 20 | ManB | 494 | phosphomannomutase |

In particular the proteins illustrated as SEQ ID NOS 3-17 are believed to be involved in O-antigen biosynthesis. The O-antigen itself has applications both in diagnostics and as a prophylactic or therapeutic vaccine.

When the nucleic acids of the invention are expressed together in a host cell, they will result in the construction of an antigen that produces an immune response in an animal including a human, which is protective against infection by F. tularensis. Thus they may be used in the production of prophylactic or therapeutic vaccines.

The nucleic acid may be included in a vector such as a live viral vaccine, for instance, adenovirus vector or vaccinia, or in a plasmid to form so-called "naked DNA" vaccines, or preferably in a bacterial vector such as attenuated Salmonella species. In this case, the nucleic acid will be under the control of suitable control elements such as promoters, signal sequences, enhancers and the like, as would be understood in the art. In this case, the nucleic acid is expressed either within the cells of the patient to whom the vaccine is administered, or in the case of bacterial vectors, within the host cell itself. As a result a series of enzymes are produced which are able to construct the protective O-antigen in situ.

The vector is suitably combined with a pharmaceutically acceptable carrier in a vaccine formulation. The nature of the carrier depends upon the type of vector being used, as would be understood in the art. In particular, when the vaccine comprises a recombinant Salmonella, it is suitably in the form of a composition which is suitable for oral administration.

Alternatively, the nucleic acid may be included in an expression vector which is used to transform a host cell. Suitable host cells are prokaryotic or eukaryotic cells, but are preferably prokaryotic cells such as E. coli. In particular, the nucleic acid used is a synthetic variant of SEQ ID NO 1, optimised for expression in the particular host cells. The protective O-antigen can then be recovered from these cells after culture thereof.

Thus in a further aspect there is provided a method of preparing a prophylactic or therapeutic vaccine, which method comprises transforming a host cell with a nucleic acid of the invention, culturing said host cell, and recovering a moiety which produces a protective immune response against *F. tularensis* therefrom.

Expression vectors and host cells for use in this method, together with the product thereof form further aspects of the invention.

Vaccines of this type will suitably be in the form of a pharmaceutical composition, in which the antigen is combined with a pharmaceutically acceptable carrier, as would be understood in the art.

The compositions of the invention may be in a form suitable for oral use, for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosin.

The compositions of the invention may be obtained by conventional procedures using conventional pharmaceutical excipients, well known in the art.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of moiety of the invention will naturally vary according to the age and sex of the animal or patient and the route of administration, according to well known principles of medicine.

Thus in a further aspect the invention provides recombinant O-antigen of *F. tularensis* which is obtainable from a host cell which expresses proteins of SEQ ID NO 3-17, or modifications thereof.

Furthermore, the applicants' realisation of the sequence of the O-antigen sequence provides the possibility that this sequence can form the basis of diagnostic tests, to determine whether a patient has an *F. tularensis* infection. In such case, samples such as blood or saliva samples may be taken from the patient and the presence of SEQ ID NO 1 or variants thereof detected.

Specific detection methods are well known in the art, and may include amplification procedures such as the polymerase chain reaction (PCR) and/or other detection methods using for example labelled probes that hybridise to the target sequence and particularly SEQ ID NO 1. Primers and probes of this kind form a further aspect of the invention.

By selection of particular primers and probes, it may also be possible to allow differentiation between strains of *F. tularensis* infection. For instance, the applicants have found that primers comprising SEQ ID NOS 21 and 22 and 35 and 36 set out hereinafter will allow distinction between strains of *F. tularensis* subspecies *tularensis*, and *F. tularensis* subspecies *holarctica* as described below. In the former case, this possibility arises because of differences in the downstream sequence, and in the latter, because of differences in deletions in the flanking transposase sequence. Consequently, analysis using primers or probes based upon these regions may be used to determine whether any particular strain is *F. tularensis* subspecies *tularensis* or otherwise.

In order to discover whether the LPS from a subspecies *tularensis* strain has similar structure (and properties) to that from a subspecies *holarctica* strain, LPS from *F. tularensis* strain Schu S4 (subspecies *tularensis*) was extracted.

LPS extracted from *F. tularensis* strain Schu S4 was shown to have a characteristic ladder pattern after gel electrophoresis. However, the LPS was difficult to stain and required additional oxidation in order to visualise the O-antigen bands. This may suggest that the sugars in the O-antigen of *F. tularensis* strain Schu S4 are not oxidised in the same way as the O-antigen sugars found in most other bacteria.

The *F. tularensis* strain Schu S4 O-antigen gene cluster contained 15 genes, the putative functions of which was assigned (see Table 1 above) based on the BLAST results and structural information about the sugars contained in the O-antigen. Genes within the cluster are likely to be responsible for the production of the O-antigen molecule as well as the transportation of the molecule out of the bacterial cell.

There are two main O-antigen synthesis modes, O-antigen polymerase (wzy)-dependent and wzy-independent. In the wzy-dependent system it is thought that the polymerase (wzy), flippase (wzx) and chain length determinant (wzz) are part of a complex in the cell wall which facilitates polymerisation and export of the LPS molecule. In the wzy-independent system a different set of proteins are involved in the transportation and polymerisation of the LPS molecule. The transporter is ATP driven and composed of two proteins wzt and wzm that belong to the ABC-transporter family.

In the *F. tularensis* O-antigen gene cluster, proteins with high identity to wzy and wzx are present, suggesting that transportation and polymerisation of the O-antigen is via a wzy-dependent pathway.

The TMHMM analyses of the putative O-antigen flippase (Wzx) and polymerase (Wzy) proteins supported their assigned functions based on sequence similarity. The predicted numbers of trans-membrane helices for the *F. tularensis* proteins of 14 and 11 for Wzx and Wzy respectively are similar to those predicted for other bacteria, in which these cytoplasmic membrane proteins have been predicted to have around 10-12 trans-membrane helices. The prediction of 2 large periplasmic domains for the *F. tularensis* Wzy protein is consistent with the two large periplasmic domains of the *Shigella flexneri* Wzy protein.

No gene that could encode a Wzz homologue was identified, which may indicate that one is not present in the *F. tularensis* genome.

The close proximity or overlapping of the genes wbtA to wbtL suggests these are transcribed as one operon.

Approximately 0.5 Kb downstream is wbtM, which has a putative promoter of its own. Downstream of the second transposase are manC and manB, which also have their own putative promoter and are probably not involved in biosynthesis of the O-antigen as mannose was not found to be part of the structure of the *F. tularensis* O-antigen, nor is it one of the intermediate products required for its synthesis.

The two genes manC and manB may once have been involved in biosynthesis of the O-antigen in an ancestor of *F. tularensis*. The presence of transposases flanking the O-antigen biosynthetic gene cluster wbtA to wbtM suggests this cluster may have been horizontally acquired, perhaps replacing an ancestral polysaccharide gene cluster.

The O-antigen gene cluster appears to be present in all subspecies *tularensis* and B strains screened. However, there is at least one difference between the clusters in subspecies *tularensis* and B strains within a region containing a transposase. BLAST analysis using the partially deleted transposase has revealed possibly over 50 copies of it in the *F. tularensis* Schu S4 genome. It is possible that the insertion sequence originated in the *F. tularensis* genome from *S. pneumonia* and was copied randomly within the genome. The open reading frames flanking the insertion sequence have no significant homology within the *F. tularensis* genome, suggesting that these genes were not imported to this locus with the insertion.

In subspecies *tularensis* strains, this insertion has become deleted to leave only fragments of the transposase and downstream sequence. The overall similarity between the subspecies *tularensis* and subspecies *holarctica* clusters seems to indicate that the insertions took place in *F. tularensis* before division of the subspecies. Partial deletion of the subspecies *tularensis* transposase would have the effect of stabilising this region of DNA, as this enzyme has been found to be necessary for insertion events to take place.

It seems unlikely that this will affect expression of the cluster in either subspecies *tularensis* or B strains. It could be that in subspecies *tularensis* strains part of the transposase has been lost due to genome down sizing. However, the gross difference in size of PCR products generated across this region when amplifying DNA from different subspecies may be utilised in diagnostic procedures.

The applicants have found that a similar O-antigen gene cluster to that found in *F. tularensis* strain Schu S4 is present in other strains of *F. tularensis*. This includes subspecies *holarctica* strains. Consequently, a vaccine which utilises the O-antigen to produce a protective immune response is likely to provide protection against infection by several virulent strains of *F. tularensis*.

The applicants have demonstrated that LPS from *F. tularensis* subspecies *tularensis* strains is protective. In particular, it appears to be protective against challenge from strains other than *F. tularensis* subspecies *tularensis*, and in particular against challenge with *F. tularensis* subspecies *holartica*. This finding is unexpected in view of the results reported above which suggest that LPS from *F. tularensis* subspecies *holartica* is not protective against infection by other *F. tularensis* species. Thus recombinant vaccines as described above will be particularly useful.

Thus in a further aspect, the invention provides LPS obtainable from *F. tularensis* subspecies *tularensis* for use as a vaccine against infection by *F. tularensis*. Vaccine compositions containing LPS from *F. tularensis* subspecies *tularensis* are also novel and form a further aspect of the invention. These will comprise pharmaceutically acceptable carriers as described above.

The invention will now be particularly described by way of example with reference to the accompanying diagrammatic drawings in which:

FIG. 1. SDS-PAGE analysis of LPS isolated from *E. coli* strain K325, 1.25 µg (track 1) and *F. tularensis* strain Schu S4, 50 µg (track 2).

Figure 2:
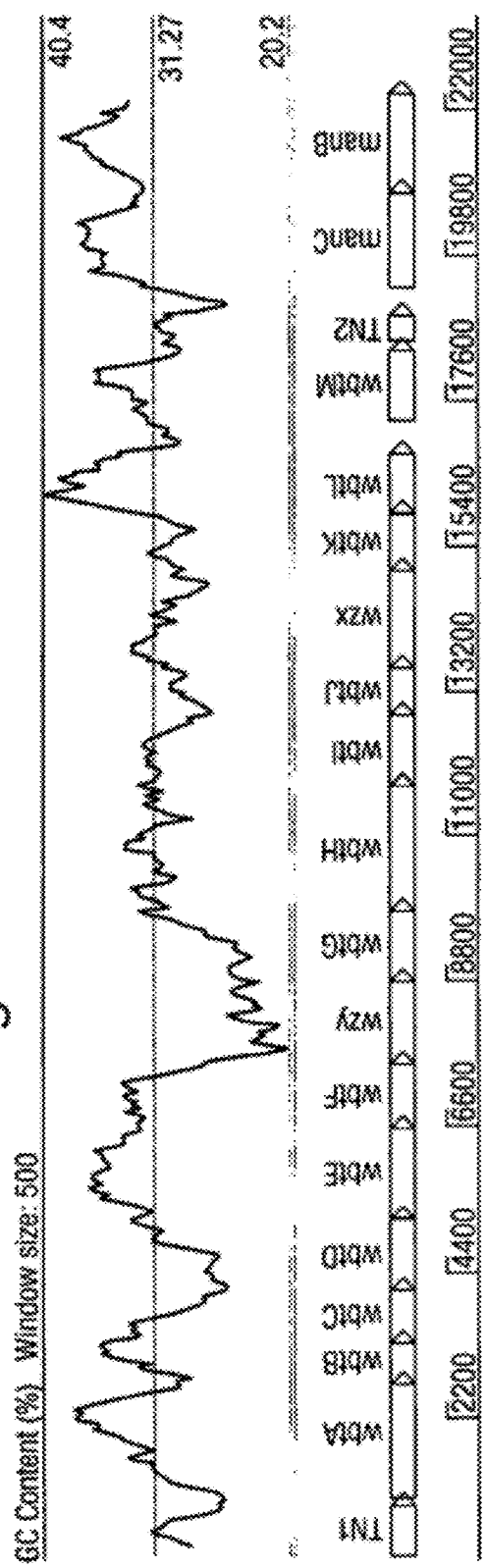

FIG. 2. The genetic organisation of the O-antigen gene cluster in *F. tularensis* strain Schu S4. The G+C content of the O-antigen cluster is shown in the upper panel.

Figure 3:
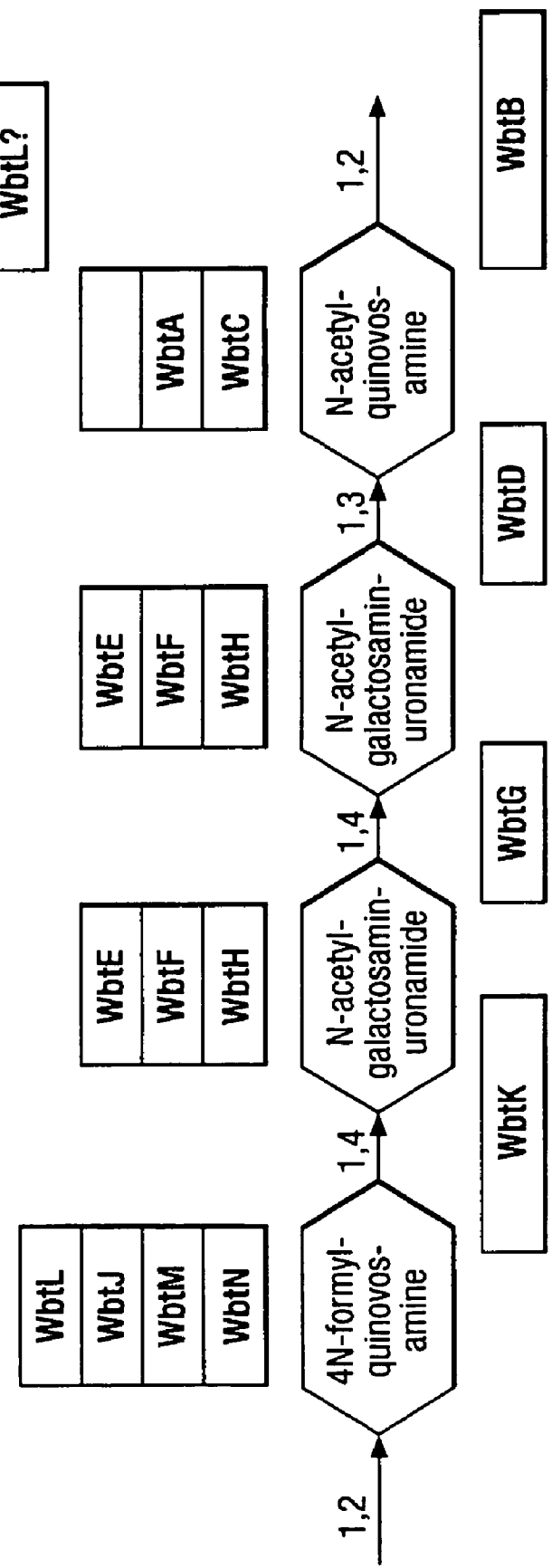

FIG. 3. Schematic structure of an O-antigen subunit of *F. tularensis* strain Schu S4 and the assignment of putative functions to the O-antigen gene cluster genes. A single O-unit is shown with sugar residues and glycosidic linkages indicated.

FIG. 4. Shows the region of the genome the nucleic acid sequence of the *F. tularensis* genome which encodes all the proteins shown in FIG. 5.

FIG. 5. Shows the amino acid sequences of proteins encoded by SEQ ID NO 1, as well as a number of flanking gene sequences, FIG. 6. Shows the nucleic acid sequence (SEQ ID NO 1) which encodes the enzymes necessary for O-antigen production.

EXAMPLE 1

Methods
Bacterial Strains and Growth Conditions
Bacterial strains used in this study are shown in Table 2 and were cultured at 37° C. on BCGA agar for 48 hrs.

TABLE 2

| Species and Strain | Subspecies |
| --- | --- |
| *F. tularensis* Schu4 | *tularensis* |
| *F. tularensis* 199 | *tularensis* |
| *F. tularensis* 230 | *tularensis* |
| *F. tularensis* 041 | *tularensis* |
| *F. tularensis* LVS | *holarctica* |
| *F. tularensis* 200 | *holarctica* |
| *F. tularensis* 025 | *holarctica* |
| *F. tularensis* 075 | *holarctica* |
| *F. tularensis* HN63 | *holarctica* |
| *F. tularensis* 147 | *mediaasiatica* |

LPS Purification
LPS was purified from *F. tularensis* strain Schu S4 using a hot-phenol and water extraction method (Westphal O, et al. (1965). *Methods in Carbohydrate Chemistry* 5: 83-91).

Gel Electrophoresis and Silver Staining
Glycine gel electrophoresis was performed according to the method of Laemmli (Laemmli U K. (1970). *Nature* 227: 680-685.) using a 12.5% separating gel with a 4.5% stacking gel. Ten µl of each sample were electrophoresed for approx 2 h at 100 my in the Mini-protean II slab system (Biorad).
Gels were silver stained according to the method of Chart (Chart H. (1994) LPS: Isolation and Characterisation. In: Raton B, Arbor A (eds.) *Methods in Practical Laboratory Bacteriology*. CRC Press, London, Tokyo, pp. 11-20). However, the oxidation step was increased to 10 min.

Nucleotide Sequence Analysis
The sequence encoding the O-antigen biosynthetic cluster was identified and extracted from the Known protein sequences (obtained from GenBank) involved in the biosynthesis of the 0-antigen of other bacteria were used to probe the *F. tularensis* Schu S4 partial genome sequence (Prior RG, et al. (2001) *Journal of applied microbiology* 91: 614-620), using TBLASTN (Altschul SF. et al. (1997) Nucleic acids research 25: 3389-3402). The contig containing the putative O-antigen gene cluster was extracted and subsequently analysed using the annotation tool Artemis (Wellcome Trust Sanger Institute, UK). This allowed visualization of BLASTN, BLASTX and BLASTP searches, GC content and other analyses performed on the sequence and the predicted proteins.

The protein sequences encoded by the putative O-antigen flippase gene (wzx) and O-antigen polymerase gene (wzy) were analysed for trans-membrane helices using TMHMM (Sonnhammer E L L, et al. (1998) In: Glasgow J, Littlejohn T, et al. (eds.) *The sixth international conference on intelligent systems for molecular biology*. AAAI Press, Menlo Park, Calif., pp. 175-182).

PCR Analysis of the Putative O-Antigen Gene Cluster

DNA was prepared from the *F. tularensis* strains shown in table 1, by phenol extraction, as described by Karlsson et al 2000 (*Microb. Comp. Genom.* 5: 25-39). Ten pairs of overlapping PCR primers were designed to amplify the whole of the putative O-antigen gene cluster in approximate 2 kilobase segments using the DNAstar program PrimerSelect. The primers were designed with annealing temperatures ranging from 42 to 59° C., although all were used successfully at 49° C.

The structures of these primer pairs is summarised in Table 3.

TABLE 3

| Primer set | Forward/reverse | Structure | SEQ ID NO |
|---|---|---|---|
| 1 | Forward | ATAATGAAATCAATCCACGAG | 21 |
|   | Reverse | CCAGCCAGTCAGTCCCACAG | 22 |
| 2 | Forward | TGTCTTAGATATGGGGCAACC | 23 |
|   | Reverse | ACAAATATCAAATCCTAACACATC | 24 |
| 3 | Forward | TAGAAGCAGCTGCGATAGGTAGAC | 25 |
|   | Reverse | TTAAATAAAAACTGAGGAAACA | 26 |
| 4 | Forward | ATGGTATTTTAATCAAGTGT | 27 |
|   | Reverse | CTAGTATGCCCCAGAGT | 28 |
| 5 | Forward | TGGTGCGACAATCAAGTTA | 29 |
|   | Reverse | AGAAGTTCCTCCTCAGTC | 30 |
| 6 | Forward | AGAAATTAAGAGCAAAAGGAAAGT | 31 |
|   | Reverse | ATCTCAAAGTCAAAATCAGTCTCT | 32 |
| 7 | Forward | TACGATATTGTCCTCTCCGATTAG | 33 |
|   | Reverse | TAGTTGCGACATATTGACCTG | 34 |
| 8 | Forward | AGGCAGGTCAATATGTCGCAACT | 35 |
|   | Reverse | TTTCCGCAACACTTCAGCAACTT | 36 |
| 9 | Forward | GCTATGGCCACTATCACGAGAGG | 37 |
|   | Reverse | TATACTTGCTTGCCCACTGCTTAG | 38 |
| 10 | Forward | ACCGTAGTGAGCATTGGATTGT | 39 |
|   | Reverse | ACTAGGGCCTCTGACCGTTCTC | 40 |

PCR amplification using each pair of primers with each template DNA was carried out in the following mixture: 1×PCR buffer (including 1.5 mM $MgCl_2$), 0.2 mM deoxynucleoside triphosphates (dNTPs), 2.5 mM forward primer, 2.5 mM reverse primer, 2.0 µl template DNA, 0.5U Taq polymerase and filtered sterile water to a final volume of 20 µl. The reaction mixtures were incubated at 90° C. for 1 min and then cycled at 90° C. for 1 min, 49° C. for 1 min and 72° C. for 2 min 25 s for 30 cycles, with a final incubation at 72° C. for 10 min. PCR products were visualised on 0.5% agarose gels, with ethidium bromide staining. PCR buffer, dNTPs, and polymerase were from Roche. PCR primers were synthesised by MWG-Biotech.

Cloning of PCR Products

PCR products amplified from Schu S4, HN63 and LVS DNA using primer pair 8 were cloned into pGEM-T easy (Promega) for sequence analysis. Ligated DNA was transformed in *E. coli* JM109 chemically competent cells (Promega) and putative clones were screened using both colony PCR and digestion with restriction endonucleases. All DNA manipulations, including ligations, transformations, colony PCR, restriction endonuclease digestions and agarose gel electrophoresis were carried out according to methods described by Sambrook et al (1987) Molecular cloning: A laboratory manual. Cold Spring Harbor, N.Y.).

Purification of PCR products from agarose gel was achieved using the QIAquick Gel Extraction Kit (Qiagen) according to the manufacturer's instructions.

The three constructs were sequenced at Oswel by the dideoxynucleotide chain-termination method (Sanger F, et al. *Proc. Natl. Acad. Sci. U.S.A.* 74: 5463-5467) using universal primers. Each sequence was compared and the BLAST (Altschul S F, et al. (1990) Basic local alignment search tool. *J. Mol. Biol.* 215: 403-410) function of the ARTEMIS software package was used for homology searches in the locally held GenBank databases to identify the functions of the differential regions of DNA.

Mass Spectrometry Analysis of the O-Antigen Molecule
Results
LPS Purification

The hot phenol-water extraction method was used to purify LPS from 2.2 g of freeze dried *F. tularensis* strain Schu S4. This resulted in 7 mg of LPS, which is a yield of 0.3%. The LPS was difficult to visualise after SDS-PAGE and silver staining. The oxidation step was increased from 5 min to 10 min to visualise a ladder pattern (FIG. 1).

*F. tularensis* O-Antigen Biosynthetic Gene Cluster

The *F. tularensis* O-antigen biosynthetic gene cluster was found to be 17 Kb in length and contain 15 genes putatively identified as being involved in O-antigen biosynthesis, flanked by two transposases (FIG. 2). Possible promoter sites were identified just upstream of the genes wbtA and wbtM. Downstream of the second transposase are located the genes manC and manB, with a possible promoter just upstream of manC.

FIG. 2 also shows the G+C content plot of the cluster using a window size of 500 bases. The overall G+C content of this region of the genome at 31.27% is slightly lower than the genome average of approximately 33%. The plot shows that the central section of the cluster, from wzy to wbtK, generally has an even lower G+C content.

Downstream from manC, on the opposite strand, are located the genes for the transcription termination factor rho and thioredoxin. In *E. coli* both of these genes are also found flanking one end of a polysaccharide biosynthetic gene cluster—that of the enterobacterial common antigen.

The O-antigen repeat unit of *F. tularensis* is shown in FIG. 3, together with the putative role of the genes involved in O-antigen biosynthesis. Based on their homology to other LPS and sugar biosynthetic genes, in particular *P. aeruginosa* serotype O6 which expresses a similar O-antigen repeat structure (Knirel Y A, et al. (1985) *Eur. J. Biochem.* 150: 541-550), the putative role of the gene products have been assigned.

It is proposed that the biosynthesis of 2-acetamido-2,6-dideoxy-D-glucose (QuiNAc) involves WbtA, a dehydratase and WbtC, which shows homology to UDP-Glc 4-epimerases. WbtA and WbtC share homology to WbpM and WbpV of *P. aeruginosa* strain O6, both thought to be involved in QuiNAc biosynthesis and shown to be essential for O6 O-antigen synthesis. WbtE, WbtF and WbtH are proposed to be involved in 2-acetamido-2-deoxy-D-galactouronamide (Gal-NAcAN) biosynthesis. WbtF shows homology to UDP-glucose 4-epimerases, including WbpP and VipB, whilst WbtE shows homology to WbpO and VipA, UDP-GalNAc dehydrogenases involved in the formation of 2-acetamido-2-deoxy-D-galactouronic acid (GalNAcA) in *P. aeruginosa* and *Salmonella enterica* var *typhi* respectively. WbtH produces significant alignments with glutamine amidotransferases, including WbpS of *P. aeruginosa* serotype O6, which may putatively be involved in the formation of the GalNAcAN amido group. Biosynthesis of the fourth sugar, 4N-formyl-quinovosamine (Qui4NFm) most likely involves WbtI, WbtJ, WbtL and WbtM. Sequence homology suggests that WbtL may be involved in the formation of the activated sugar dTDP-D-Glucose with WbtM functioning as a dTDP-D-Glucose 4,6-dehydratase. WbtI is proposed to be involved in Qui4NFm amination since it shows homology to RfbE, a perosamine synthetase. Finally, WbtJ is likely to be responsible for the addition of the N-formyl moiety, showing significant homology to formyltransferases.

Specific glycosyltransferases are required to form the oligosaccharide units of the O-antigen repeat. Four glycosyltransferases would be necessary for the synthesis of each O-antigen unit in *F. tularensis*. Based on homology, WbtB is proposed to mediate the addition of QuiNAc to undecaprenyl phosphate (Und-P) to initiate O-antigen biosynthesis. WbtD and WbtG are probable GalNAcAN transferases, possibly involved in the addition of the two consecutive GalNAcAN residues onto the O-antigen unit. WbtD shares homology to WbpU of *P. aeruginosa* strain O6, proposed to transfer 2-formamido-2-deoxy-D-galactouronamide (GalNFmAN) onto QuiNAc (Belanger M, et al. (1999). *Microbiology* 145: 3505-3521). WbtG is homologous to WbpT of *P. aeruginosa*, thought to be involved in addition of GalNAcA to GalNFmAN. WbtK is probably the fourth glycosyltransferase, which adds 4,6-dideoxy-4-formamido-D-glucose (QuiNA4Fm) to complete the tetrasaccharide O unit.

Wzx and Wzy

Once assembled, the O-antigen repeat units are translocated to the periplasmic face of the inner membrane via Wzx, a transporter/flippase. Wzy then acts as an O-antigen repeat unit polymerase. When analysed using TMHMM, the *F. tularensis* Wzx protein had a predicted 14 trans-membrane helices, with both termini on the cytoplasmic side of the membrane. The *F. tularensis* Wzy protein had a predicted 11 trans-membrane helices, with the amino terminus predicted to be on the cytoplasmic side of the membrane, and the carboxy terminus on the periplasmic side. Additionally, the Wzy protein was predicted to have two large periplasmic domains from amino acids 142-178 and 268-327.

A gene with homology to the O-antigen chain length determinant (wzz) was not identified in the current *F. tularensis* Schu S4 sequence dataset.

PCR Analysis of the O-Antigen Gene Cluster

Eight of the PCR products (primer sets 2, 3, 4, 5, 6, 7, 9 and 10) from each template DNA appeared to be the same size when viewed by agarose gel electrophoresis. Primer pair 1, covering the start of the gene cluster, had to be designed to amplify a 4.8 Kb region due to lack of suitable priming sites upstream of the cluster because of the presence of an insertion element found many times in the *F. tularensis* Schu S4 genome. This primer pair 1 produced the relevant size product for *F. tularensis* Schu S4, but when used on subspecies *holarctica*, strain LVS, did not produce a product. Thus this primer pair may have particular applications in diagnostics where distinction between *F. tularensis* subspecies *tularensis* and *F. tularensis* subspecies *holarctica* is required. Where samples containing DNA from the former is present, a PCR using primer pair 1 will generate a product, which would not be present in the second case.

The PCR using primer pair 8 revealed a difference in size between subspecies *tularensis* strains and subspecies *holarctica* and subspecies *mediaasiatica*. Subspecies *tularensis* strains show a deletion of 303 nucleotides when compared to subspecies *holarctica* strains (including LVS) and subspecies *mediaasiatica*. Cloning and sequence analysis of this region from the subspecies *tularensis* strain Schu S4, the subspecies *holarctica* strain HN63 and LVS has shown that the deletion in Schu S4 occurs at the beginning of a putative transposase that is similar to IS630-spn 1 transposase ORF 1 of *Streptococcus pneumoniae*.

Thus primer pair 8 may also be particularly useful in distinguishing between strains of *F. tularenis*. Following a PCR reaction on samples containing DNA using these primers, a separation of the products on the basis of size, for example on a gel, should reveal distinguishable differences therebetween.

EXAMPLE 2

Protective Effects
LPS Purification

LPS was purified from *F. tularensis* strain Schu S4 or from strain LVS using a hot-phenol and water extraction method mentioned above in Example 1.

Immunization with LPS and Protection Studies

The ability of *F. tularensis* strain LVS or strain Schu S4 LPS to protect BALB/c mice from a *F. tularensis* was determined by immunizing groups of six female BALB/c mice by the i.p. route with the purified LPS obtained. On each dosing occasion, mice were given 50 µg of LPS in phosphate buffered saline (PBS). The mice received three immunizations, each 7 days apart.

Mice were challenged i.p. with *F. tularensis* LVS ($1 \times 10^5$ CFU) 21 days after the last immunization. All control animals died after challenge. Mice which had been immunised LPS isolated from the LVS strain were protected from death. Mice which had been immunised with LPS from either the SchuS4 or LVS strain showed and extended time to death. At a challenge dose of 10 cfu animals Immunised with SchS4 LPS survived for an average of 64 hours (with 99% confidence) longer than the unimmunised controls.

The invention claim is:

1. An isolated nucleic acid which encodes fifteen enzymes involved in O-antigen biosynthesis, wherein the enzymes, when expressed together in a cell, are able to produce an immunogenic moiety able to produce an immune response against *Francisella tularensis* infection in an animal.

2. The isolated nucleic acid of claim 1, which encodes enzymes of SEQ ID NOS 3-17.

3. The isolated nucleic acid of claim 1, having the sequence of SEQ ID NO 1.

4. The isolated nucleic acid of claim 1, wherein the nucleic acid comprises codons that have been optimised for expression in a bacterial cell.

5. The isolated nucleic acid of claim 4, wherein the bacterial cell is *E. coli*.

6. An expression vector comprising the isolated nucleic acid of claim 1.

7. An isolated host cell transformed with the vector of claim 6.

8. A method of preparing an immunogenic composition, which method comprises:
   transforming a host cell with the isolated nucleic acid of claim 1; and,
   culturing said host cell.

9. A method of diagnosing infection by *F. tularensis*, which method comprises detecting SEQ ID NO:1 in a sample taken from a patient suspected of having an infection.

10. A vector comprising an isolated nucleic acid molecule that encodes fifteen enzymes involved in O-antigen biosynthesis, wherein the enzymes, when expressed in a cell, are able to produce an immunogenic moiety able to produce an immune response against *Francisella tularensis* infection in an animal, wherein the isolated nucleic acid molecule encodes enzymes of SEQ ID NOS 3-17.

11. The vector of claim 10, wherein the vector is a bacterial vector.

12. The vector of claim 11, wherein the bacterial vector is a *Salmonella* vector.

13. A composition comprising the vector of claim 10 in combination with a pharmaceutically acceptable carrier.

14. A host cell transformed with the vector of claim 6, wherein the host cell is not a cell of a human patient to whom the isolated nucleic acid is administered.

* * * * *